United States Patent
Mukhopadhyay et al.

(10) Patent No.: US 10,435,402 B2
(45) Date of Patent: Oct. 8, 2019

(54) BICYCLIC COMPOUNDS, COMPOSITIONS AND MEDICINAL APPLICATIONS THEREOF

(71) Applicant: Advinus Therapeutics Limited, Bangalore, Karnataka (IN)

(72) Inventors: Partha Mukhopadhyay, Maharashtra (IN); Yogesh Munot, Maharashtra (IN); Nadim Shaikh, Maharashtra (IN); Bheemashankar A. Kulkarni, Maharashtra (IN); Kasim Mookhtiar, Maharashtra (IN)

(73) Assignee: Advinus Therapeutics Limited, Bangalore, Karnataka (IN)

( * ) Notice: Subject to any disclaimer, the term of this patent is extended or adjusted under 35 U.S.C. 154(b) by 0 days.

(21) Appl. No.: 15/541,875

(22) PCT Filed: Jan. 8, 2016

(86) PCT No.: PCT/IB2016/050078
§ 371 (c)(1),
(2) Date: Jul. 6, 2017

(87) PCT Pub. No.: WO2016/110821
PCT Pub. Date: Jul. 14, 2016

(65) Prior Publication Data
US 2017/0362225 A1 Dec. 21, 2017

(30) Foreign Application Priority Data
Jan. 8, 2015 (IN) .............................. 131/CHE/2015

(51) Int. Cl.
*C07D 471/04* (2006.01)
*A61K 31/5377* (2006.01)
*A61K 31/437* (2006.01)

(52) U.S. Cl.
CPC .......... *C07D 471/04* (2013.01); *A61K 31/437* (2013.01); *A61K 31/5377* (2013.01)

(58) Field of Classification Search
CPC . A61K 31/437; A61K 31/5377; C07D 471/04
USPC .......................................................... 544/112
See application file for complete search history.

(56) References Cited

U.S. PATENT DOCUMENTS

2008/0119457 A1* 5/2008 Huang ................. C07D 207/02
514/217.04

OTHER PUBLICATIONS

Stella (J. Pharmaceutical Sciences, 2010, 99(12), pp. 4755-4765).*

* cited by examiner

*Primary Examiner* — Susanna Moore
(74) *Attorney, Agent, or Firm* — David Bradin; Nexsen Pruet, PLLC

(57) ABSTRACT

Substituted bicyclic compounds of formula (I), their tautomers, polymorphs, stereoisomers, prodrugs, solvates, hydrates, N-oxides, co-crystals, pharmaceutically acceptable salts and pharmaceutical compositions containing them are disclosed, as well as processes for preparing and using the compounds. These compounds are useful in the treatment, prevention, prophylaxis, management, or adjunct treatment of all medical conditions related to inhibition of retinoic acid-related orphan receptor gamma (RORy). Representative conditions include inflammatory and/or autoimmune disorder, rheumatoid arthritis, psoriasis, psoriatic arthritis, multiple sclerosis, inflammatory bowel disease, allergic diseases, asthma, COPD, cancer, cell proliferation, type 1 diabetes, myasthenia gravis, hematopoetic disfunction, systemic lupus, crythematosus or other disorders.

10 Claims, No Drawings

BICYCLIC COMPOUNDS, COMPOSITIONS AND MEDICINAL APPLICATIONS THEREOF

CROSS-REFERENCE TO RELATED APPLICATIONS

This application claims priority under 35 U.S.C. 371 to PCT/IB2016/050078, filed on Jan. 8, 2016, which in turn claims priority to Indian Patent Application Serial No. 131/CHE/2015, filed on Jan. 8, 2015. The contents of each of these applications is incorporated by reference in their entirety for all purposes.

TECHNICAL FIELD

The present disclosure relates to a series of bicyclic compounds, their stereoisomers, tautomers, prodrugs, pharmaceutically acceptable salts, polymorphs, solvates, hydrates, N-oxides, co-crystals and formulations thereof. The disclosure also relates to process of preparation of these bicyclic compounds (I). The compounds of the present disclosure are identified as inhibitors/modulators of retinoic acid-related orphan receptor gamma (RORγ). More particularly, the compounds of present disclosure are useful for preventing; treating or ameliorating RORγ mediated diseases.

BACKGROUND

RORγ is a member of nuclear receptor (NR) superfamily of transcription factor. NR superfamily contains 48 members in humans and includes receptors for steroid hormones, thyroid hormone, various lipids, and oxysterols. NRs function as ligand-dependent transcription factors and share a modular domain structure (Mangelsdorf, D. J et al. *Cell* 83, 835-83, 1995) comprising N'-terminal AF1 (or A/B) and DNA-binding (DBD) domains, followed by C'-terminal ligand binding (LBD) and AF2 (or F) domain; both sides are joined by a flexible hinge region (D).

Many of the NRs, including ROR family members (RORα, RORβ and RORγ), do not have validated ligands and are called orphan nuclear receptors. RORγ is expressed as two isoforms due to alternative splicing from RORC gene. The shorter transcript called RORγt or RORγ2 lacks two exons at 5'-terminal. Unlike widely expressed RORγ in several tissues including the thymus, kidney, liver, and mussels, RORγt is expressed exclusively in immature CD4+ CD8+ double positive thymocytes and in a population of lymphoid tissue inducers (LTi) of fetal lever. Among mature T cells, RORγt is expressed in IL-17 secreting T cell populations (eg. Th17, γδT cells etc). The highly conserved N'-DBD of RORγ(t) recognizing AGGTCA on DNA (RORE), while C'-terminal LBD contains 12 α-helices of which H3-H5 are important for co activator or co repressor interactions; H12 contains core motif LYKELF of AF2 domain. At resting stage, RORγt is localized in nucleus and upon ligand binding binds to DNA as monomer (Jetten, M., et al. *Prog Nucleic acid Res Mol Biol* 69, 205-247, 2001).

RORγt is the signature transcription factor for differentiation and function of IL-17 producing T Helper (Th17) cell lineage, a newly discovered subset of T-helper cell population. Th17 cells are major producer of IL-17A, IL-17F, IL-22, IL-21 proinflammatory cytokines, which have a major role in many of inflammatory and autoimmune diseases but not limited to psoriasis, multiple sclerosis, rheumatoid arthritis, inflammatory bowl diseases, COPD, Colitis, Crohhn's disease and asthma (Lock et al. *Nat. Med.* 8, 2002, 500-508; Tzartos et al. *Am. J. Pathol*, 172, 208, 146-155; Koteke et al. *J clin. Invest*, 103, 1999, 1345-1352; Kirkham et al. *Arthritis Rheum*, 54, 2006, 1122; Seiderer et al. *Inflamm. Bowel Dis.* 14, 208, 437-445; Wong et al. *Clin. Exp. Immunol.* 125, 2001, 177-183; Agache et al. *Respir. Med.* 104, 2010, 1131-1137. In murine models of these diseases, inhibition of IL-17 function by neutralizing antibodies or generic disruption of IL-17 or Il-17 receptors amelioraties the diseases course or clinical symptoms (Hu et al. *Ann. N.Y. Acad Sci.* 1217, 2011, 60-67).

There are recent evidences for role of Th17 in other autoimmune diseases like systemic lupus erythematosus, Behcet's syndrome, scleroderma, transplant rejection and asthma. Th17 cells cause major inflammatory response by direct as well as indirect methods, like neutrophil infiltration by IL-17, tissue damage, keratinocyte proliferation by IL-22 etc. Hence, small molecule antagonists of RORγt are expected to inhibit production of these pro-inflammatory cytokines and have broad potential as novel anti-inflammatory compounds Huang, Q., et al. *Arthritis Rheumat* 56, 2192-2201, 7, 2007; Kimura, A., et al. *Internat Immunopharmacol* 11, 319-322, 2011. RORγt inhibitors might be useful in diseases where increased levels of TH17 cells and/or elevated levels of IL-17, IL-22 and IL-23 in infectious disease like mucosal leishmaniasis and many more (Boaventura et al. *Eur. J immunol.* 40, 2010, 2830-2836; Hashimoto thyroiditis (Figuerovega et al. *J. Clin. Endocrinol. Metab.* 95, 2010, 953-962 and Kawasaki disease (Jie et al. *Clin. Exp. Immunol.* 162, 131-137, 2010). Mouse model of cancer showed relevance TH17 cells. Evidences suggest that the effector T cell subset is also involved in tumor immunology, thus giving a way to a new target for cancer therapy (*Nat. rev. Immuno.* 10, 248-256, 2010). The approach of targeting TH-17 cells also validate in clinical studies with several IL-17 antibodies for several autoimmune disorders.

Disrupting of RORγt in mice also attenuates disease progression or severity in animal models of autoimmunity and inflammation including experimental autoimmune encephalomyelitis (EAE), imiquimod induced psoriasis, colitis and allergic airway disease (Ivanov et al. *cell*, 126, 2006, 1121-1133; Young et al. *Immunity*, 28, 2008, 29-39; Pantelyushin et al. *J. Clin Invest*. 122, 2012, 2252-2256; Leppkes et al. *Gastroentrology*, 136, 2009, 257-267 and Tilley et al *J. Immunol*. 178, 2007, 3208-3218.

Several patent applications and publications describe the discovery of small molecule RORγt inhibitors like thiazoles in WO2012027965 and WO 2012/028100; benzoxazepins in WO 2011107248; amide compounds in WO 2011112263; indole and indazole amides in WO2012106995, WO2014026329 and WO2012064744; isooxazole in WO2012147916; sulfonamides and cyclic sulfonamides in WO2014009447 and WO2013092939; quinolines in WO2014062667; pyrimidine in WO2014062938; pyridine in WO2014125426.

No RORγt inhibitor has yet reached the marketing stage. Therefore, there remains a need for discovering novel RORγ inhibitors possessing desirable properties such as pharmacokinetic/pharmacodynamic and or physicochemical and/or other drug like profiles to advance into clinics.

Therefore, there is a strong need for novel small molecule RORγ modulators that will have potential clinical utility. These compounds will have medical applications in the disease area of inflammation, autoimmune disorder and cell proliferation, rheumatoid arthritis, psoriasis, psoriatic arthritis, systemic lupus erythematosus, Sjögren's Syndrome, multiple sclerosis, inflammatory bowel disease, allergic diseases, infectious diseases affecting immune system, asthma, type 1 diabetes, myasthenia gravis, hematopoetic disfunction, transplant rejection, cancers, COPD and graft-versus-host disease.

WO2013131923, WO2013104598, WO2013030288, US20120029002 and US20100029653 disclose a compound represented by the formula:

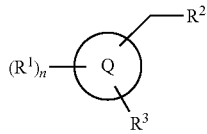

Wherein each symbol is as defined in the specification, as useful in the treatment and/or prophylaxis of cardiovascular disorders.

US 20070043057 and US 20070015771 disclose a compound represented by the formula:

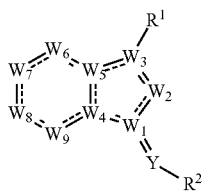

Wherein each symbol is as defined in the specification, as anticancer agents.

The present disclosure provides a series of novel bicyclic compounds characterized as RORγ inhibitors and their potential use in pathogenesis of diseases as medicament for the treatment of RORγ mediated diseases.

SUMMARY

The present disclosure provides bridgehead nitrogen bicyclic compounds of Formula (I), their tautomers, polymorphs, stereoisomers, prodrugs, solvates, pharmaceutically acceptable salts, pharmaceutical compositions containing them and methods of treating conditions and diseases that are mediated by RORγ activity Formula (I)

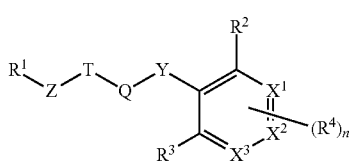

Q represents a bicyclic group selected from formula (a)

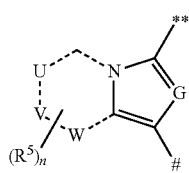

-continued (b)

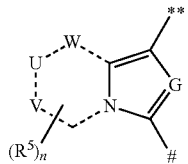

Where
** represents point of attachment of T;
# represents point of attachment of Y;
Each "------" is independently a single or double bond;
U, V, W and G are independently selected from N, NR', CR' and CR'R";
R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or
R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;
T and Y is selected from
a) T is a monocyclic or a bicyclic carbocyclic ring system which is saturated, unsaturated or partially unsaturated ring system which is optionally substituted with 1 to 4 substituents independently selected from halo, alkyl, alkenyl, alkynyl, nitro, cyano, —(CR$^a$R$^b$)$_m$OR$^6$, —(CR$^a$R$^b$)$_m$SR$^6$, —(CR$^a$R$^b$)$_m$NR$^7$R$^8$, oxo, alkylsulfonyl, —(CR$^a$R$^b$)$_n$COOR$^6$, —(CR$^a$R$^b$)$_m$C(O)NR$^7$R$^8$, cycloalkyl, cycloalkylalkyl, aryl, arylalkyl, heterocyclyl, heterocyclylalkyl, heteroaryl, or heteroarylalkyl;
Y is group selected from —O—, —S(O)$_p$—, —N(R$^7$)—, —C(O)—, —C(S)— and —(CR$^a$R$^b$)—; or
b) T is a monocyclic or a bicyclic ring system which is saturated, unsaturated or partially unsaturated ring system and optionally have additional heteroatoms selected from O, N or S, said is optionally substituted with 1 to 4 substituents independently selected from halo, alkyl, alkenyl, alkynyl, nitro, cyano, —(CR$^a$R$^b$)$_m$OR$^6$, —(CR$^a$R$^b$)$_m$SR$^6$, —(CR$^a$R$^b$)$_n$NR$^7$R$^8$, oxo, alkylsulfonyl, —(CR$^a$R$^b$)$_m$COOR$^6$, —(CR$^a$R$^b$)$_m$C(O)NR$^7$R$^8$, cycloalkyl, cycloalkylalkyl, aryl, arylalkyl, heterocyclyl, heterocyclylalkyl, heteroaryl, or heteroarylalkyl;
Y is group selected from —C(O)— and —C(S)—;
R$^a$ and R$^b$ are independently selected from the group consisting of hydrogen, —OR$^7$, halogen, haloalkyl, perhaloalkyl and alkyl;
R$^a$ and R$^b$ taken together form a monocyclic or a bicyclic ring system which is saturated or partially unsaturated and optionally have additional heteroatoms selected from O, N or S;
X$^1$, X$^2$ and X$^3$ are each independently selected from N and CR$^7$;
Z is —C(O)— or —S(O)$_p$—;
R$^1$, R$^4$ and R$^5$ are independently selected from hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —$NR^7R^8$, —$OR^7$, —$S(O)_pR^7$, —$S(O)_pNR^7R^8$, —$NR^7S(O)_pR^8$, —$NR^7C(O)R^8$, —$OS(O)_pR^8$, —$NR^7C(O)OR^8$, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(R^7R^8)_nNR^7R^8$, —$C(R^7R^8)_nCO(R^7)$ and —$S(O)_pC(R^7R^8)_nC(O)OR^7$, or when $R^4$ or $R^5$ are more than one, then any 2 $R^4$ or 2 $R^5$ independently is optionally, taken together form a monocyclic or a bicyclic ring system which is saturated or partially unsaturated and optionally have additional heteroatoms selected from O, N or S;
  wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, —$(CR^aR^b)_nCOOR^7$, —$(CR^aR^b)_nNR^7R^8$, —$(CR^aR^b)_nC(O)NR^7R^8$, —$S(O)_pR^7$ or —$SO_3H$.;
$R^2$ and $R^3$ are independently selected from halo, hydroxyl, cyano, $C_{1-6}$alkyl, $C_{2-6}$alkenyl, $C_{2-6}$alkynyl, haloalkyl, perhaloalkyl, cycloalkyl, cycloalkenyl, cycloalkylalkyl, aryl or arylalkyl;
$R^6$ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;
$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or
$R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;
p=0-2;
n=0-4

DETAILED DESCRIPTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "substituted alkyl" or "substituted alkylene" refers to: (1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^b$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2; or (2) an alkyl group or alkylene group as defined above that is interrupted by 1, 2, 3, 4, 5, 6, 7, 8, 9 or 10 atoms independently selected from oxygen, sulphur and $NR^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, $CF_3$, amino, substituted amino, cyano, or —$S(O)_pR^c$, in which $R^c$ is alkyl, aryl, or heteroaryl and p is 0, 1, or 2; or (3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl(—CH=$CH_2$), 1-propylene or allyl (—$CH_2CH$=$CH_2$), isopropylene (—$C(CH_3)$=$CH_2$), bicyclo [2.2.1] heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$ where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_p$ $R^c$, where $R^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —$CH_2$C≡CH), homopropargyl (or but-1-yn-4-yl, —$CH_2CH_2$C≡CH) and the like.

The term "alkynylene" refers to a diradical of a branched or an unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —$SO_3H$, aryl, aryloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$, where each $R^a$ is independently selected from the group consisting of hydrogen, alkyl, cycloalkyl, cycloalkylalkyl, aryl, arylalkyl, heteroaryl heteroarylalkyl, heterocyclyl, heterocyclylalkyl and heterocyclyloxy, where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$ where $R^c$ is alkyl, aryl, or heteroaryl and p is 0, 1 or 2.

The term "cycloalkyl" refers to unless otherwise mentioned, carbocyclic groups of from 3 to 20 carbon atoms having a single cyclic ring or multiple condensed rings or spirocyclic rings or bridged rings which may be saturated or partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, bicyclo[2.2.2] octane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, amino sulfonyl, aminocarbonylamino, heteroaryloxy, heterocyclyl, heterocyclyloxy, hydroxyamino, alkoxyamino, nitro, —C(O)R and —$S(O)_p$ $R^b$, where R is hydrogen, hydroxyl, alkoxy, alkyl and cyclocalkyl, heterocyclyloxy where $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group $R'''$—O—, where $R'''$ is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O) NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "acylamino" refers to the group NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, $CF_3$, amino, substituted amino, cyano, and —$S(O)_pR^c$, where $R^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, or —$S(O)_pR^c$, where $R^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl, ethoxyethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to $(C_{1-6})$alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, CF$_3$, amino, substituted amino, cyano, and —S(O)$_p$R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)OR$^d$ where R$^d$ is alkyl, cycloalkyl, where alkyl, cycloalkyl are as defined herein, and may be optionally further substituted by alkyl, halogen, CF$_3$, amino, substituted amino, cyano, or —S(O)$_p$R$^c$, in which R$^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulphur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4] oxadiazole, [1,3,4] oxadiazole, [1,2,4] thiadiazole, [1,3,4] thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_n$R$^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings or spirocyclic rings, or bridged rings unless otherwise mentioned, having from 1 to 40 carbon atoms and from 1 to 10 hetero atoms, preferably 1, 2, 3 or 4 heteroatoms, selected from nitrogen, sulphur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)$_p$R$^b$, where R$^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)R$^c$, where R$^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" or "substituted sulfone" refers to a group —S(O)$_2$R, in which R is alkyl, aryl, or heteroaryl.

The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g.

calcium or magnesium) hydroxides and organic bases, for example alkyl amines, arylalkyl amines and heterocyclic amines.

Other preferred salts according to the disclosure are quaternary ammonium compounds wherein an equivalent of an anion (M-) is associated with the positive charge of the N atom. M- may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. M- is preferably an anion selected from chloride, bromide, iodide, sulphate, nitrate, acetate, maleate, oxalate, succinate or trifluoroacetate. More preferably M- is chloride, bromide, trifluoroacetate or methanesulphonate.

The present disclosure provides compounds of formula (I), their tautomers, polymorphs, stereoisomers, prodrugs, solvates, pharmaceutically acceptable salts, pharmaceutical compositions containing them and methods of treating conditions and diseases that are mediated by RORγ activity,

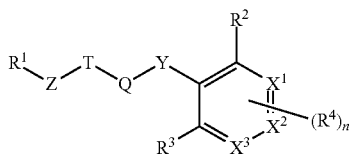

Formula (I)

Q represents a bicyclic group selected from formula

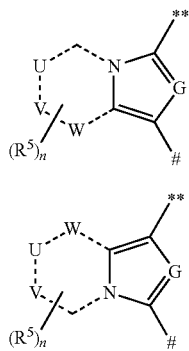

** represents point of attachment of T;
# represents point of attachment of Y;
Each "------" is independently a single or double bond;
U, V, W and G are independently selected from N, NR', CR' and CR'R";
R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or
R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

T and Y is selected from
a) T is a monocyclic or a bicyclic carbocyclic ring system which is saturated, unsaturated or partially unsaturated ring system which is optionally substituted with 1 to 4 substituents independently selected from halo, alkyl, alkenyl, alkynyl, nitro, cyano, $-(CR^aR^b)_mOR^6$, $-(CR^aR^b)_mSR^6$, $-(CR^aR^b)_mNR^7R^8$, oxo, alkylsulfonyl, $-(CR^aR^b)_mCOOR^6$, $-(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;
Y is a group selected from $-O-$, $-S(O)_p-$, $-N(R^7)-$, $-C(O)-$, $-C(S)-$ and $-(CR^aR^b)-$; or
b) T is a monocyclic or a bicyclic ring system which is saturated, unsaturated or partially unsaturated ring system and optionally have additional heteroatoms selected from O, N or S, said is optionally substituted with 1 to 4 substituents independently selected from halo, alkyl, alkenyl, alkynyl, nitro, cyano, $-(CR^aR^b)_mOR^6$, $-(CR^aR^b)_mSR^6$, $-(CR^aR^b)_mNR^7R^8$, oxo, alkylsulfonyl, $-(CR^aR^b)_mCOOR^6$, $-(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;
Y is a group selected from $-C(O)-$ and $-C(S)-$;
$R^a$ and $R^b$ are independently selected from the group consisting of hydrogen, $-OR^7$, halogen, haloalkyl, perhaloalkyl and alkyl; or
$R^a$ and $R^b$ taken together form a monocyclic or a bicyclic ring system which is saturated or partially unsaturated and optionally have additional heteroatoms selected from O, N or S;
$X^1$, $X^2$ and $X^3$ are each independently selected from N and $CR^7$;
Z is $-C(O)-$ or $-S(O)_p-$;
$R^1$, $R^4$ and $R^5$ are independently selected from hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, $-NR^7R^8$, $-OR^7$, $-S(O)_pR^7$, $-S(O)_pNR^7R^8$, $-NR^7S(O)_pR^8$, $-NR^7C(O)R^8$, $-OS(O)_pR^8$, $-NR^7C(O)OR^8$, $-(CR^7R^8)_nC(O)OR^7$, $-(CR^7R^8)_n(CO)NR^7R^8$, $-(CR^7R^8)_nS(O)_pNR^7R^8$, $-(CR^7R^8)_nN(R^7)C(O)OR^7$, $-(CR^7R^8)_nOR^7$, $-C(R^7R^8)_nNR^7R^8$, $-C(R^7R^8)_nCO(R^7)$ and $-S(O)_pC(R^7R^8)_nC(O)OR^7$, or when $R^4$ or $R^5$ are more than one, then any 2 $R^4$ or 2 $R^5$ independently is optionally, taken together form a monocyclic or a bicyclic ring system which is saturated or partially unsaturated and optionally have additional heteroatoms selected from O, N or S;
wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, $-(CR^aR^b)_nCOOR^7$, $-(CR^aR^b)_nNR^7R^8$, $-(CR^aR^b)_nC(O)NR^7R^8$, $-S(O)_pR^7$ or $-SO_3H$.;
$R^2$ and $R^3$ are independently selected from halo, hydroxyl, cyano, $C_{1-6}$alkyl, $C_{2-6}$alkenyl, $C_{2-6}$alkynyl, haloalkyl, perhaloalkyl, cycloalkyl, cycloalkenyl, cycloalkylalkyl, aryl, and arylalkyl;
$R^6$ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

R⁷ and R⁸ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R⁷ and R⁸ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

p=0-2;
n=0-4

According to another embodiment, the present disclosure relates to compounds of formula (I) or its tautomers, polymorphs, stereoisomers, prodrugs, solvate or a pharmaceutically acceptable salts thereof, wherein, U, V and W are independently selected from N, NR', CR' and CR'R";

G is CR';

R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

T and Y is selected from a) T is a monocyclic or a bicyclic carbocyclic ring system which is saturated, unsaturated or partially unsaturated ring system which is optionally substituted with 1 to 4 substituents independently selected from halo, alkyl, alkenyl, alkynyl, nitro, cyano, —(CR$^a$R$^b$)$_m$OR⁶, —(CR$^a$R$^b$)$_m$SR⁶, —(CR$^a$R$^b$)$_m$NR⁷R⁸, oxo, alkylsulfonyl, —(CR$^a$R$^b$)$_m$COOR⁶, —(CR$^a$R$^b$)$_m$C(O)NR⁷R⁸, cycloalkyl, cycloalkylalkyl, aryl, arylalkyl, heterocyclyl, heterocyclylalkyl, heteroaryl, or heteroarylalkyl;

Y is a group selected from —O—, —S(O)$_p$—, —N(R⁷)—, —C(O)—, —C(S)— and —(CR$^a$R$^b$)—; or b) T is a monocyclic or a bicyclic ring system which is saturated, unsaturated or partially unsaturated ring system and optionally have additional heteroatoms selected from O, N or S, said is optionally substituted with 1 to 4 substituents independently selected from halo, alkyl, alkenyl, alkynyl, nitro, cyano, —(CR$^a$R$^b$)$_m$OR⁶, —(CR$^a$R$^b$)$_m$SR⁶, —(CR$^a$R$^b$)$_m$NR⁷R⁸, oxo, alkylsulfonyl, —(CR$^a$R$^b$)$_m$COOR⁶, —(CR$^a$R$^b$)$_m$C(O)NR⁷R⁸, cycloalkyl, cycloalkylalkyl, aryl, arylalkyl, heterocyclyl, heterocyclylalkyl, heteroaryl, or heteroarylalkyl;

Y is a group selected from —C(O)— and —C(S)—;

R$^a$ and R$^b$ are independently selected from the group consisting of hydrogen, —OR⁷, halogen, haloalkyl, perhaloalkyl and alkyl; or R$^a$ and R$^b$ taken together form a monocyclic or a bicyclic ring system which is saturated or partially unsaturated and optionally have additional heteroatoms selected from O, N or S;

X¹, X² and X³ are each independently selected from N and CR⁷;

Z is —C(O)— or —S(O)$_p$—;

R¹, R⁴ and R⁵ are independently selected from hydrogen, halogen, alkyl, hydroxy, alkoxy, amino, alkenyl, alkynyl, cycloalkyl, cycloalkylalkyl, heterocyclyl, heterocloalkyl, aryl, arylalkyl, heteroaryl, heteroarylalkyl, tetrazolyl, tetrazolylalkyl, mono, di or tri substituted haloalkyl, nitrile, nitro, oxo, —NR⁷R⁸, —OR⁷, —S(O)$_p$R⁷, —S(O)$_p$NR⁷R⁸, —NR⁷S(O)$_p$R⁸, —NR⁷C(O)R⁸, —OS(O)$_p$R⁸, —NR⁷C(O)OR⁸, —(CR⁷R⁸)$_n$C(O)OR⁷, —(CR⁷R⁸)$_n$(CO)NR⁷R⁸, —(CR⁷R⁸)$_n$S(O)$_p$NR⁷R⁸, —(CR⁷R⁸)$_n$N(R⁷)C(O)R⁷, —(CR⁷R⁸)$_n$OR⁷, —C(R⁷R⁸)$_n$NR⁷R⁸, —C(R⁷R⁸)$_n$CO(R⁷) and —S(O)$_p$C(R⁷R⁸)$_n$C(O)OR⁷, or when R¹ or R⁴ or R⁵ are more than one, then any 2 R¹ or 2 R⁴ or 2 R⁵ independently is optionally, taken together form a monocyclic or a bicyclic ring system which is saturated or partially unsaturated and optionally have additional heteroatoms selected from O, N or S;

wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, —(CR$^a$R$^b$)$_n$COOR⁷, —(CR$^a$R$^b$)$_n$NR⁷R⁸, —(CR$^a$R$^b$)$_n$C(O)NR⁷R⁸, —S(O)$_p$R⁷ or —SO₃H.;

R² and R³ are independently selected from halo, hydroxyl, cyano, C$_{2-6}$alkenyl, C$_{2-6}$alkynyl, haloalkyl, perhaloalkyl, cycloalkyl, cycloalkenyl, cycloalkylalkyl, aryl, and arylalkyl;

R⁶ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

R⁷ and R⁸ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R⁷ and R⁸ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

p=0-2;
n=0-4

According to another embodiment, the present disclosure relates to compounds of formula (I) or its tautomers, polymorphs, stereoisomers, prodrugs, solvate or a pharmaceutically acceptable salts thereof, wherein, U, V and W are independently selected from N, NR', CR' and CR'R";

G is CR';

R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

T and Y is selected from
  a) T is a monocyclic or a bicyclic carbocyclic ring system which is saturated, unsaturated or partially unsaturated ring system which is optionally substituted with 1 to 4 substituents independently selected from halo, alkyl, alkenyl, alkynyl, nitro, cyano, $-(CR^aR^b)_mOR^6$, $-(CR^aR^b)_mSR^6$, $-(CR^aR^b)_mNR^7R^8$, oxo, alkylsulfonyl, $-(CR^aR^b)_mCOOR^6$, $-(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;
     Y is a group selected from —O—, $-S(O)_p-$, $-N(R^7)-$, —C(O)—, —C(S)— and $-(CR^aR^b)-$; or
  b) T is a monocyclic or a bicyclic ring system which is saturated, unsaturated or partially unsaturated ring system and optionally have additional heteroatoms selected from O, N or S, said is optionally substituted with 1 to 4 substituents independently selected from halo, alkyl, alkenyl, alkynyl, nitro, cyano, $-(CR^aR^b)_mOR^6$, $-(CR^aR^b)_mSR^6$, $-(CR^aR^b)_mNR^7R^8$, oxo, alkylsulfonyl, $-(CR^aR^b)_mCOOR^6$, $-(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;
     Y is a group selected from —C(O)— and —C(S)—;

$R^a$ and $R^b$ are independently selected from the group consisting of hydrogen, $-OR^7$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S;

$X^1$, $X^2$ and $X^3$ are each independently selected from N and $CR^7$;

Z is —C(O)— or $-S(O)_p-$;

$R^1$, $R^4$ and $R^5$ are independently selected from hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, $-NR^7R^8$, $-OR^7$, $-S(O)_pR^7$, $-S(O)_pNR^7R^8$, $-NR^7S(O)_pR^8$, $-NR^7C(O)R^8$, $-OS(O)_pR^8$, $-NR^7C(O)OR^8$, $-(CR^7R^8)_nC(O)OR^7$, $-(CR^7R^8)_n(CO)NR^7R^8$, $-(CR^7R^8)_nS(O)_pNR^7R^8$, $-(CR^7R^8)_nN(R^7)C(O)R^7$, $-(CR^7R^8)_nOR^7$, $-C(R^7R^8)_nNR^7R^8$, $-C(R^7R^8)_nCO(R^7)$ and $-S(O)_pC(R^7R^8)_nC(O)OR^7$; or when $R^4$ or $R^5$ are more than one, then any 2 $R^4$ or 2 $R^5$ independently is optionally, taken together form a monocyclic or a bicyclic ring system which is saturated or partially unsaturated and optionally have additional heteroatoms selected from O, N or S;
  wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, $-(CR^aR^b)_nCOOR^7$, $-(CR^aR^b)_nNR^7R^8$, $-(CR^aR^b)_nC(O)NR^7R^8$, $-S(O)_pR^7$ or $-SO_3H$.;

$R^2$ and $R^3$ are independently selected from halo, hydroxyl, cyano, $C_{1-6}$alkyl, haloalkyl, perhaloalkyl, cycloalkyl, cycloalkenyl, cycloalkylalkyl, aryl, and arylalkyl;

$R^6$ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

p=0-2;

n=0-4

According to another embodiment, the present disclosure relates to compounds of formula (I) or its tautomers, polymorphs, stereoisomers, prodrugs, solvate or a pharmaceutically acceptable salts thereof, wherein, U, V and W are independently selected from N, NR', CR' and CR'R";

G is CR';

R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

T and Y is selected from
  a) T is cycloalkyl, cycloalkenyl, cycloalkylalkyl, aryl and arylalkyl;
     wherein cycloalkyl, cycloalkenyl, cycloalkylalkyl, aryl and arylalkyl are unsubstituted or substituted independently with 1 to 4 substituents independently selected from halo, alkyl, alkenyl, alkynyl, nitro, cyano, $-(CR^aR^b)_mOR^6$, $-(CR^aR^b)_mSR^6$, $-(CR^aR^b)_mNR^7R^8$, oxo, alkylsulfonyl, $-(CR^aR^b)_mCOOR^6$, $-(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;
     Y is a group selected from —O—, $-S(O)_p-$, $-N(R^7)-$, —C(O)—, —C(S)— and $-(CR^aR^b)-$; or
  b) T is cycloalkyl, cycloalkenyl, cycloalkylalkyl, aryl, arylalkyl, heterocyclyl, heterocyclylalkyl, heteroaryl or heteroarylalkyl;
     wherein cycloalkyl, cycloalkylalkyl, aryl, arylalkyl, heterocyclyl, heterocyclylalkyl, heteroaryl and heteroarylalkyl are unsubstituted or substituted independently with 1 to 4 substituents independently selected from halo, alkyl, alkenyl, alkynyl, nitro, cyano, $-(CR^aR^b)_mOR^6$, $-(CR^aR^b)_mSR^6$, $-(CR^aR^b)_mNR^7R^8$, oxo, alkylsulfonyl, $-(CR^aR^b)_mCOOR^6$, $-(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;

Y is a group selected from —C(O)— and —C(S)—;

$R^a$ and $R^b$ are independently selected from the group consisting of hydrogen, —$OR^7$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S;

$X^1$, $X^2$ and $X^3$ are each independently selected from N and $CR^7$;

Z is —C(O)— or —$S(O)_p$—;

$R^1$, $R^4$ and $R^5$ are independently selected from hydrogen, halogen, alkyl, hydroxy, alkoxy, amino, alkenyl, alkynyl, cycloalkyl, cycloalkylalkyl, heterocyclyl, heterocloalkyl, aryl, arylalkyl, heteroaryl, heteroarylalkyl, tetrazolyl, tetrazolylalkyl, mono, di or tri substituted haloalkyl, nitrile, nitro, oxo, —$NR^7R^8$, —$OR^7$, —$S(O)_pR^7$, —$S(O)_pNR^7R^8$, —$NR^7S(O)_pR^8$, —$NR^7C(O)R^8$, —$OS(O)_pR^8$, —$NR^7C(O)OR^8$, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(R^7R^8)_nNR^7R^8$, —$C(R^7R^8)_nCO(R^7)$ and —$S(O)_pC(R^7R^8)_nC(O)OR^7$; or when $R^4$ or $R^5$ are more than one, then any 2 $R^4$ or 2 $R^5$ independently is optionally, taken together form a monocyclic or a bicyclic ring system which is saturated or partially unsaturated and optionally have additional heteroatoms selected from O, N or S;

wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, —$(CR^aR^b)_nCOOR^7$, —$(CR^aR^b)_nNR^7R^8$, —$(CR^aR^b)_nC(O)NR^7R^8$, —$S(O)_pR^7$ or —$SO_3H$.;

$R^2$ and $R^3$ are independently selected from halo, hydroxyl, cyano, $C_{2-6}$alkenyl, $C_{2-6}$alkynyl, haloalkyl, perhaloalkyl, cycloalkyl, cycloalkenyl, cycloalkylalkyl, aryl, and arylalkyl;

$R^6$ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

p=0-2;
n=0-4

According to another embodiment, the present disclosure relates to compounds of formula (I) or its tautomers, polymorphs, stereoisomers, prodrugs, solvate or a pharmaceutically acceptable salts thereof, wherein, U, V and W are independently selected from N, NR', CR' and CR'R";

G is CR';

R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

T and Y is selected from a) T is cyclopropyl, cyclopentyl, cyclohexyl, cyclopentenyl, cyclohexenyl, phenyl,
   wherein T is unsubstituted or substituted with 1 to 4 substituents independently selected from halo, alkyl, alkenyl, alkynyl, nitro, cyano, —$(CR^aR^b)mOR^6$, —$(CR^aR^b)mSR^6$, —$(CR^aR^b)mNR^7R^8$, oxo, alkylsulfonyl, —$(CR^aR^b)_mCOOR^6$, —$(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;

Y is a group selected from —O—, —$S(O)_p$—, —$N(R^7)$—, —C(O)—, —C(S)— and —$(CR^aR^b)$—; or b) T is selected from cyclopropyl, cyclopentyl, cyclohexyl, cyclopentenyl, cyclohexenyl, phenyl, tetrahydrofuranyl, pyrrolidinyl, pyridinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl or benzooxazolyl wherein T is unsubstituted or substituted with 1 to 4 substituents independently selected from halo, alkyl, alkenyl, alkynyl, nitro, cyano, —$(CR^aR^b)_mOR^6$, —$(CR^aR^b)_mSR^6$, —$(CR^aR^b)_mNR^7R^8$, oxo, alkylsulfonyl, —$(CR^aR^b)_mCOOR6$, —$(CR^aR^b)_mC(O)NR^7R^8$, cycloalkyl, cycloalkylalkyl, aryl, arylalkyl, heterocyclyl, heterocyclylalkyl, heteroaryl, or heteroarylalkyl;

Y is a group selected from —C(O)— and —C(S)—;

$R^a$ and $R^b$ are independently selected from the group consisting of hydrogen, —$OR^7$, halogen, haloalkyl, perhaloalkyl and alkyl; or $R^a$ and $R^b$ taken together form a monocyclic or a bicyclic ring system which is saturated or partially unsaturated and optionally have additional heteroatoms selected from O, N or S;

$X^1$, $X^2$ and $X^3$ are each independently selected from N and $CR^7$;

Z is —C(O)— or —$S(O)_p$—;

$R^1$, $R^4$ and $R^5$ are independently selected from hydrogen, halogen, alkyl, hydroxy, alkoxy, amino, alkenyl, alkynyl, cycloalkyl, cycloalkylalkyl, heterocyclyl, heterocloalkyl, aryl, arylalkyl, heteroaryl, heteroarylalkyl, tetrazolyl, tetrazolylalkyl, mono, di or tri substituted haloalkyl, nitrile, nitro, oxo, —$NR^7R^8$, —$OR^7$, —$S(O)_pR^7$, —$S(O)_pNR^7R^8$, —$NR^7S(O)_pR^8$, —$NR^7C(O)R^8$, —$OS(O)_pR^8$, —$NR^7C(O)OR^8$, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(R^7R^8)_nNR^7R^8$, —$C(R^7R^8)_nCO(R^7)$ and —$S(O)_pC(R^7R^8)_nC(O)OR^7$, or when $R^4$ or $R^5$ are more than one, then any 2 $R^4$ or 2 $R^5$ independently is optionally, taken together form a monocyclic or a bicyclic ring system which is saturated or partially unsaturated and optionally have additional heteroatoms selected from O, N or S;
wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, —(CR$^a$R$^b$)$_n$COOR$^7$, —(CR$^a$R$^b$)$_n$NR$^7$R$^8$, —(CR$^a$R$^b$)$_n$C(O)NR$^7$R$^8$, —S(O)$_p$R$^7$ or —SO$_3$H.;

$R^2$ and $R^3$ are independently selected from halo, hydroxyl, cyano, $C_{1-6}$alkyl, $C_{2-6}$alkenyl, $C_{2-6}$alkynyl, haloalkyl, perhaloalkyl, cycloalkyl, cycloalkenyl, cycloalkylalkyl, aryl, and arylalkyl;

$R^6$ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

p=0-2;
n=0-4

According to another embodiment, the present disclosure relates to compounds of formula (I) or its tautomers, polymorphs, stereoisomers, prodrugs, solvate or a pharmaceutically acceptable salts thereof, wherein, U, V and W are independently selected from N, NR', CR' and CR'R";
G is CR';
R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

T is selected from cyclopropyl, cyclopentyl, cyclohexyl, cyclopentenyl, cyclohexenyl, phenyl, tetrahydrofuranyl, pyrrolidinyl, pyridinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl or benzooxazolyl
wherein T is unsubstituted or substituted with 1 to 4 substituents independently selected from halo, alkyl, alkenyl, alkynyl, nitro, cyano, —(CR$^a$R$^b$)mOR$^6$, —(CR$^a$R$^b$)$_m$SR$^6$, —(CR$^a$R$^b$)$_m$NR$^7$R$^8$, oxo, alkylsulfonyl, —(CR$^a$R$^b$)$_m$COOR$^6$, —(CR$^a$R$^b$)$_m$C(O)NR$^7$R$^8$, cycloalkyl, cycloalkylalkyl, aryl, arylalkyl, heterocyclyl, heterocyclylalkyl, heteroaryl, or heteroarylalkyl;

Y is group selected from —O—, —S(O)$_p$—, —N(R$^7$)—, —C(O)—, —C(S)— and —(CR$^a$R$^b$)—;

R$^a$ and R$^b$ are independently selected from the group consisting of hydrogen, —OR$^7$, halogen, haloalkyl, perhaloalkyl and alkyl; or R$^a$ and R$^b$ taken together form a monocyclic or a bicyclic ring system which is saturated or partially unsaturated and optionally have additional heteroatoms selected from O, N or S;

$X^1$, $X^2$ and $X^3$ are each independently selected from N and CR$^7$;

Z is —C(O)— or —S(O)$_p$—;

$R^1$, $R^4$ and $R^5$ are independently selected from hydrogen, halogen, alkyl, hydroxy, alkoxy, amino, alkenyl, alkynyl, cycloalkyl, cycloalkylalkyl, heterocyclyl, heterocloalkyl, aryl, arylalkyl, heteroaryl, heteroarylalkyl, tetrazolyl, tetrazolylalkyl, mono, di or tri substituted haloalkyl, nitrile, nitro, oxo, —NR$^7$R$^8$, —OR$^7$, —S(O)$_p$R$^7$, —S(O)$_p$NR$^7$R$^8$, —NR$^7$S(O)$_p$R$^8$, —NR$^7$C(O)R$^8$, —OS(O)$_p$R$^8$, —NR$^7$C(O)OR$^8$, —(CR$^7$R$^8$)$_n$C(O)OR$^7$, —(CR$^7$R$^8$)$_n$(CO)NR$^7$R$^8$, —(CR$^7$R$^8$)$_n$S(O)$_p$NR$^7$R$^8$, —(CR$^7$R$^8$)$_n$N(R$^7$)C(O)R$^7$, —(CR$^7$R$^8$)$_n$OR$^7$, —C(R$^7$R$^8$)$_n$NR$^7$R$^8$, —C(R$^7$R$^8$)$_n$CO(R$^7$) and —S(O)$_p$C(R$^7$R$^8$)$_n$C(O)OR$^7$, or when $R^4$ or $R^5$ are more than one, then any 2 $R^4$ or 2 $R^5$ independently is optionally, taken together form a monocyclic or a bicyclic ring system which is saturated or partially unsaturated and optionally have additional heteroatoms selected from O, N or S;
wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, —(CR$^a$R$^b$)$_n$COOR$^7$, —(CR$^a$R$^b$)$_n$NR$^7$R$^8$, —(CR$^a$R$^b$)$_n$C(O)NR$^7$R$^8$, —S(O)$_p$R$^7$ or —SO$_3$H.;

$R^2$ and $R^3$ are independently selected from halo, hydroxyl, cyano, $C_{1-6}$alkyl, $C_{2-6}$alkenyl, $C_{2-6}$alkynyl, haloalkyl, perhaloalkyl, cycloalkyl, cycloalkenyl, cycloalkylalkyl, aryl, and arylalkyl;

$R^6$ is selected from hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally have additional heteroatoms selected from O, N or S, said ring system is further optionally substituted with 1 to 4 substituents independently selected from halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, or heteroarylalkyl;

p=0-2;
n=0-4

According to another embodiment, the present disclosure relates to compounds of formula (I) or its tautomers, polymorphs, stereoisomers, prodrugs, solvate or a pharmaceutically acceptable salts thereof, wherein, U, V and W are independently selected from CR' and CR'R";
G is CR';

R' and R" are independently selected from the group consisting of hydrogen, alkyl, haloalkyl, alkoxy, carboxy, hydroxyl or cyano;

T is selected from cyclohexenyl, phenyl, pyridyl, or tetrahydropyridinyl;

Y is —C(O)—

$X^1$, $X^2$ and $X^3$ are each independently $CR^7$;

Z is —C(O)—;

$R^1$, $R^4$ and $R^5$ are independently selected from hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(R^7R^8)_nNR^7R^8$, —$C(R^7R^8)_nCO(R^7)$ and —$S(O)_pC(R^7R^8)_nC(O)OR^7$;

wherein each substituent is unsubstituted or substituted with 1, 2, or 3 substituents independently selected from alkyl, halogen, haloalkyl, perhaloalkyl, haloalkoxy, perhaloalkoxy, cyano, alkoxy, —$(CR^aR^b)_nCOOR^7$, —$(CR^aR^b)_nNR^7R^8$, —$(CR^aR^b)_nC(O)NR^7R^8$, —$S(O)_pR^7$ or —$SO_3H$.;

$R^2$ and $R^3$ are independently selected from halo, hydroxyl, cyano, $C_{1-6}$ alkylhaloalkyl, or perhaloalkyl, $R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, p=0-2;

n=0-4

According to an embodiment, the present disclosure relates to a process for the preparation of a compound of formula (I), their stereoisomers, tautomers, prodrugs, pharmaceutically acceptable salts, polymorphs and solvates.

According to another embodiment, the present disclosure provide a process for the preparation of a compound of formula (I), their stereoisomers, tautomers, prodrugs, pharmaceutically acceptable salts, polymorphs and solvates by following synthetic routes as outlined in the Schemes below.

Scheme 1: Preparation of compounds of formula (Ia):

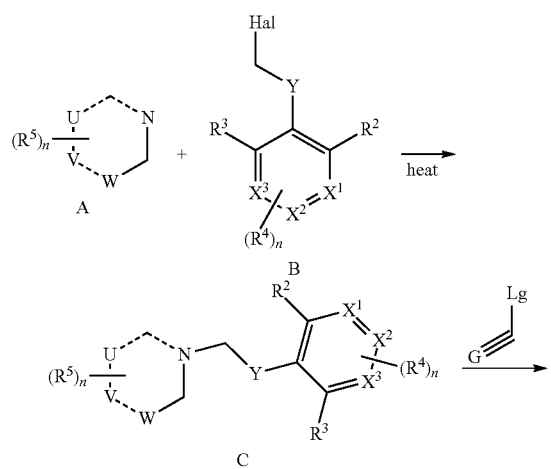

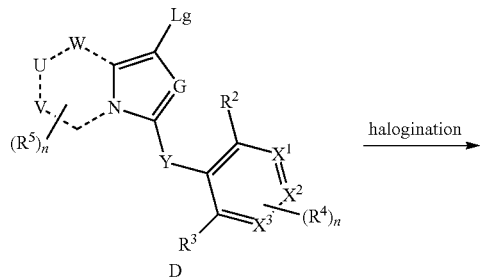

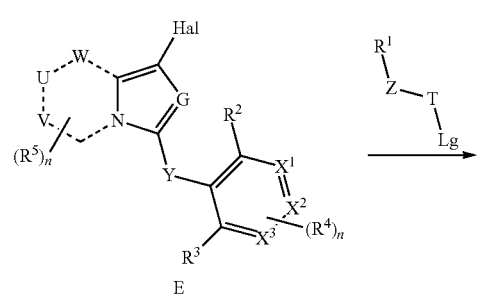

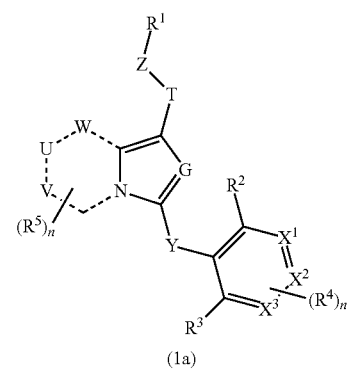

Lg = F, Cl, Br, I, B(OH)$_2$, B(alkyl)$_2$, OH, OMs, OTs, COOH

Scheme 1: Illustrates a method towards the preparation of compounds of formula Ia.

As exemplified in scheme above, compound of formula A and B wherein $X^1$, $X^2$, $X^3$, G, $R^2$, $R^3$, $R^4$, $R^5$, U, V, W, X and Y are defined herein above wherein Hal is any halogen group, which are available commercially or can be prepared by well known methods in the art, may be converted to compounds of formula C by a heating in presence or absence of solvent and react with alkynes, alkenes or any dipolarophile generated in situ produce the cyclized product D. Halogination with appropriate halogenating agent such as NBS or liq. Br$_2$ in acetic acid or liq. Br$_2$ or NCS, pyridine tribromide or sodium bromite transformed to compounds of formula E. Subsequent nucleophilic aromatic substitution or metal mediated N-arylation (Buchwald-Hartwig Cross Coupling reaction), or metal mediated coupling reaction [palladium acetate Pd(OAc)$_2$, copper acetate (Cu(OAc)$_2$), copper bromide (CuBr), nickel chloride (NiCl$_2$.6H$_2$O)] led to the formation of the final compound formula Ia.

Scheme 2: Preparation of compounds of formula (Ib):

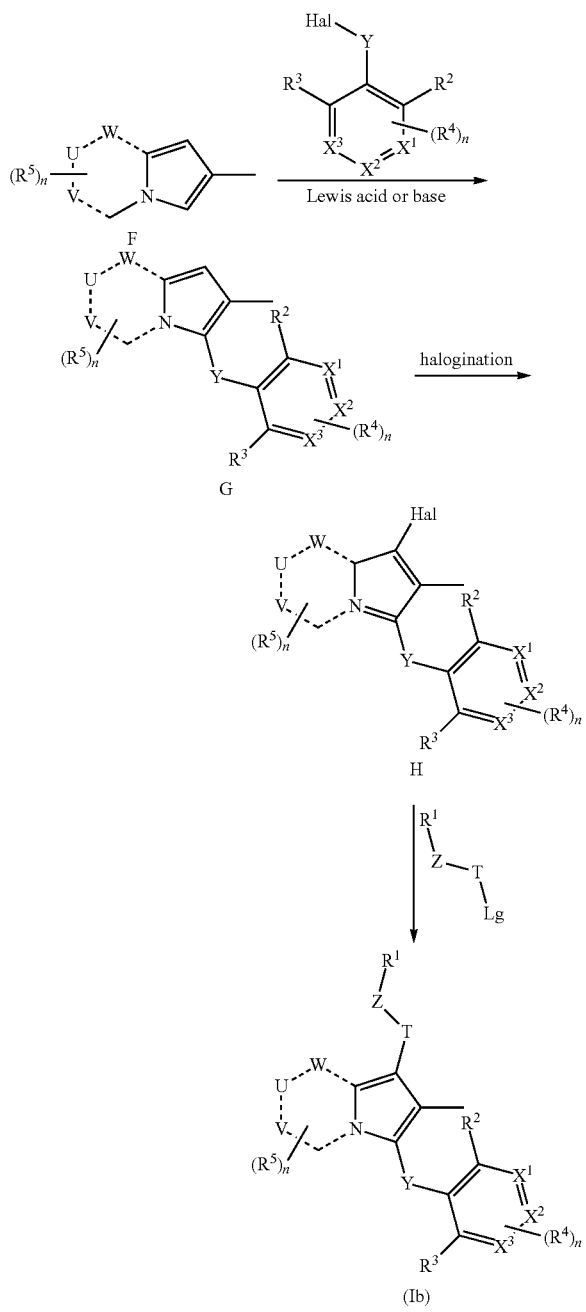

Lg = F, Cl, Br, I, B(OH)$_2$, B(alkyl)$_2$, OH, OMs, OTs

Scheme 2: illustrates a method towards the preparation of compounds of formula Ib.

As exemplified in scheme above, compound of formula F, wherein X$^1$, X$^2$, X$^3$, R$^2$, R$^3$, R$^4$, R$^5$, U, V, W, X and Y are defined herein above wherein Hal is any halogen group, which are available commercially or can be prepared by well known methods in the art, may be converted to compounds of formula G by alkyl lithium ("BuLi, $^t$BuLi, SecBuLi) or organic bases (Et$_3$N, diisopropyl amine etc.) mediated acylation, sulfenylation, benzylation reaction, benzoylation with respective acid chloride, aryl halide or aryl thiol. Halogination with appropriate halogenating agent such as NBS or liq. Br$_2$ in acetic acid or liq. Br$_2$ or NCS, pyridine tribromide or sodium bromite transformed to compounds of formula H. Subsequent nucleophilic aromatic substitution or metal mediated N-arylation (Buchwald-Hartwig Cross Coupling reaction), or metal mediated coupling reaction [palladium acetate Pd(OAc)$_2$, copper acetate (Cu(OAc)$_2$), copper bromide (CuBr), nickel chloride (NiCl$_2$.6H$_2$O)] led to the formation of the final compound formula 1b.

Wherever desired or necessary, in any of the above mentioned processes, any of the compounds of formula (I) may be converted into a pharmaceutically acceptable salt or vice versa or converting one salt form into another pharmaceutically acceptable salt form.

According to another embodiment the present invention provides co-crystals comprising a compound of formula (I) wherein compounds of formula (I) that contain groups capable of acting as donors and/or acceptors for hydrogen bonds may be capable of forming co-crystals with suitable co-crystal formers. These co-crystals may be prepared from compounds of Formula (I) by known co-crystal forming procedures. Such procedures include grinding, heating, co-subliming, co-melting, or contacting in solution compounds of formula (I) with the co-crystal former under crystallization conditions and isolating co-crystals thereby formed.

According to another embodiment the present invention provides pharmaceutical composition comprising, as an active ingredient, at least one compound of formula (I) or its tautomers, polymorphs, stereoisomers, prodrugs, solvate or a pharmaceutically acceptable salts thereof, together with one or more pharmaceutically acceptable carriers or excipients.

According to another embodiment compositions can be prepared by mixing one or more compounds described herein, or pharmaceutically acceptable salts or tautomers thereof, with pharmaceutically acceptable carriers or the like, to treat or ameliorate a variety of RORγ related conditions. The pharmaceutical compositions of the present disclosure can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, transmucosal administration, rectal administration, topical administration or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

According to another embodiment compounds of Formula (I) of the invention can be used alone or in combination with one or more additional therapeutically active agent.

In one embodiment, the invention provides methods of treating a RORγ mediated disease, disorder or syndrome in a subject comprising administering an effective amount of a compound of formula (I).

In another embodiment, the invention provides methods of treating a RORγ mediated disease, disorder or syndrome in a subject comprising administering an effective amount of a compound of formula (I) wherein the disease is an inflammatory or autoimmune disease.

In another embodiment, the invention provides the method of treating a RORγ mediated disease, disorder or syndrome in a subject comprising administering an effective amount of a compound of formula (I) wherein the disease, disorder, syndrome or condition is rheumatoid arthritis, psoriasis, systemic lupus erythromatosis, lupus nephritis, scleroderma, chronic obstructive pulmonary disease (COPD), asthma, allergic rhinitis, allergic eczema, multiple sclerosis, juvenile rheumatoid arthritis, juvenile idiopathic arthritis, type I diabetes, inflammatory bowel disease, graft versus host disease, psoriatic arthritis, reactive arthritis, ankylosing spondylitis, Crohn's disease, ulcerative colitis, uveitis, non-radio graphic spondyloarthropathy, chronic pain, acute pain, inflammatory pain, arthritic pain, neuropathic pain, post-operative pain, surgical pain, visceral pain, dental pain, premenstrual pain, central pain, cancer pain, pain due to burns, migraine or cluster headaches, nerve injury, neuritis, neuralgias, poisoning, ischemic injury, interstitial cystitis, viral, parasitic or bacterial infection, post-traumatic injury, or pain associated with irritable bowel syndrome.

In another embodiment, the invention provide the method of treating a RORγ mediated disease, disorder or syndrome in a subject comprising administering an effective amount of a compound of formula (I) wherein the disease, disorder, syndrome or condition is selected from the group consisting of chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease.

EXAMPLES

The disclosure is further illustrated by the following examples which in no way should be construed as being further limiting. One skilled in the art will readily appreciate that the specific methods and results described are merely illustrative.

Synthesis INT-1-III: Phenacyl Bromides

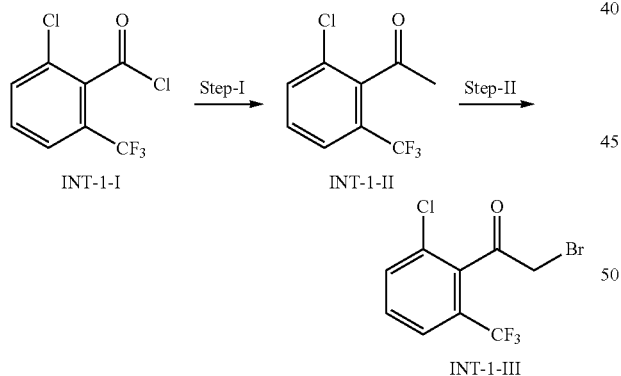

Step-I: INT-1-II: Aryl Methyl Ketones

The aryl methyl ketones are either synthesized described in literature (Vicha, Robert et. al., *Tetrahedron* 2005, 61, 83-88 and WO2006094840) or purchased from commercial source.

Step-II: INT-1-III: General Procedure for the Preparation of Phenacyl Bromides

To a cold solution of aryl methyl ketone INT-1-II (10 mmol) in chloroform (20 mL) was slowly added a solution of bromine (0.51 mL, 10 mmol) in chloroform (20 mL). After completion of the reaction (monitored by LCMS), the mixture was extracted with DCM. The combined extracts were washed with water and dried over anhydrous sodium sulfate. Solvents were evaporated under vacuum. Purification by flash column chromatography (silica gel, hexane/EtOAc) afforded pure phenacyl bromide (yield: 90-98%). LCMS: m/z 302.0 (M+1)$^+$. $^1$H NMR (DMSO-d$_6$, 400 MHz) δ 4.82 (s, 3H), 7.77 (dt, J=1.2, 8.0 Hz, 1H), 7.90 (d, J=8.0 Hz, 1H), 7.95 (d, J=8.0 Hz, 1H).

Synthesis A-2: 4-[3-[2-chloro-6-(trifluoromethyl)benzoyl]indolizin-1-yl]benzoic acid

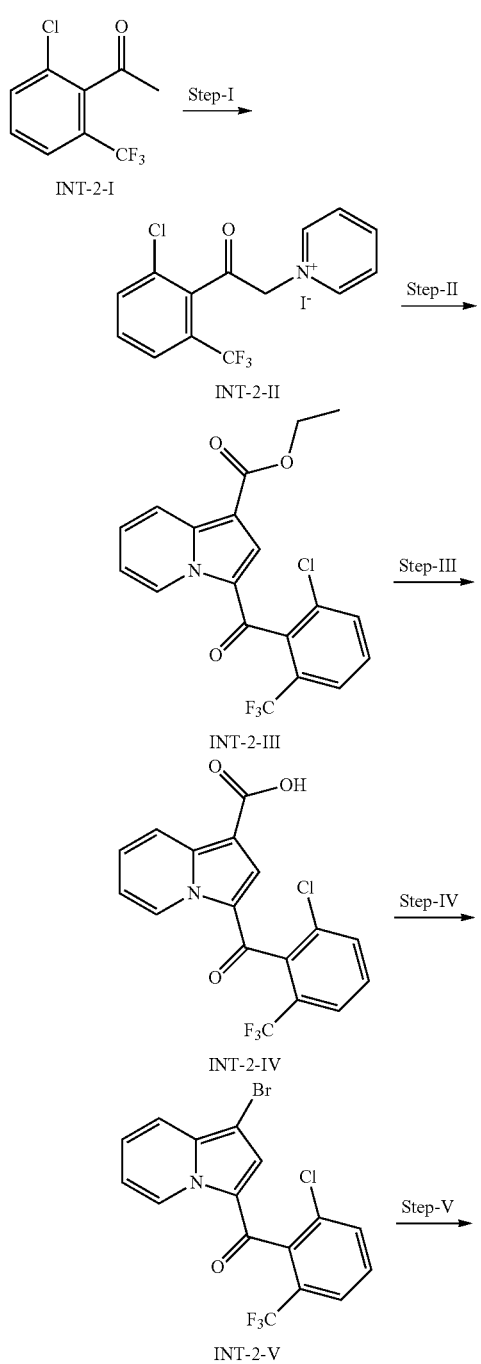

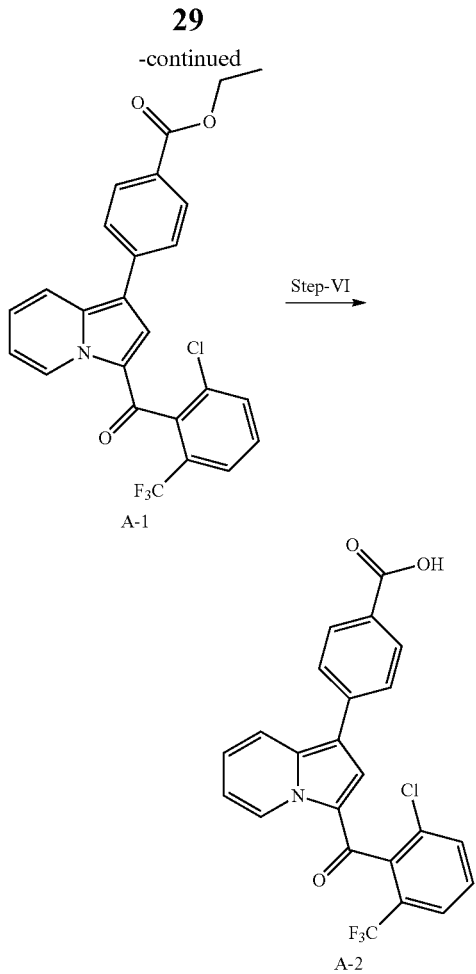

Step-I: INT-2II: 1-[2-chloro-6-(trifluoromethyl)phenyl]-2-pyridin-1-ium-1-yl-ethanone iodide A solution of 1-[2-chloro-6-(trifluoromethyl)phenyl]ethanone (0.8 g, 3.6 mmol) and iodine (1.01 g, 3.6 mmol) in pyridine (3 mL) was refluxed overnight. The reaction mixture was cooled to room temperature, inducing the precipitation of a solid which was filtered off and washed with diethyl ether (3×10 mL). The remaining solid was then stirred overnight in diethyl ether (30 mL). After filtration, the deep brown solid INT-2-II was isolated as crude product (1.4 g). The residue was used in the next step without any further purification.

Step-II: INT-2-III: ethyl 3-[2-chloro-6-(trifluoromethyl)benzoyl]indolizine-1-carboxylate A solution of 1-[2-chloro-6-(trifluoromethyl)phenyl]-2-pyridin-1-ium-1-yl-ethanone iodide (1.4 g, 4.6 mmol) in triethyl amine (0.7 ml, 5.5 mmol) stirred for 10 min at room temperature and ethyl propiolate (0.7 ml, 6.9 mmol) was added. The stirring was continued for additional 1 h at room temperature (monitored by TLC). The solvent was removed to give a solid, which was purified by on combifalsh system with a gradient of 10 to 30% ethyl acetate-hexanes to obtain the desired product (0.300 g, 17%). LCMS: m/z 396 (M+1)$^+$. $^1$H NMR (DMSO-d$_6$, 400 MHz) δ 1.29 (t, J=6.8 Hz, 3H), 4.27 (q, J=6.8 Hz, 2H), 7.30 (s, 1H), 7.45 (t, J=7.2 Hz, 1H), 7.76-7.84 (m, 2H), 7.94 (d, J=8.0 Hz, 1H), 7.99 (d, J=8.4 Hz, 1H), 8.36 (t, J=8.8 Hz, 1H), 9.89 (d, J=8.0 Hz, 1H).

Step-III: INT-2-IV: 3-[2-chloro-6-(trifluoromethyl)benzoyl]indolizine-1-carboxylic acid Ethyl 3-[2-chloro-6-(trifluoromethyl)benzoyl]indolizine-1-carboxylate (1.2 g) and NaOH (0.4 g) were dissolved in a mixture of EtOH (10 ml), water (5 ml) and THF (10 ml) and the reaction mixture stirred for 48 h at room temperature. Once the reaction was complete (monitored by TLC), the reaction mixture was evaporated to dryness, diluted with water (5 ml). The resulting solution was extracted with EtOAc (3×10 ml), and the combined organic phases extracted with 1M aqueous NaOH (2×10 ml). The combined aqueous extracts were acidified with 1M HCl at 0° C. to pH 3-4. The precipitated solid was collected by filtration, washed with water (10 ml), and dried in a vacuum oven. The title compound was obtained as pale yellow solid (0.750 g, 68%). LCMS: m/z 368 (M+1)$^+$. $^1$H NMR (DMSO-d$_6$, 400 MHz) δ 7.27 (s, 1H), 7.45 (t, J=7.2 Hz, 1H), 7.76-7.84 (m, 2H), 7.94 (d, J=8.0 Hz, 1H), 7.99 (d, J=8.4 Hz, 1H), 8.36 (t, J=8.8 Hz, 1H), 9.88 (d, J=8.0 Hz, 1H), 12.85 (s, 1H)

Step-IV: INT-2-V: (1-bromoindolizin-3-yl)-[2-chloro-6-(trifluoromethyl)phenyl]methanone To a solution of 3-[2-chloro-6-(trifluoromethyl)benzoyl]indolizine-1-carboxylic acid (0.75 g, 2.0 mmol) in DMF (3 mL), NaHCO$_3$ (0.52 g. 6.0 minor) and then NBS (0.39 g, 2.2 mmol) was added portion wise over 10 min at 0° C. The resulting mixture was stirred additional 30 min at room temperature. The reaction mixture was diluted with ice cooled water (10 mL) to get yellow precipitate. The precipitated was collected by filtration, washed with water (10 ml), and dried in a vacuum to obtain the title compound (0.750 g, 89%). The residue was used in the next step without any further purification.
LCMS: m/z 402.1 (M+1)$^+$. $^1$H NMR (DMSO-d$_6$, 400 MHz) δ 7.23 (s, 1H), 7.30-7.35(m, 1H), 7.45-7.61 (m, 1H), 7.73-7.79 (m, 2H); 7.90 (d, J=8.0 Hz, 1H), 7.94 (d, J=8.4 Hz, 1H), 9.84 (d, J=8.0 Hz, 1H).

Step-V: A-1: Ethyl 4-[3-[2-chloro-6-(trifluoromethyl)benzoyl]indolizin-1-yl]benzoate 1,1'-Bis(diphenylphosphino)ferrocene-palladium(II)dichloride dichloromethane complex (0.019 g, 0.023 mmol) was added to a degassed solution of (1-bromoindolizin-3-yl)-[2-chloro-6-(trifluoromethyl)phenyl]methanone (0.1 g, 0.23 mmol), (4-ethoxycarbonylphenyl)boronic acid (0.055 g, 0.28 mmol) and potassium carbonate (0.095 g, 0.69 mmol) in 1 ml of water and dioxane (3 mL) under an inert, argon atmosphere. The reaction medium was heated at 110° C. for 15 min in microwave. The reaction was acidified with a 1N aqueous solution of hydrochloric acid and extracted with dichloromethane. The organic phase is washed with water, dried over sodium sulphate, filtered and concentrated under reduced pressure. The residue was purified on combifalsh system with a gradient of 10 to 30% ethyl acetate-hexanes to obtain the desired product A-1 (0.060 g, 54%). LCMS: m/z 472.2 (M+1)$^+$. $^1$H NMR (DMSO-d$_6$, 400 MHz) δ 1.33 (t, J=7.2 Hz, 3H), 4.33 (q, J=7.2 Hz, 2H), 7.33-7.36 (m, 1H), 7.38 (s, 1H), 7.58-7.62 (m, 1H), 7.74-7.81 (m, 3H), 7.91-7.99 (m, 4H), 8.15 (d, J=9.2 Hz, 1H), 9.93 (d, J=7.6 Hz, 1H).

Step-VI: A-2: 4-[3-[2-chloro-6-(trifluoromethyl)benzoyl]indolizin-1-yl]benzoic acid A solution of methyl 4-[3-[2-chloro-6-(trifluoromethyl)benzoyl] indolizin-1-yl] benzoate (0.05 g, 0.2 mmol) in a mixture of THF:EtOH:H$_2$O (4:4:1 mL) was added LiOH.H$_2$O (0.014 g, 0.32 mmol) and the mixture was stirred for 16 h at room temperature. After completion of the reaction, the solvents were removed under reduced pressure. The crude product was dissolved in the water and acidified with 1N HCl solution up to pH=3. Obtained solid was filtered and dried to afford the title compound A-2 (0.020 g, 42%).

LCMS: m/z 444.2 (M+1)$^+$. $^1$H NMR (DMSO-d$_6$, 400 MHz) δ 7.32-7.37 (m, 2H), 7.58-7.62 (m, 1H), 7.77-7.81 (m, 3H), 7.91-7.99 (m, 4H), 8.15 (d, J=9.2 Hz, 1H), 9.93 (d, J=7.2 Hz, 1H), 12.96 (s, 1H).

Following compounds were prepared from its corresponding intermediate using the same sequence of procedures as used for preparation of Example A-2 from INT-2-V.

| No | IUPAC name | Characterization | INT used |
|---|---|---|---|
| A-3 | 4-[3-(2,6-dichlorobenzoyl)indolizin-1-yl]-3-fluoro-benzoic acid | LCMS: m/z 428 (M + 1)$^+$. $^1$H NMR (DMSO-d$_6$, 400 MHz) δ 7.26 (s, 1H); 7.36 (t, 1H, J = 6.8 Hz); 7.56-7.64 (m, 4H); 7.72-7.77 (m, 2H); 7.81-7.84 (m, 1H); 7.99 (d, J = 9.2 Hz, 1H); 9.94 (d, J = 7.2 Hz, 1H); 13.25 (bs, 1H). | INT-2-V |
| A-4 | methyl 4-[3-(2,6-dichlorobenzoyl)indolizin-1-yl]-3-fluoro-benzoate | LCMS: m/z 442 (M + 1)$^+$. $^1$H NMR (DMSO-d$_6$, 400 MHz) δ 3.88 (s, 3H); 7.28 (bs, 1H); 7.35-7.38 (m, 1H); 7.54-7.64 (m, 4H); 7.76-7.78 (m, 2H); 7.84-7.90 (m, 2H); 9.92 (d, 1H, J = 6.8 hz). | INT-2-V |
| A-5 | methyl 4-[3-(2,6-difluorobenzoyl)indolizin-1-yl]-3-fluoro-benzoate | LCMS: m/z 409 (M + 1)$^+$. $^1$H NMR (DMSO-d$_6$, 400 MHz) δ 3.88 (s, 3H); 7.31-7.27 (m, 2H); 7.35-7.38 (m, 2H); 7.45 (s, 1H); 7.59-7.66 (m, 2H); 7.77-7.89 (m, 4H). | INT-2-V |
| A-6 | ethyl 4-[3-(2,6-dichlorobenzoyl)indolizin-1-yl]benzoate | LCMS: m/z 438 (M + 1)$^+$. $^1$H NMR (DMSO-d$_6$, 400 MHz) δ 1.33 (t, 3H, J = 6.8 Hz); 4.33 (q, 2H, J = 6.8 Hz); 7.35 (t, 1H, J = 7.2 Hz); 7.39 (s, 1H); 7.55-7.64 (m, 4H); 7.77 (d, J = 8.4 Hz, 2H); 7.99 (d, J = 8 Hz, 2H); 8.15 (d, J = 8.8 Hz, 1H); 9.96 (d, J = 7.2 Hz, 1H). | INT-2-V |
| A-7 | methyl 4-[3-(2,6-dichlorobenzoyl)indolizin-1-yl]-3,5-difluoro-benzoate | LCMS: m/z 460 (M + 1)$^+$. $^1$H NMR (DMSO-d$_6$, 400 MHz) δ 3.89 (s, 3H); 7.64-7.72 (m, 3H); 7.54-7.63 (m, 4H); 7.37 (t, 1H J = 6.8 Hz); 7.26 (s, 1H); 9.3 (d, 1H, J = 6.8 Hz). | INT-2-V |
| A-8 | 4-[3-(2,6-dichlorobenzoyl)indolizin-1-yl]benzoic acid | LCMS: m/z 410 (M + 1)$^+$. $^1$H NMR (DMSO-d$_6$, 400 MHz) δ 7.34 (t, 1H, J = 7.2 Hz); 7.38 (s, 1H); 7.55-7.62 (m, 4H); 7.75 (d, J = 8.8 Hz, 2H); 7.98 (d, J = 8.4 Hz, 2H); 8.15 (d, J = 9.2 Hz, 1H); 9.96 (d, J = 7.2 Hz, 1H); 12.95 (bs, 1H). | INT-2-V |
| A-9 | 4-[3-(2,6-dichlorobenzoyl)indolizin-1-yl]-3,5-difluoro-benzoic acid | LCMS: m/z 446 (M + 1)$^+$. $^1$H NMR (DMSO-d$_6$, 400 MHz) δ 7.25 (s, 1H); 7.36 (t, 1H, J = 7.2 Hz); 7.54-7.68 (m, 6H); 9.92 (d, 1H, J = 6.8 Hz); 13.7 (bs, 1H). | INT-2-V |
| A-10 | 5-[3-(2,6-dichlorobenzoyl)indolizin-1-yl]pyridine-2-carboxylic acid | LCMS: m/z 411.2 (M + 1)$^+$. $^1$H NMR (DMSO-d$_6$, 400 MHz) δ 7.36 (t, J = 6.8 Hz, 1H), 7.55-7.64 (m, 5H), 8.03-8.06 (m, 1H), 8.16-8.21 (m, 2H), 8.92 (bs, 1H) 9.97 (d, J = 6.8 Hz, 1H), 13.01 (s, 1H) | INT-2-V |
| A-11 | methyl 4-[3-[2-chloro-6-(trifluoromethyl)benzoyl]indolizin-1-yl]-3-fluoro-benzoate | LCMS: m/z 476.2 (M + 1)$^+$. $^1$H NMR (DMSO-d$_6$, 400 MHz) δ 3.88 (s, 3H), 7.25 (s, 1H), 7.34-7.37 (m, 1H), 7.58-7.62 (m, 1H), 7.74-7.80 (m, 3H), 7.83-7.84 (m, 1H), 7.85-7.97 (m, 3H), 9.92 (d, J = 6.8 Hz, 1H) | INT-2-V |
| A-12 | 4-[3-[2-chloro-6-(trifluoromethyl)benzoyl]indolizin-1-yl]-3-fluoro-benzoic acid | LCMS: m/z 462.2 (M + 1)$^+$. $^1$H NMR (DMSO-d$_6$, 400 MHz) δ 7.24 (s, 1H), 7.36 (t, J = 6.8 Hz, 1H), 7.59 (t, J = 8.0 Hz, 1H), 7.70-7.83 (m, 4H), 7.88-7.97 (m, 3H), 9.92 (d, J = 6.8 Hz, 1H), 13.23 (s, 1H) | INT-2-V |
| A-13 | methyl 4-[3-(2-chloro-6-methyl-benzoyl)indolizin-1-yl]-3-fluoro-benzoate | LCMS: m/z 422.2 (M + 1)$^+$. $^1$H NMR (DMSO-d$_6$, 400 MHz) δ 2.22 (s, 3H), 3.88 (s, 3H), 7.15 (s, 1H), 7.32-7.36 (m, 2H), 7.42-7.43 (m, 2H), 7.57 (t, J = 8.0 Hz, 1H), 7.76-7.80 (m, 2H), 7.83-7.89 (m, 2H), 9.99 (d, J = 6.8 Hz, 1H) | INT-2-V |

| No | IUPAC name | Characterization | INT used |
|---|---|---|---|
| A-14 | ethyl 4-[3-(2-chloro-6-methyl-benzoyl)indolizin-1-yl]benzoate | LCMS: m/z 418.2 (M + 1)$^+$. $^1$H NMR (DMSO-d$_6$, 400 MHz) δ 1.31 (t, J = 7.2 Hz, 3H), 2.20 (s, 3H), 4.30 (q, J = 7.2 Hz, 2H), 7.20 (s, 1H), 7.29-7.34 (m, 2H), 7.38-7.41 (m, 2H), 7.53-7.57 (m, 1H), 7.73 (d, J = 8.8 Hz, 2H), 7.96 (d, J = 8.4 Hz, 2H), 8.11 (d, J = 8.8 Hz, 1H), 9.98 (d, J = 7.2 Hz, 1H) | INT-2-V |
| A-15 | 4-[3-(2-chloro-6-methyl-benzoyl)indolizin-1-yl]-3-fluoro-benzoic acid | LCMS: m/z 408.2 (M + 1)$^+$. $^1$H NMR (DMSO-d$_6$, 400 MHz) δ 2.22 (s, 3H), 7.14 (s, 1H), 7.32-7.37 (m, 2H), 7.40-7.45 (m, 2H), 7.54-7.58 (m, 1H), 7.72-7.76 (m, 2H), 7.81-7.84 (m, 1H), 7.88 (d, J = 8.4 Hz, 1H), 9.99 (d, J = 6.8 Hz, 1H), 13.23 (s, 1H) | INT-2-V |
| A-16 | 4-[3-(2-chloro-6-methyl-benzoyl)indolizin-1-yl]benzoic acid | LCMS: m/z 390.2 (M + 1)$^+$. $^1$H NMR (DMSO-d$_6$, 400 MHz) δ 2.23 (s, 3H), 7.21 (s, 1H), 7.29-7.36 (m, 2H), 7.40-7.43 (m, 2H), 7.54-7.58 (m, 1H), 7.73 (d, J = 8.4 Hz, 2H), 7.98 (d, J = 8.4 Hz, 2H), 8.14 (d, J = 9.2 Hz, 1H), 10.00 (d, J = 7.2 Hz, 1H), 12.96 (s, 1H) | INT-2-V |
| A-17 | methyl 4-[3-(2,6-dichloro-3-fluoro-benzoyl)indolizin-1-yl]-3-fluoro-benzoate | LCMS: m/z 461.0 (M + 1)$^+$. $^1$H NMR (DMSO-d$_6$, 400 MHz) δ 3.93 (s, 3H), 7.36-7.39 (m, 1H), 7.45-7.47 (m, 1H), 7.59-7.71 (m, 3H), 7.75-7.88 (m, 4H), 9.93 (d, J = 6.8 Hz, 1H) | INT-2-V |
| A-18 | 4-[3-(2,6-dichloro-3-fluoro-benzoyl)indolizin-1-yl]-3-fluoro-benzoic acid | LCMS: m/z 446 (M + 1)$^+$. $^1$H NMR (DMSO-d$_6$, 400 MHz) δ 7.35-7.39 (m, 1H), 7.43-7.45 (m, 1H), 7.62-7.76 (m, 5H), 7.82-7.83 (m, 1H), 7.84-7.89 (m, 1H), 9.93 (d, J = 6.8 Hz, 1H), 13.21 (s, 1H) | INT-2-V |
| A-19 | 4-[3-(2,6-dichloro-3-fluoro-benzoyl)indolizin-1-yl]benzoic acid | LCMS: m/z 427.9 (M + 1)$^+$. $^1$H NMR (DMSO-d$_6$, 400 MHz) δ 7.29-7.33 (m, 1H), 7.40 (s, 1H), 7.48 (d, J = 8.0 Hz, 2H), 7.49-7.59 (m, 1H), 7.61-7.69 (m, 2H), 7.88 (d, J = 8.0 Hz, 2H), 8.10 (d, J = 4.8 Hz, 1H), 9.92 (d, J = 6.8 Hz, 1H), 13.01 (s, 1H) | INT-2-V |
| A-20 | (2,6-dichlorophenyl)-[1-(4-methylsulfonylphenyl)indolizin-3-yl]methanone | LCMS: m/z 453.0 (M + 1)$^+$. $^1$H NMR (DMSO-d$_6$, 400 MHz) δ 3.23 (s, 3H), 7.34-7.40 (m, 1H), 7.45 (s, 1H), 7.55-7.65 (m, 4H), 7.89-7.96 (m, 4H), 8.16 (d, J = 8.8 Hz, 1H), 9.96 (d, J = 6.8 Hz, 1H) | INT-2-V |
| A-21 | ethyl 4-[3-(2,6-dichlorobenzoyl)-8-fluoro-indolizin-1-yl]benzoate | LCMS: m/z 456.1 (M + 1)$^+$. $^1$H NMR (DMSO-d$_6$, 400 MHz) δ 1.33 (t, J = 6.8 Hz, 3H), 4.32 (q, J = 6.8 Hz, 2H), 7.28-7.33 (m, 2H), 7.43-7.47 (s, 1H), 7.57-7.66 (m, 5H), 7.95 (d, J = 8.4 Hz, 2H), 9.78 (d, J = 8.8 Hz, 1H) | INT-2-V |
| A-22 | methyl 4-[3-(2,6-dichlorobenzoyl)-8-fluoro-indolizin-1-yl]-3-fluoro-benzoate | LCMS: m/z 460.1 (M + 1)$^+$. $^1$H NMR (DMSO-d$_6$, 400 MHz) δ 3.88 (s, 3H), 7.28 (s, 1H), 7.29-7.34 (m, 1H), 7.45-7.48 (m, 1H), 7.55-7.57 (m, 1H), 7.58-7.67 (s, 3H), 7.74-7.77 (m, 1H), 7.80-7.82 (m, 1H), 9.76 (d, J = 6.8 Hz, 1H) | INT-2-V |
| A-23 | 4-[3-(2,6-dichlorobenzoyl)-8-fluoro-indolizin-1-yl]benzoic acid | LCMS: m/z 428.1 (M + 1)$^+$. $^1$H NMR (DMSO-d$_6$, 400 MHz) δ 7.28-7.33 (m, 2H), 7.42-7.47 (m, 1H), 7.55-7.65 (m, 5H), 7.92-7.95 (m, 2H), 9.78 (d, J = 6.8 Hz, 1H), 12.98 (s, 1H) | INT-2-V |
| A-24 | ethyl 4-[3-(2-chloro-6-fluoro-benzoyl)indolizin-1-yl]benzoate | LCMS: m/z 422.1 (M + 1)$^+$. $^1$H NMR (DMSO-d$_6$, 400 MHz) δ 7.35 (t, J = 6.4 Hz, 1H), 7.40-7.51 (m, 3H), 7.59-7.63 (m, 2H), 7.78 (d, J = 8.0 Hz, 2H), 7.79 (d, J = 8.4 Hz, 2H), 8.15 (d, J = 9.6 Hz, 1H), 9.96 (d, J = 6.8 Hz, 1H) | INT-2-V |
| A-25 | ethyl 4-[3-(2-chloro-6-fluoro-benzoyl)indolizin-1-yl]-3-fluoro-benzoate | LCMS: m/z 422.1 (M + 1)$^+$. $^1$H NMR (DMSO-d$_6$, 400 MHz) δ 1.33 (t, J = 7.2 Hz, 3H), 4.35 (q, J = 7.2 Hz, 2H), 7.35-7.51 (m, 4H), 7.59-7.64 (m, 2H), | INT-2-V |

| No | IUPAC name | Characterization | INT used |
|---|---|---|---|
| | | 7.76-7.89 (m, 4H), 9.94 (d, J = 6.8 Hz, 1H) | |
| A-26 | 4-[3-(2,6-dichlorobenzoyl)-6-fluoro-indolizin-1-yl]benzoic acid | LCMS: m/z 428 (M + 1)+. 1H NMR (DMSO-d6, 400 MHz) δ 7.44 (s, 1H), 7.56-7.71 (m, 4H), 7.75-7.77 (m, 2H), 7.97-7.99 (m, 2H), 8.19-8.23 (m, 1H), 9.95-9.97 (m, 1H), 12.99 (s, 1H) | INT-2-V |
| A-27 | 4-[3-(2-chloro-6-fluoro-benzoyl)indolizin-1-yl]-3-fluoro-benzoic acid | LCMS: m/z 412.1 (M + 1)+. 1H NMR (DMSO-d6, 400 MHz) δ 7.35-7.45 (m, 3H), 7.49-7.51 (m, 1H), 7.59-7.64 (m, 2H), 7.73-7.78 (m, 2H), 7.82-7.85 (m, 1H), 7.88-7.90 (m, 1H), 9.94 (d, J = 6.8 Hz, 1H), 13.22 (s, 1H) | INT-2-V |
| A-28 | 4-[3-(2-chloro-6-fluoro-benzoyl)indolizin-1-yl]benzoic acid | LCMS: m/z 405.1 (M + 1)+. 1H NMR (DMSO-d6, 400 MHz) δ 7.33-7.34 (m, 1H), 7.35-7.44 (m, 1H), 7.48-7.51 (m, 1H), 7.59-7.65 (m, 2H), 7.75-7.77 (m, 2H), 7.97-8.00 (m, 2H), 8.15-8.17 (m, 1H), 9.99 (d, J = 6.8 Hz, 1H), 12.90 (s, 1H) | INT-2-V |
| A-29 | 4-[3-(2-chloro-6-cyclopropyl-benzoyl)indolizin-1-yl]-3-fluoro-benzoic acid | LCMS: m/z 434.1 (M + 1)+. 1H NMR (DMSO-d6, 400 MHz) δ 0.64-0.66 (m, 1H), 0.72-0.74 (m, 2H), 0.83-1.07 (m, 1H), 1.74-1.77 (m, 1H), 6.99-7.02 (m, 1H), 7.15-7.16 (m, 1H), 7.31-7.41 (m, 3H), 7.53-7.57 (m, 1H), 7.71-7.76 (m, 2H), 7.82-7.84 (m, 1H), 7.88-7.90 (m, 1H), 10.00-10.02 (m, 1H), 13.02 (s, 1H) | INT-2-V |
| A-30 | ethyl 4-[3-(2-chloro-6-cyclopropyl-benzoyl)indolizin-1-yl]-3-fluoro-benzoate | LCMS: m/z 462.1 (M + 1)+. 1H NMR (DMSO-d6, 400 MHz) δ 0.74-0.87 (m, 4H), 1.31 (t, J = 6.8 Hz, 3H), 1.35-1.36 (m, 1H), 4.34 (q, J = 6.8 Hz, 2H), 7.00-7.02 (m, 1H), 7.16-7.18 (m, 1H), 7.33-7.43 (m, 3H), 7.55-7.58 (m, 1H), 7.75-7.84 (m, 2H), 7.86-7.89 (m, 2H), 10.00-10.02 (m, 1H), | INT-2-V |
| A-31 | ethyl 4-[3-(2-chloro-6-cyclopropyl-benzoyl)indolizin-1-yl]benzoate | LCMS: m/z 444.1 (M + 1)+. 1H NMR (DMSO-d6, 400 MHz) δ 0.73-0.83 (m, 4H), 1.13 (t, J = 7.2 Hz, 3H), 1.33-1.36 (m, 1H), 4.32 (q, J = 7.2 Hz, 2H), 7.00-7.03 (m, 1H), 7.24 (s, 1H), 7.30-7.34 (m, 1H), 7.36-7.44 (m, 2H), 7.58-7.56 (m, 1H), 7.54-7.73 (m, 2H), 7.98-8.60 (m, 2H), 8.12-8.14 (m, 1H), 10.01-10.03 (m, 1H), | INT-2-V |
| A-32 | ethyl 4-[3-(2-chloro-6-fluoro-benzoyl)-8-fluoro-indolizin-1-yl]benzoate | LCMS: m/z 440.1 (M + 1)+. 1H NMR (DMSO-d6, 400 MHz) δ 1.33 (t, J = 7.2 Hz, 3H), 4.32 (q, J = 7.2 Hz, 2H), 7.29-7.32 (m, 1H), 7.36 (s, 1H), 7.41-7.51 (m, 3H), 7.59-7.67 (m, 3H), 7.95-7.97 (m, 2H), 9.78 (d, J = 6.8 Hz, 1H) | INT-2-V |
| A-33 | ethyl 4-[3-(2-chloro-6-fluoro-benzoyl)-8-fluoro-indolizin-1-yl]-3-fluoro-benzoate | LCMS: m/z 440.1 (M + 1)+. 1H NMR (DMSO-d6, 400 MHz) δ 1.33 (t, J = 7.2 Hz, 3H), 4.34 (q, J = 7.2 Hz, 2H), 7.29-7.33 (m, 1H), 7.34 (s, 1H), 7.40-7.46 (m, 2H), 7.49-7.51 (m, 1H), 7.59-7.69 (m, 2H), 7.73-7.77 (m, 1H), 7.98-7.82 (m, 1H), 9.76 (d, J = 7.2 Hz, 1H) | INT-2-V |
| A-34 | 4-[3-(2-chloro-6-fluoro-benzoyl)-8-fluoro-indolizin-1-yl]benzoic acid | LCMS: m/z 412.1 (M + 1)+. 1H NMR (DMSO-d6, 400 MHz) δ 7.28-7.33 (m, 1H), 7.35 (s, 1H), 7.43-7.51 (m, 3H), 7.59-7.64 (m, 3H), 7.94 (d, J = 8.0 Hz, 2H), 9.77 (d, J = 7.2 Hz, 1H), 12.99 (s, 1H) | INT-2-V |
| A-35 | 4-[3-(2-chloro-6-fluoro-benzoyl)-8-fluoro-indolizin-1-yl]-3-fluoro-benzoic acid | LCMS: m/z 430.1 (M + 1)+. 1H NMR (DMSO-d6, 400 MHz) δ 7.29-7.34 (m, 2H), 7.40-7.51 (m, 3H), 7.59-7.66 (m, 2H), 7.70-7.77 (m, 1H), 7.78-7.80 (m, 1H), 9.76 (d, J = 6.8 Hz, 1H), 13.23 (s, 1H) | INT-2-V |
| A-36 | ethyl 4-[3-(2,6-difluorobenzoyl)indolizin-1-yl]benzoate | LCMS: m/z 405.1 (M + 1)+. 1H NMR (DMSO-d6, 400 MHz) δ 1.33 (t, J = 6.8 Hz, 3H), 4.33 (q, J = 6.8 Hz, 2H), 7.27-7.37 (m, 3H), 7.56 (s, 1H), 7.59-7.67 (m, 2H), 7.79-7.81 (m, 2H), | INT-2-V |

| No | IUPAC name | Characterization | INT used |
|---|---|---|---|
| | | 7.99-8.02 (m, 2H), 8.14-8.16 (m, 1H), 9.95-9.96 (m, 1H) | |
| A-37 | 4-[3-(2,6-difluorobenzoyl)indolizin-1-yl]benzoic acid | LCMS: m/z 405.1 (M + 1)+. $^1$H NMR (DMSO-d$_6$, 400 MHz) δ 7.27-7.36 (m, 3H), 7.55 (s, 1H), 7.59-7.67 (m, 2H), 7.76-7.78 (m, 2H), 7.97-8.00 (m, 2H), 8.15-8.17 (m, 1H), 9.95-9.96 (m, 1H), 12.90 (s, 1H) | INT-2-V |
| A-38 | ethyl 4-[3-(2,6-difluorobenzoyl)indolizin-1-yl]-3-fluoro-benzoate | LCMS: m/z 424.2 (M + 1)+. $^1$H NMR (DMSO-d$_6$, 400 MHz) δ 1.34 (t, J = 6.4 Hz, 3H), 4.35 (q, J = 6.4 Hz, 2H), 7.27-7.32 (m, 2H), 7.35-7.39 (m, 1H), 7.45 (s, 1H), 7.59-7.64 (m, 2H), 7.77-7.81 (m, 2H), 7.84-7.89 (m, 2H), 9.95 (d, J = 6.8 Hz, 1H) | INT-2-V |
| A-39 | 4-[3-(2,6-difluorobenzoyl)indolizin-1-yl]-3-fluoro-benzoic acid | LCMS: m/z 369.1 (M + 1)+. $^1$H NMR (DMSO-d$_6$, 400 MHz) δ 7.26-7.32 (m, 2H), 7.34-7.38 (m, 1H), 7.45 (s, 1H), 7.58-7.66 (m, 2H), 7.67-7.82 (m, 2H), 7.89-7.83 (m, 2H), 9.94 (d, J = 6.8 Hz, 1H), 13.24 (s, 1H) | INT-2-V |
| A-40 | [1-(p-tolyl)indolizin-3-yl]-(2,3,6-trifluorophenyl)methanone | LCMS: m/z 366.1 (M + 1)+. $^1$H NMR (DMSO-d$_6$, 400 MHz) δ 1.34 (t, J = 6.8 Hz, 3H), 4.03 (q, J = 6.8 Hz, 2H), 7.32-7.38 (m, 2H), 7.62-7.66 (m, 1H), 7.69-7.77 (m, 2H), 7.81-7.83 (m, 2H), 8.00-8.02 (m, 2H), 8.16-8.18 (m, 1H), 9.99 (d, J = 8.8 Hz, 1H) | INT-2-V |
| A-41 | ethyl 3-fluoro-4-[3-(2,3,6-trifluorobenzoyl)indolizin-1-yl]benzoate | LCMS: m/z 442.1 (M + 1)+. $^1$H NMR (DMSO-d$_6$, 400 MHz) δ 1.33 (t, J = 7.2 Hz, 3H), 4.30 (q, J = 7.2 Hz, 2H), 7.32-7.40 (m, 2H), 7.61-7.88 (m, 7H), 9.92 (d, J = 6.8 Hz, 1H) | INT-2-V |
| A-42 | 4-[3-(2,3,6-trifluorobenzoyl)indolizin-1-yl]benzoic acid | LCMS: m/z 369.1 (M + 1)+. $^1$H NMR (DMSO-d$_6$, 400 MHz) δ 7.32-7.39 (m, 2H), 7.62-7.66 (m, 1H), 7.70-7.74 (m, 1H), 7.76 (s, 1H), 7.79-7.81 (m, 2H), 7.98-8.01 (m, 2H), 8.16-8.19 (m, 1H), 9.99 (d, J = 6.8 Hz, 1H), 12.99 (s, 1H) | INT-2-V |
| A-43 | 4-[3-(2,6-dichloro-3-fluoro-benzoyl)-8-fluoro-indolizin-1-yl]benzoic acid | LCMS: m/z 446.1 (M + 1)+. $^1$H NMR (DMSO-d$_6$, 400 MHz) δ 7.30-7.34 (m, 1H), 7.44-7.49 (m, 2H), 7.62-7.71 (m, 4H), 7.93-7.96 (m, 2H), 9.72 (d, J = 7.2 Hz, 1H), 13.01 (s, 1H) | INT-2-V |
| A-44 | 3-fluoro-4-[3-(2,3,6-trifluorobenzoyl)indolizin-1-yl]benzoic acid | LCMS: m/z 414.1 (M + 1)+. $^1$H NMR (DMSO-d$_6$, 400 MHz) δ 7.23-7.38 (m, 2H), 7.60-7.64 (m, 2H), 7.69-7.76 (m, 3H), 7.83-7.88 (m, 2H), 9.90 (d, J = 7.2 Hz, 1H), 13.31 (s, 1H) | INT-2-V |
| A-45 | ethyl 4-[3-(2,6-difluorobenzoyl)-8-fluoro-indolizin-1-yl]benzoate | LCMS: m/z 424.1 (M + 1)+. $^1$H NMR (DMSO-d$_6$, 400 MHz) δ 1.33 (t, J = 7.2 Hz, 3H), 4.33 (q, J = 7.2 Hz, 2H), 7.28-7.33 (m, 3H), 7.44-7.49 (m, 2H), 7.65-7.68 (m, 3H), 7.94-7.98 (m, 2H), 9.29 (d, J = 6.8 Hz, 1H) | INT-2-V |
| A-46 | ethyl 4-[3-(2,6-difluorobenzoyl)-8-fluoro-indolizin-1-yl]-3-fluoro-benzoate | LCMS: m/z 442.1 (M + 1)+. $^1$H NMR (DMSO-d$_6$, 400 MHz) δ 1.33 (t, J = 7.2 Hz, 3H), 4.35 (q, J = 7.2 Hz, 2H), 7.28-7.34 (m, 2H), 7.45-7.49 (m, 2H), 7.64-7.69 (m, 2H), 7.75-7.78 (m, 1H), 7.80-7.83 (m, 1H), 9.75 (d, J = 8.8 Hz, 1H) | INT-2-V |
| A-47 | 4-[3-(2,6-difluorobenzoyl)-8-fluoro-indolizin-1-yl]benzoic acid | LCMS: m/z 396.1 (M + 1)+. $^1$H NMR (DMSO-d$_6$, 400 MHz) δ 7.28-7.33 (m, 3H), 7.43-7.48 (m, 2H), 7.62-7.68 (m, 3H), 7.93-7.96 (m, 2H), 9.77 (d, J = 6.8 Hz, 1H), 13.01 (s, 1H) | INT-2-V |
| A-48 | 4-[3-(2,6-difluorobenzoyl)-8-fluoro-indolizin-1-yl]-3-fluoro-benzoic acid | LCMS: m/z 414.1 (M + 1)+. $^1$H NMR (DMSO-d$_6$, 400 MHz) δ 7.28-7.33 (m, 3H), 7.44-7.49 (m, 2H), 7.62-7.69 (m, 2H), 7.72-7.75 (m, 1H), 7.79-7.82 (m, 1H), 9.76 (d, J = 8.8 Hz, 1H), 13.40 (s, 1H) | INT-2-V |
| A-49 | 4-[3-(2,6-dichloro-3-fluoro-benzoyl)-8-fluoro- | LCMS: m/z 464.0 (M + 1)+. $^1$H NMR (DMSO-d$_6$, 400 MHz) δ 7.3-7.32 (m, | INT-2-V |

-continued

| No | IUPAC name | Characterization | INT used |
|---|---|---|---|
| | indolizin-1-yl]-3-fluoro-benzoic acid | 1H), 7.44-7.49 (m, 2H), 7.73-7.76 (m, 4H), 7.78-7.80 (m, 1H), 9.74 (d, J = 6.8 Hz, 1H), 13.40 (s, 1H) | |
| A-50 | 4-[3-(2-bromo-6-chloro-benzoyl)indolizin-1-yl]benzoic acid | LCMS: m/z 454.0 (M + 1)$^+$. $^1$H NMR (DMSO-d$_6$, 400 MHz) δ 7.03 (s, 1H), 7.21 (dt, J = 0.8, 6.8 Hz, 1H) 7.47-7.51 (m, 4H), 7.61-7.80 (m, 3H), 7.81 (d, J = 8.4 Hz, 2H), 9.74 (d, J = 6.8 Hz, 1H), 12.92 (s, 1H) | INT-2- |
| A-51 | 4-[3-(2-chloro-6-fluoro-benzoyl)indolizin-1-yl]benzoic acid | LCMS: m/z 428.1 (M + 1)$^+$. $^1$H NMR (DMSO-d$_6$, 400 MHz) δ 7.33-7.36 (m, 1H), 7.47 (s, 1H), 7.59-7.63 (m, 1H), 7.74-7.84 (m, 5H), 7.97 (d, J = 8.4 Hz, 2H), 8.16 (d, J = 8.8 Hz, 1H), 9.93 (d, J = 7.2 Hz, 1H), 12.96 (s, 1H) | INT-2-V |
| A-52 | 4-[3-(2-bromo-6-chloro-benzoyl)indolizin-1-yl]-3-fluoro-benzoic acid | LCMS: m/z 472.0 (M + 1)$^+$. $^1$H NMR (DMSO-d$_6$, 400 MHz) δ 7.07 (s, 1H), 7.19 (dt, J = 1.2, 7.2 Hz, 1H) 7.37 (t, J = 7.6 Hz, 1H), 7.47-7.51 (m, 2H), 7.58-7.73 (m, 5H), 9.66 (d, J = 6.8 Hz, 1H), 13.28 (s, 1H) | INT-2-V |
| A-53 | 4-[3-(2,6-dibromobenzoyl)indolizin-1-yl]benzoic acid | LCMS: m/z 504 (M + 1)$^+$. $^1$H NMR (DMSO-d$_6$, 400 MHz) δ 7.03 (bs, 1H), 7.21-7.24 (m, 1H), 7.46-7.51 (m, 3H), 7.56-7.63 (m, 3H), 7.75-7.82 (m, 3H), 9.74 (d, J = 7.2 Hz, 1H), 12.95 (s, 1H) | INT-2-V |
| A-54 | tert-butyl 4-[3-(2,6-dichlorobenzoyl)indolizin-1-yl]-3,6-dihydro-2H-pyridine-1-carboxylate | LCMS: m/z 471.1 (M + 1)$^+$. $^1$H NMR (DMSO-d$_6$, 400 MHz) δ 1.42 (s, 9H), 2.40-2.42 (m, 2H), 3.49 (t, J = 4.4 Hz, 2H), 3.98-4.00 (m, 2H), 6.03 (s, 1H), 7.02 (s, 1H), 7.23-7.27 (m, 1H), 7.46-7.48 (m, 1H), 7.49-7.59 (m, 1H), 7.61-7.62 (m, 2H), 8.01-8.05 (m, 1H), 9.89 (d, J = 6.8 Hz, 1H) | INT-2-V |
| A-55 | tert-butyl 5-[3-(2,6-dichloro-3-fluoro-benzoyl)indolizin-1-yl]-3,6-dihydro-2H-pyridine-1-carboxylate | LCMS: m/z 489.1 (M + 1)$^+$. $^1$H NMR (CDCl$_3$, 400 MHz) δ 1.47 (s, 9H), 2.31-2.33 (m, 2H), 3.56 (t, J = 5.2 Hz, 2H), 4.15 (bs, 2H) 6.10-6.11 (m, 1H), 6.87 (s, 1H), 7.05-7.07 (m, 1H), 7.10-7.23 (m, 1H), 7.31-7.38 (m, 2H), 7.84-7.86 (m, 1H), 10.02 (d, J = 6.8 Hz, 1H) | INT-2-V |
| A-56 | ethyl 4-[3-(2,6-dichloro-3-fluoro-benzoyl)indolizin-1-yl]benzoate | LCMS: m/z 456.0 (M + 1)$^+$. $^1$H NMR (DMSO-d$_6$, 400 MHz) δ 1.33 (t, J = 6.8 Hz, 3H), 4.33 (q, J = 6.8 Hz, 2H), 7.35-7.38 (m, 1H), 7.58-7.71 (m, 4H), 7.79-7.81 (m, 2H), 7.98-8.01 (m, 2H), 8.15-8.19 (m, 1H), 9.95 (d, J = 6.8 Hz, 1H) | INT-2-V |
| A-57 | 3-[3-[2-chloro-6-(trifluoromethyl)benzoyl]indolizin-1-yl]benzoic acid | LCMS: m/z 444.1 (M + 1)$^+$. $^1$H NMR (DMSO-d$_6$, 400 MHz) δ 7.33 (dt, J = 1.2, 7.2 Hz, 2H), 7.54-7.61 (m, 2H), 7.78 (t, J = 8.4 Hz, 1H), 7.83-7.86 (m, 2H), 7.90 (t, J = 6.4 Hz, 1H), 7.95 (t, J = 8.0 Hz, 1H), 8.03-8.05 (m, 2H), 9.93 (d, J = 6.8 Hz, 1H); 13.07 (bs, 1H) | INT-2-V |
| A-58 | 4-[8-chloro-3-[2-chloro-6-(trifluoromethyl)benzoyl]indolizin-1-yl]benzoic acid | LCMS: m/z 478.1 (M + 1)$^+$. $^1$H NMR (DMSO-d$_6$, 400 MHz) δ 7.15 (s, 1H), 7.28 (t, J = 8.00 Hz, 1H), 7.50 (d, J = 8.0 Hz, 2H), 7.65 (d, J = 7.2 Hz, 1H), 7.72-7.80 (m, 1H), 7.89-7.93 (m, 4H), 9.92 (d, J = 7.6 Hz, 1H); 13.01 (bs, 1H) | INT-2-V |
| A-59 | 4-[8-chloro-3-[2-chloro-6-(trifluoromethyl)benzoyl]indolizin-1-yl]-3-fluoro-benzoic acid | LCMS: m/z 496.1 (M + 1)$^+$. $^1$H NMR (DMSO-d$_6$, 400 MHz) δ 7.21 (s, 1H), 7.27-7.43 (m, 1H), 7.49-7.53 (m, 1H), 7.63-7.69 (m, 2H), 7.75-7.79 (m, 2H), 7.89-7.95 (m, 2H), 9.90 (d, J = 6.8 Hz, 1H); 13.23 (bs, 1H) | INT-2-V |
| A-60 | 4-[3-[2-chloro-6-(trifluoromethyl)benzoyl]indolizin-1-yl]-2-fluoro-benzoic acid | LCMS: m/z 462.1 (M + 1)$^+$. $^1$H NMR (DMSO-d$_6$, 400 MHz) δ 7.35 (dt, J = 1.2, 7.2 Hz, 1H), 7.51 (s, 1H), 7.56 (s, 1H), 7.59 (t, J = 2.4 Hz, 1H), 7.62 (d, J = 2 Hz, 1H), 7.63 (s, 1H), 7.79 (t, J = 8.8 Hz, 1H), 7.87-7.92 (m, 1H), | INT-2-V |

| No | IUPAC name | Characterization | INT used |
|---|---|---|---|
| | | 7.95 (d, J = 7.6 Hz, 1H), 8.19 (d, J = 10 Hz, 1H), 9.93 (d, J = 6.8 Hz, 1H); 13.01 (bs, 1H) | |
| A-61 | 4-[3-(2,6-dichlorobenzoyl)-8-(trifluoromethyl)indolizin-1-yl]benzoic acid | LCMS: m/z 478.0 (M + 1)+. 1H NMR (DMSO-d6, 400 MHz) δ 7.14 (s, 1H), 7.39-7.43 (m, 3H), 7.54-7.56 (m, 1H), 7.59-7.62 (m, 2H), 7.91-7.97 (m, 3H), 10.16 (d, J = 7.8 Hz, 1H); 12.99 (bs, 1H) | INT-2-V |
| A-62 | ethyl 4-[3-(2,6-dichlorobenzoyl)-8-(trifluoromethyl)indolizin-1-yl]benzoate | LCMS: m/z 506.1 (M + 1)+. 1H NMR (DMSO-d6, 400 MHz) δ 1.41 (t, J = 6.8 Hz, 3H), 4.39 (q, J = 6.8 Hz, 2H), 6.95 (s, 1H), 7.10 (t, J = 7.6 Hz, 1H), 7.31-7.40 (m, 5H), 7.66 (d, J = 7.6 Hz, 1H), 8.02-8.04 (m, 2H), 10.28 (d, J = 6.8 Hz, 1H) | INT-2-V |
| A-63 | 4-[3-(2,6-dichlorobenzoyl)-6-(trifluoromethyl)indolizin-1-yl]benzoic acid | LCMS: m/z 478 (M + 1)+. 1H NMR (DMSO-d6, 400 MHz) δ 7.56-7.66 (m, 4H), 7.74-7.79 (m, 3H), 7.99 (dd, J = 1.6, 9.8 Hz, 2H), 8.30 (d, J = 9.2 Hz, 1H), 10.26 (s, 1H), 12.96 (bs, 1H) | INT-2-V |
| A-64 | ethyl 4-[3-(2,6-dichlorobenzoyl)-6-(trifluoromethyl)indolizin-1-yl]benzoate | LCMS: m/z 506.1 (M + 1)+. 1H NMR (DMSO-d6, 400 MHz) δ 1.42 (t, J = 6.8 Hz, 3H), 4.40 (q, J = 6.8 Hz, 2H), 7.23-7.35 (m, 1H), 7.36-7.48 (m, 4H), 7.57-7.59 (m, 2H), 7.98 (d, J = 9.6 Hz, 1H), 8.11 (dd, J = 1.6, 6.4 Hz, 2H), 10.40 (s, 1H), | INT-2-V |
| A-65 | 4-[3-[2-chloro-6-(trifluoromethyl)benzoyl]indolizin-1-yl]cyclohex-3-ene-1-carboxylic acid | LCMS: m/z 448.1 (M + 1)+. 1H NMR (DMSO-d6, 400 MHz) δ 1.64 (bs, 1H), 1.99-2.02 (m, 1H), 2.34 (bs, 4H), 2.51-2.53 (m, 1H), 6.03 (bs, 1H), 6.91 (s, 1H), 7.23 (t, J = 6.8 Hz, 1H), 7.46 (dd, J = 6.8, 7.6 Hz, 1H), 7.76 (t, J = 8.0 Hz, 1H), 7.88-7.99 (m, 3H), 9.85 (d, J = 7.2 Hz, 1H), 12.18 (bs, 1H) | INT-2-V |
| A-66 | ethyl 4-[3-(2-bromo-6-methyl-benzoyl)indolizin-1-yl]benzoate | LCMS: m/z 532.0 (M + 1)+. 1H NMR (DMSO-d6, 400 MHz) δ 1.34 (t, J = 7.2 Hz, 3H), 4.30 (q, J = 7.2 Hz, 2H), 6.82 (s, 1H), 6.96-6.98 (m, 1H), 7.26-7.29 (m, 1H), 7.38-7.45 (m, 4H), 7.51-7.58 (m, 2H), 7.90 (d, J = 8.0 Hz, 2H), 9.90 (d, J = 8.0 Hz, 1H) | INT-2-V |

Synthesis B-2: 4-[3-(2,6-dichlorobenzoyl)-2-fluoro-indolizin-1-yl]benzoic acid

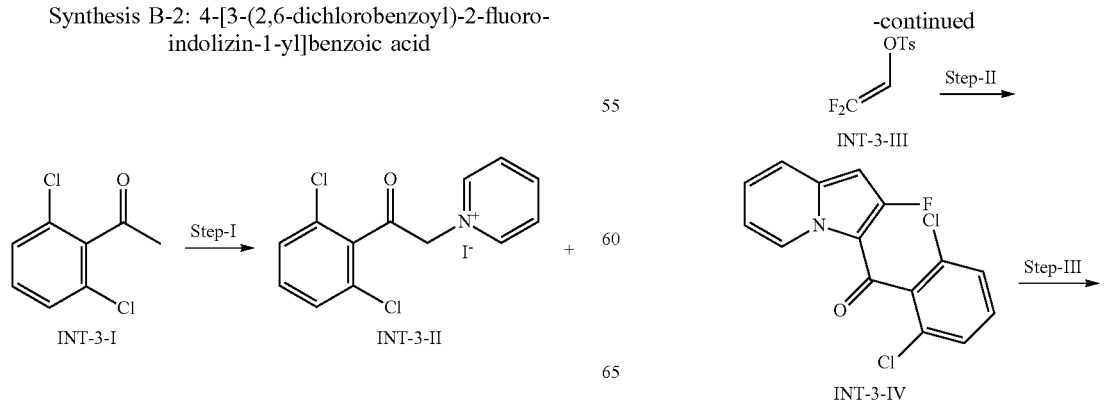

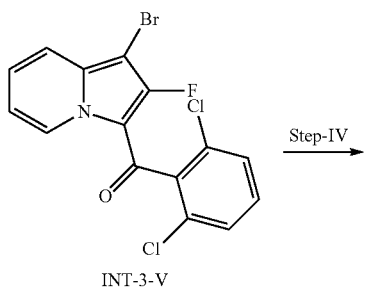

INT-3-V

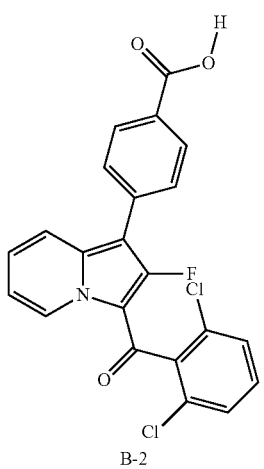

B-1

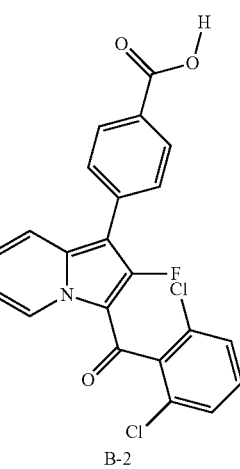

B-2

Step-I: INT-3-II: 1-(2,6-dichlorophenyl)-2-pyridin-1-ium-1-yl-ethanone iodide Title compound was synthesized as described for the synthesis of INT-2-II

Step-II: INT-3-IV: (2,6-dichlorophenyl)-(2-fluoroindolizin-3-yl)methanone

Reagent INT-3-III was prepared as reported in article Gogsig T. M. et al *J. Org. Chem.*, 2008, 72, 3404-3410.
Reagent INT-3-IV was prepared as reported in article Fanga X, et at. *Tetrahedron*, 2004, 60, 5487-5493.
LCMS: m/z 308.2 (M+1)$^+$. $^1$H NMR (DMSO-d$_6$, 400 MHz) δ 9.80-9.83 (m, 1H), 7.85-7.87 (m, 2H), 7.52-7.61 (m, 4H); 9.26-7.30 (m, 1H).

Step-III: INT-3-V: (1-bromo-2-fluoro-indolizin-3-yl)-(2,6-dichlorophenyl)methanone (2,6-dichlorophenyl)-imidazo[1,5-a]pyridin-1-yl-methanone (0.450 g, 1.46 mmol) in DCM (10 mL) was added NBS (0.287 g, 1.6 mmol) at −78° C. and the resulting mixture was cooled to room temperature and continue stirring for 1 h at same temperature. After disappearing of starting material on TLC, the reaction mixture was diluted with DCM washed with saturated sodium thiosulfate solution (2×50 mL), water (1×50 mL), dried over anhydrous sodium sulphate, filtered and concentrated gave the crude product (0.4 g, 72%) as a yellowish solid. The solid was used in the next step without any further purification. LCMS: m/z 385.7 (M+1)$^+$.

Step-IV: B-1: Ethyl 4-[3-(2,6-dichlorobenzoyl)-2-fluoro-indolizin-1-yl]benzoate Title compound was synthesized as described for the synthesis of A-1.
LCMS: m/z 456.0 (M+1)$^+$. $^1$H NMR (DMSO-d$_6$, 400 MHz) δ 1.34 (t, J=6.8 Hz, 3H), 4.34 (q, J=6.8 Hz, 2H), 7.40-7.43 (m, 1H), 7.53-7.54 (m, 1H), 7.62-7.64 (m, 2H), 7.69-7.72 (m, 3H), 8.02-8.06 (m, 3H), 9.96 (d, J=6.8 Hz, 1H)

Step-V: B-2: 4-[3-(2,6-dichlorobenzoyl)-2-fluoro-indolizin-1-yl]benzoic acid Title compound was synthesized as described for the synthesis of A-2
LCMS: m/z 428 (M+1)$^+$. $^1$H NMR (DMSO-d$_6$, 400 MHz) δ 7.39-7.43 (m, 1H), 7.53-7.57 (m, 1H), 7.61-7.63 (m, 2H), 7.66-7.69 (m, 3H), 8.02-8.05 (m, 3H), 9.95 (d, J=8.4 Hz, 1H), 13.01 (s, 1H)

Following compounds were prepared from its corresponding intermediate using the same sequence of procedures as used for preparation of Example B-2 from INT-3-V.

| No | IUPAC name | Characterization | INT used |
|---|---|---|---|
| B-3 | methyl 4-[3-(2,6-dichlorobenzoyl)-2-fluoro-indolizin-1-yl]-3-fluoro-benzoate | LCMS: m/z 460.0 (M + 1)$^+$. $^1$H NMR (DMSO-d$_6$, 400 MHz) δ 3.98 (s, 3H), 7.38-7.73 (m, 1H), 7.50-7.54 (m, 1H), 7.58-7.61 (m, 2H), 7.63-7.67 (m, 1H), 7.71-7.77 (m, 2H), 7.81-7.84 (m, 1H), 7.87-7.89 (m, 1H), 9.92 (d, J = 6.8 Hz, 1H) | INT-3-V |
| B-4 | 4-[3-(2,6-dichlorobenzoyl)-2- | LCMS: m/z 446.0 (M + 1)$^+$. $^1$H NMR (DMSO-d$_6$, 400 MHz) δ 7.40.7.42 (m, | INT-3-V |

| No | IUPAC name | Characterization | INT used |
|---|---|---|---|
| | fluoro-indolizin-1-yl]-3-fluoro-benzoic acid | 1H), 7.52-7.56 (m, 1H), 7.61-7.73 (m, 4H), 7.76-7.82 (m, 2H), 7.86-7.89 (m, 1H), 9.94 (d, J = 7.6 Hz, 1H), 13.40 (s, 1H) | |
| B-5 | ethyl 4-[3-(2,6-dichloro-3-fluoro-benzoyl)-2-fluoro-indolizin-1-yl]benzoate | LCMS: m/z 474.2 (M + 1)⁺. ¹H NMR (DMSO-$d_6$, 400 MHz) δ 1.13 (t, J = 6.8 Hz, 3H), 4.34 (q, J = 6.8 Hz, 2H), 7.42-7.46 (m, 1H), 7.37-7.63 (m, 5H), 8.04-8.06 (m, 3H), 9.94 (d, J = 6.8 Hz, 1H) | INT-3-V |
| B-6 | 4-[3-(2,6-dichloro-3-fluoro-benzoyl)-2-fluoro-indolizin-1-yl]benzoic acid | LCMS: m/z 446.1 (M + 1)⁺. ¹H NMR (DMSO-$d_6$, 400 MHz) δ 7.41-7.45 (m, 1H), 7.26-7.72 (m, 5H), 8.03-8.06 (m, 3H), 9.94 (d, J = 7.2 Hz, 1H), 13.02 (s, 1H) | INT-3-V |

Synthesis C-2: 4-[3-(2,6-dichlorobenzoyl)-2-methyl-indolizin-1-yl]-3-fluoro-benzoic acid

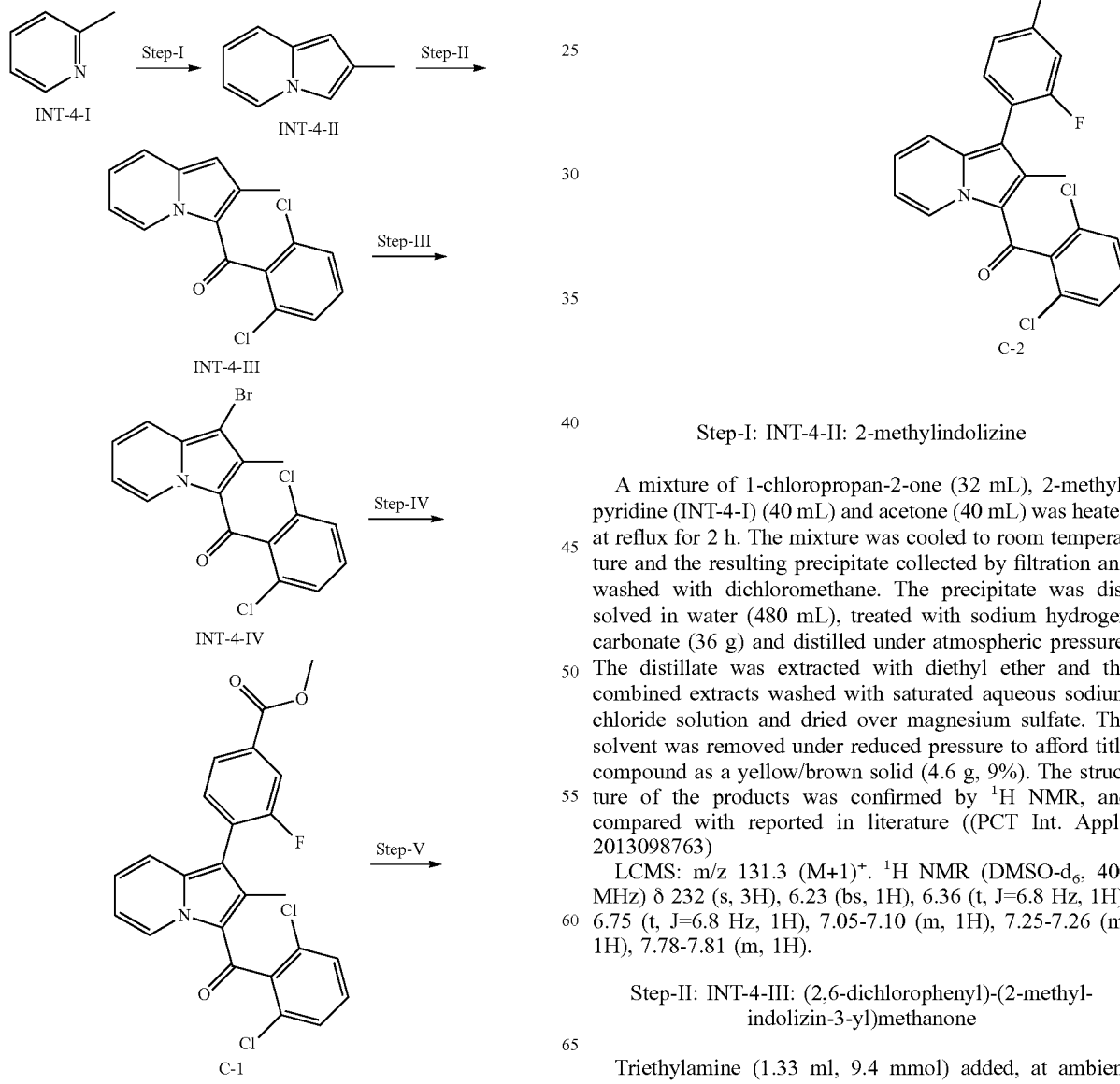

Step-I: INT-4-II: 2-methylindolizine

A mixture of 1-chloropropan-2-one (32 mL), 2-methylpyridine (INT-4-I) (40 mL) and acetone (40 mL) was heated at reflux for 2 h. The mixture was cooled to room temperature and the resulting precipitate collected by filtration and washed with dichloromethane. The precipitate was dissolved in water (480 mL), treated with sodium hydrogen carbonate (36 g) and distilled under atmospheric pressure. The distillate was extracted with diethyl ether and the combined extracts washed with saturated aqueous sodium chloride solution and dried over magnesium sulfate. The solvent was removed under reduced pressure to afford title compound as a yellow/brown solid (4.6 g, 9%). The structure of the products was confirmed by ¹H NMR, and compared with reported in literature ((PCT Int. Appl., 2013098763)

LCMS: m/z 131.3 (M+1)⁺. ¹H NMR (DMSO-$d_6$, 400 MHz) δ 232 (s, 3H), 6.23 (bs, 1H), 6.36 (t, J=6.8 Hz, 1H), 6.75 (t, J=6.8 Hz, 1H), 7.05-7.10 (m, 1H), 7.25-7.26 (m, 1H), 7.78-7.81 (m, 1H).

Step-II: INT-4-III: (2,6-dichlorophenyl)-(2-methyl-indolizin-3-yl)methanone

Triethylamine (1.33 ml, 9.4 mmol) added, at ambient temperature under an inert atmosphere, to 2-methylindolizine (INT-4-II) (1 g, 7.6 mmole) in 20 ml of dichloroethane, 2,6-dichlorobenzoyl chloride (1.25 ml, 8.3 mmol) was added dropwise to reaction mixture. The reaction medium was stirred for 18 h at ambient temperature, hydrolysed with a saturated aqueous solution (50 ml) of sodium hydrogen carbonate and then extracted with dichloromethane (3×50 mL). The organic phase is washed with a saturated aqueous solution of sodium chloride, dried over sodium sulphate, and then concentrated under reduced pressure. The residue obtained is washed with diethyl ether afforded brown solid (800 mg 35%).

LCMS: m/z 304.2 (M+1)$^+$. $^1$H NMR (DMSO-d$_6$, 400 MHz) δ 1.92 (s, 3H), 6.34 (s, 1H), 6.93-697 (m, 1H), 7.27-7.37 (m, 4H), 7.45-7.48 (m, 1H), 10.17 (d, J=8.0 Hz, 1H).

Step-III: INT-4-IV: (1-brano-2-methyl-indolizin-3-yl)-(2,6-dichlorophenyl)methanone N-Bromosuccinimide (0.516 g, 59.8 mmol) is added portionwise to a solution of (2,6-dichlorophenyl)-(2-methylindolizin-3-yl)methanone (0.80 g; 2.6 mmol) in 15 mL of DCM. After 1 h of stirring at ambient temperature, the reaction was diluted with dichloro methane (10 ml), washed with saturated sodium thiosulfate solution (2×50 mL), water (1×50 mL), dried over anhydrous sodium sulphate, filtered and concentrated gave the crude product (0.810 g, 81%) as a off white solid. The solid was used in the next step without any further purification.

LCMS: m/z 384 (M+1)$^+$. $^1$H NMR (DMSO-d$_6$, 400 MHz) δ 1.84 (s, 3H), 7.01-7.05 (m, 1H), 7.27-7.40 (m, 4H), 7.56-7.61 (m, 1H), 10.17 (d, J=8.0 Hz, 1H).

Step-IV: C-1: ethyl 4-[3-(2,6-dichlorobenzoyl)-2-methyl-indolizin-1-yl]-3-fluoro-benzoate 1,1'-Bis(diphenylphosphino)ferrocene-palladium(II)dichloride dichloromethane complex (0.043 g, 0.53 mmol) was added to a degassed solution of (1-bromo-2-methyl-indolizin-3-yl)-(2,6-dichlorophenyl)methanone (0.2 g, 0.525 mmol), (2-fluoro-4-methoxycarbonyl-phenyl)boronic acid (0.125 g, 0.63 mmol) and potassium carbonate (0.217 g, 1.57 mmol) in 1 ml of water and dioxane (3 mL) under an inert argon atmosphere. The reaction medium was heated at 110° C. for 15 min in microwave. The reaction medium was acidified with a 1N aqueous solution of hydrochloric acid and extracted with dichloromethane. The organic phase was washed with water, dried over sodium sulphate, filtered and concentrated under reduced pressure. The residue was purified on combifalsh system with a gradient of 10 to 20% ethyl acetate-hexanes to obtain the desired product C-1 (0.09 g, 47%).

LCMS: m/z 456.0 (M+1)$^+$. $^1$H NMR (DMSO-d$_6$, 400 MHz) δ 1.74 (s, 3H), 3.94 (s, 3H), 7.04-7.06 (m, 1H), 7.29-7.33 (m, 2H), 7.37-7.38 (m, 4H), 7.86 (dd, J=1.2, 10.0 Hz, 1H), 7.91 (dd, J=1.2, 7.6 Hz, 1H), 10.28 (d, J=8.0 Hz, 1H)

Step-V: C-2: 4-[3-(2,6-dichlorobenzoyl)-2-methyl-indolizin-1-yl]-3-fluoro-benzoic acid A solution of methyl ethyl 4-[3-(2,6-dichlorobenzoyl)-2-methyl-indolizin-1-yl]-3-fluoro-benzoate (0.70 g, 0.15 mmol) in a mixture of THF:EtOH:H$_2$O (5:5:1 mL) was added LiOH.H$_2$O (0.020 g, 0.46 mmol) at room temperature and the mixture was stirred for 16 h. After completion of the reaction, the solvents were removed under reduced pressure. The crude product was dissolved in the water and acidified with 1N HCl solution up to pH=3. Obtained solid was filtered and dried to afford the title compound C-2 (0.050 g, 80%).

LCMS: m/z 442 (M+1)$^+$. $^1$H NMR (DMSO-d$_6$, 400 MHz) δ 1.66 (s, 3H), 7.25-7.28 (m, 1H), 7.50-7.55 (m, 2H), 7.56-7.62 (m, 1H), 7.63-7.65 (m, 3H), 7.79-7.82 (m, 1H), 7.86-7.88 (m, 1H), 10.13 (d, J=7.2 Hz, 1H), 13.31 (s, 1H).

Following compounds were prepared from its corresponding intermediate using the same sequence of procedures as used for preparation of example C-2 from INT-4-IV

| No | IUPAC name | Characterization | INT used |
|---|---|---|---|
| C-3 | ethyl 4-[3-(2,6-dichlorobenzoyl)-2-methyl-indolizin-1-yl]benzoate | LCMS: m/z 452.0 (M + 1)$^+$. $^1$H NMR (DMSO-d$_6$, 400 MHz) δ 1.48 (t, J = 7.6 Hz, 3H), 1.86 (s, 3H), 4.41 (q, J = 7.2 Hz, 2H), 7.03 (t, J = 6.0 Hz, 1H), 7.26-7.33 (m, 2H), 7.39-7.41 (m, 2H), 7.45 (d, J = 7.6 Hz, 2H), 7.54 (d, J = 8.8 Hz, 1H), 8.13 (d, J = 8.4 Hz, 2H). 10.28 (d, J = 6.8 Hz, 1H) | INT-4-IV |
| C-4 | 4-[3-(2,6-dichlorobenzoyl)-2-methyl-indolizin-1-yl]benzoic acid | LCMS: m/z 424 (M + 1)$^+$. $^1$H NMR (DMSO-d$_6$, 400 MHz) δ 1.80 (s, 3H), 7.24-7.28 (m, 1H), 7.48-7.57 (m, 4H), 7.63-7.68 (m, 3H), 8.04 (d, J = 8.4 Hz, 2H), 10.14 (d, J = 6.8 Hz, 1H), 13.01 (s, 1H) | INT-4-IV |
| C-5 | 4-[3-(2,4-dichloropyridine-3-carbonyl)-2-methyl-indolizin-1-yl]benzoic acid | LCMS: m/z 425 (M + 1)$^+$. $^1$H NMR (DMSO-d$_6$, 400 MHz) δ 1.80 (s, 3H), 7.28-7.32 (m, 1H), 7.52-7.56 (m, 3H), 7.69 (d J = 8.8 Hz, 1H), 7.85 (d, J = 5.2 Hz, 1H), 8.05 (d, J = 7.6 Hz, 2H), 8.56 (d, J = 5.6 Hz, 1H), 10.13 (d, J = 6.8 Hz, 1H), 13.01 (s, 1H), | INT-4-IV |
| C-6 | 4-[3-[2-chloro-6-(trifluoromethyl)benzoyl]-2-methyl-indolizin-1-yl]-3-fluoro-benzoic acid | LCMS: m/z 476 (M + 1)$^+$. $^1$H NMR (DMSO-d$_6$, 400 MHz) δ 1.60 (s, 3H), 7.25-7.27 (m, 1H), 7.51-7.52 (m, 2H), 7.55-7.59 (m, 1H), 7.75-7.81 (m, 2H), 7.86-7.88 (m, 1H), 7.93-7.95 (m, 1H), 7.97-7.99 (m, 1H), 10.09 (d, J = 6.8 Hz, 1H), 13.03 (s, 1H) | INT-4-IV |
| C-7 | 4-[3-[2-chloro-6-(trifluoromethyl)benzoyl]- | LCMS: m/z 458 (M + 1)$^+$. $^1$H NMR (DMSO-d$_6$, 400 MHz) δ 1.60 (s, 3H), 7.23- | INT-4-IV |

| No | IUPAC name | Characterization | INT used |
|---|---|---|---|
| | 2-methyl-indolizin-1-yl]benzoic acid | 7.27 (m, 1H), 7.48-7.53 (m, 3H), 7.65-7.68 (m, 1H), 7.77 (t, J = 7.6 Hz, 1H), 7.92-8.03 (m, 2H), 8.04-8.05 (m, 2H), 10.11 (d, J = 7.2 Hz, 1H), 13.01 (s, 1H), | |
| C-8 | methyl 4-[3-[2-chloro-6-(trifluoromethyl)benzoyl]-2-methyl-indolizin-1-yl]-3-fluoro-benzoate | LCMS: m/z 490 (M + 1)$^+$. $^1$H NMR (DMSO-d$_6$, 400 MHz) δ 1.60 (s, 3H), 4.01 (s, 3H), 7.02-7.06 (m, 1H), 7.29-7.39 (m, 3H), 7.49 (t, J = 8.8 Hz, 1H), 7.69 (t, J = 8.8 Hz, 2H), 7.83-7.92 (m, 2H), 10.22-10.24 (m, 1H) | INT-4-IV |
| C-9 | ethyl 4-[3-[2-chloro-6-(trifluoromethyl)benzoyl]-2-methyl-indolizin-1-yl]benzoate | LCMS: m/z 486.0 (M + 1)$^+$. $^1$H NMR (CDCl$_3$, 400 MHz) δ 1.42 (t, J = 7.6 Hz, 3H), 1.73 (s, 3H), 4.40 (q, J = 7.6 Hz, 2H), 7.00-7.04 (m, 1H), 7.27-7.32 (m, 1H), 7.42-7.50 (m, 2H), 7.52-7.55 (m, 2H), 7.69 (t, J = 5.2 Hz, 2H), 8.11-8.13 (m, 2H), 10.23-10.25 (m, 1H) | INT-4-IV |
| C-10 | ethyl 4-[3-(2,4-dichloropyridine-3-carbonyl)-2-methyl-indolizin-1-yl]benzoate | LCMS: m/z 453.0 (M + 1)$^+$. $^1$H NMR (CDCl$_3$, 400 MHz) δ 1.42 (t, J = 6.8 Hz, 3H), 1.85 (s, 3H), 4.21 (q, J = 6.8 Hz, 2H), 7.05-7.07 (m, 1H), 7.33-7.37 (m, 1H), 7.41-7.46 (m, 3H), 7.54-7.57 (m, 1H), 8.14 (d, J = 8.4 Hz, 2H), 8.38 (d, J = 6 Hz, 1H), 10.26 (d, J = 6.8 Hz, 1H) | INT-4-IV |

Synthesis D-1: 4-[3-[2-chloro-6-(trifluoromethyl)benzoyl]-6-(dimethylcarbamoyl)indolizin-1-yl]benzoic acid

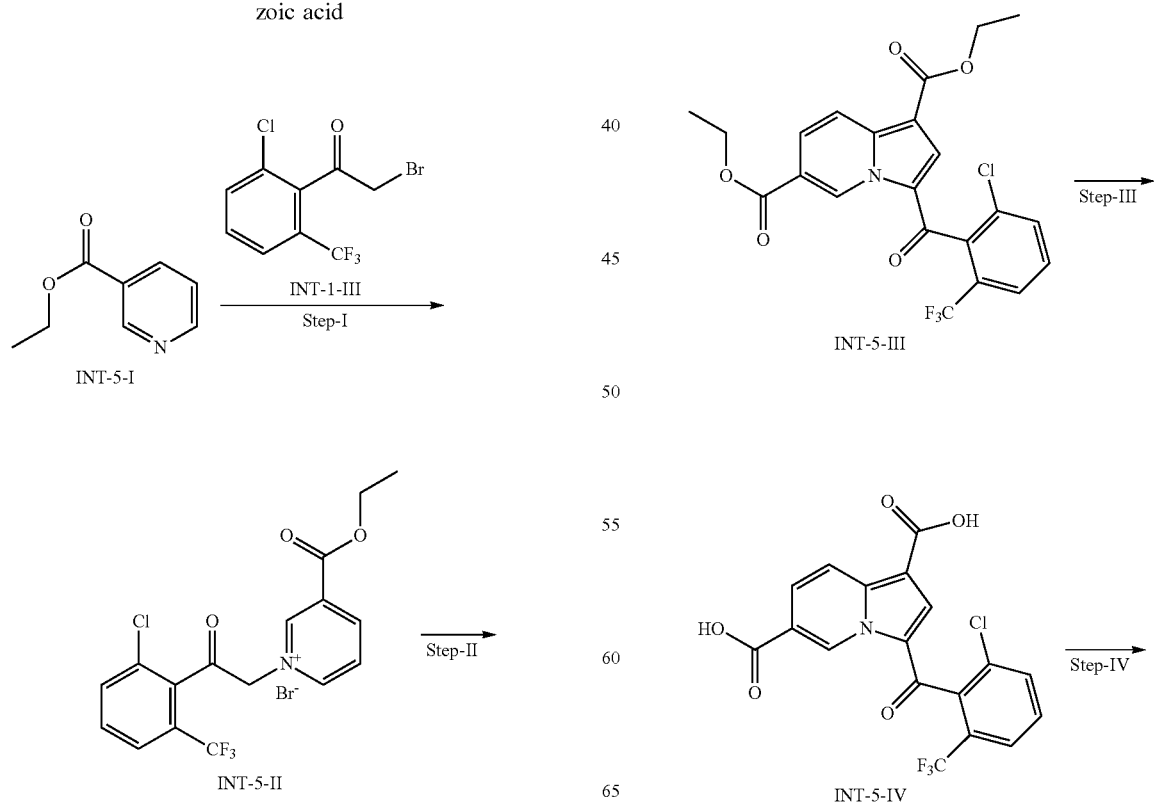

-continued

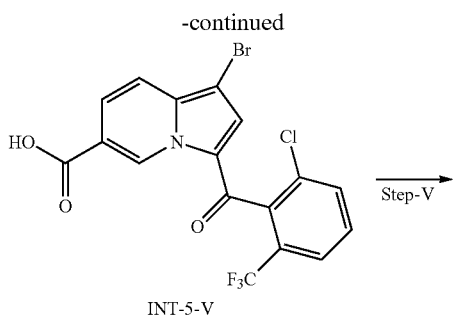
INT-5-V

Step-V →

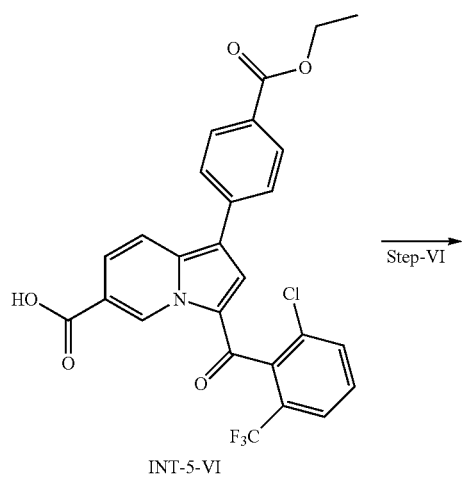
INT-5-VI

Step-VI →

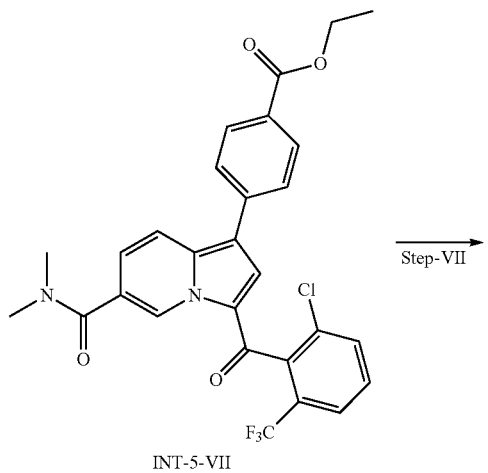
INT-5-VII

Step-VII →

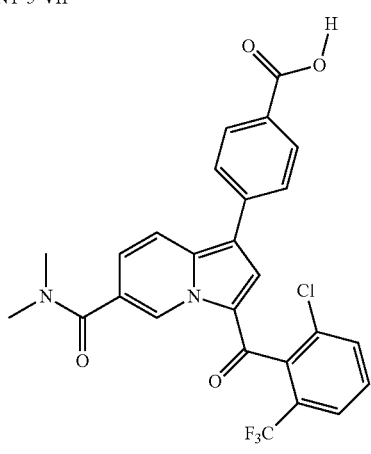
D-1

Step-I: INT-5-II: ethyl 1-[2-[2-chloro-6-methyl)phenyl]-2-oxo-ethyl]pyridine-1-ium-3-carboxylate bromide To a solution of 2-bromo-1-[2-chloro-6-(trifluoromethyl)phenyl]ethanone (5 g, 16.6 mmol) in acetonitrile (30 ml) was added ethyl pyridine-3-carboxylate (3.42 ml, 16.6 mmol). The mixture was refluxed for 48 h. The solvent was evaporated in a vacuum, the residue was treated with ether (30 ml×3) to remove unreacted substances to give the crude product (4.5 g).

Step-II: INT-5-III: diethyl 3-[2-chloro-6-(trifluoromethyl)benzoyl]indolizine-1,6-dicarboxylate Title compound was synthesized as described for the synthesis of INT-2-III
LCMS: m/z 468.1 (M+1)$^+$. $^1$H NMR (DMSO-d$_6$, 400 MHz) δ 1.24 (t, J=6.8 Hz, 3H), 1.39 (t, J=7.6 Hz, 3H); 4.31 (q, J=7.6 Hz, 2H); 4.44 (q, J=6.8 Hz, 2H); 7.48 (s, 1H), 7.84 (t, J=7.6 Hz, 1H), 7.95-8.04 (m, 2H); 8.10-8.13 (m, 1H), 8.41-8.44 (m, 1H); 10.42 (s, 1H).

Step-III: INT-5-IV: 3-[2-chloro-6-(trifluoromethyl)benzoyl]indolizine-1,6-dicarboxylic acid Diethyl 3-[2-chloro-6-(trifluoromethyl)benzoyl]indolizine-1,6-dicarboxylate (0.40 g (0.8 mmol) was stirred at room temperature with NaOH (0.102 g, 2.5 mmol) in 8 ml THF and 5 mL of EtOH for 12 h. The reaction mixture was concentrated in vacuo and the residue was dissolved in H$_2$O (20 mL) and washed with EtOAc (50 mL×3). The aqueous phase was acidified with HCl (1M in H$_2$O) and extracted with DCM (3×50 mL). The combined organic phases were dried (MgSO$_4$), filtered and concentrated in vacuo. The title compound was obtained as a white solid (0.3 g, 85%). LCMS: m/z 412.0 (M+1)$^+$.

Step-IV: INT-5-V: 1-bromo-3-[2-chloro-6-(trifluoromethyl)benzoyl]indolizine-6-carboxylic acid Title compound was synthesized as described for the synthesis of INT-2-V LCMS: m/z 446.0 (M+1)$^-$.

Step-V: INT-5-VI: 3-[2-chloro-6-(trifluoromethyl)benzoyl]-1-(4-ethoxycarbonylphenyl)indolizine-6-carboxylic acid Title compound was synthesized as described for the synthesis of A-1. LCMS: m/z 516.0 (M+1)$^-$.

Step-VI: INT-5-VII: ethyl 4-[3-[2-chloro-6-(trifluoromethyl)benzoyl]-6-(dimethylcarbamoyl)indolizin-1-yl]benzoate To a stirred mixture of 3-[2-chloro-6-(trifluoromethyl)benzoyl]-1-(4-ethoxycarbonylphenyl)indolizine-6-carboxylic acid (0.090 g, 0.17 mmol), dimethyl amine in 2M in THF (0.12 ml, 0.34 mmol) and triethylamine (0.069 mL, 0.51 mmol) in dry CH$_2$Cl$_2$ (10 mL) was stirred at room temperature for 15 min. To that propylphosphonic anhydride (T3P) (0.11 mL, 0.37 mmol) was added. The reaction mixture was stirred overnight at room temperature. After completion of the reaction (by TLC), it was quenched by the addition of water and aqueous phase was extracted with CH$_2$Cl$_2$ (3×10 mL). Combined organic layer was washed with saturated aqueous NaHCO3 solution, brine, dried over Na$_2$SO$_4$, filtered and the solvent was removed to give a solid. The crude product was purified by silica gel column chromatography (5% Methanol in DCM) to provide title compound as yellow solid (0.070 g, 74%). LCMS: m/z 543.2 (M+1)$^+$.

Step-VII: D-1: 4-[3-[2-chloro-6-(trifluoromethyl) benzoyl]-6-(dimethylcarbamoyl)indolizin-1-yl]benzoic acid A solution of ethyl 4-[3-[2-chloro-6-(trifluoromethyl)benzoyl]-6-(dimethylcarbamoyl) indolizin-1-yl]benzoate (0.05 g, 0.2 mmol) in a mixture of THF:H$_2$O (5:1 mL) was added LiOH.H$_2$O (0.014 g, 0.32 mmol) at room temperature and the mixture was stirred for 16 h. After completion of the reaction, the solvents were removed under reduced pressure. The crude product was dissolved in the water and acidified with 1N HCl solution up to pH=3. Obtained solid was filtered and dried to afford the title compound D-1 (0.020 g, 35%)

LCMS: m/z 515.1 (M+1)$^+$. $^1$H NMR (DMSO-d$_6$, 400 MHz) δ 3.07 (s, 6H), 7.49 (s, 1H), 7.62 (d, J=9.2 Hz, 1H), 7.41-7.82 (m, 3H), 7.91-7.99 (m, 4H), 8.17 (d, J=9.2 Hz, 1H), 10.04 (s, 1H), 12.97 (s, 1H)

Following compounds were prepared from its corresponding intermediate using the same sequence of procedures as used for preparation of Example D-1 from INT-5-VII

| No | IUPAC name | Characterization | INT used |
|---|---|---|---|
| D-2 | 4-[3-(2,6-dichlorobenzoyl)-6-(dimethylcarbamoyl)indolizin-1-yl]benzoic acid | LCMS: m/z 481.2 (M + 1)$^+$. $^1$H NMR (DMSO-d$_6$, 400 MHz) δ 3.14 (s, 6H), 7.51 (s, 1H), 7.56-7.65 (m, 4H), 7.76-7.78 (m, 2H), 7.97-8.00 (m, 2H), 8.16-8.18 (m, 1H), 10.05 (s, 1H), 12.95 (s, 1H) | INT-5-VII |
| D-3 | 4-[3-(2,6-dichlorobenzoyl)-6-(morpholine-4-carbonyl)indolizin-1-yl]benzoic acid | LCMS: m/z 523.1 (M + 1)$^+$. $^1$H NMR (DMSO-d$_6$, 400 MHz) δ 3.59-3.67 (m, 8H), 7.52 (s, 1H), 7.57-7.64 (m, 4H), 7.77-7.79 (m, 2H), 7.98-8.00 (m, 2H), 8.18 (d, J = 9.2 Hz, 1H), 10.05 (s, 1H), 12.95 (s, 1H) | INT-5-VII |
| D-4 | 4-[3-(2,6-dichlorobenzoyl)-6-(piperidine-1-carbonyl)indolizin-1-yl]benzoic acid | LCMS: m/z 521.1 (M + 1)$^+$. $^1$H NMR (DMSO-d$_6$, 400 MHz) δ 1.57-1.66 (m, 6H), 3.56-3.59 (m, 4H), 7.52 (s, 1H), 7.56-7.60 (m, 2H), 7.64-7.66 (m, 2H), 7.77-7.79 (m, 2H), 7.98-8.00 (m, 2H), 8.17 (d, J = 9.6 Hz, 1H), 10.00 (s, 1H), 13.01 (s, 1H) | INT-5-VII |
| D-5 | 4-[3-(2,6-dichlorobenzoyl)-6-(pyrrolidine-1-carbonyl)indolizin-1-yl]benzoic acid | LCMS: m/z 507 (M + 1)$^+$. $^1$H NMR (DMSO-d$_6$, 400 MHz) δ 1.91-1.93 (m, 4H), 3.55 (t, J = 6.8 Hz, 2H), 3.61 (t, J = 5.6 Hz, 2H), 7.53 (s, 1H), 7.58-7.63 (m, 1H), 7.66-7.65 (m, 2H), 7.73-7.79 (m, 3H), 7.97-7.99 (m, 2H), 8.16 (d, J = 9.2 Hz, 1H), 10.20 (s, 1H), 12.98 (s, 1H) | INT-5-VII |
| D-6 | 4-[6-(azetidine-1-carbonyl)-3-(2,6-dichlorobenzoyl)indolizin-1-yl]benzoic acid | LCMS: m/z 493.1 (M + 1)$^+$. $^1$H NMR (DMSO-d$_6$, 400 MHz) δ 3.32-2.36 (m, 2H), 4.14-4.16 (m, 2H), 4.50-4.52 (m, 2H), 7.55 (s, 1H), 7.64-7.56 (m, 1H), 7.65-7.67 (m, 2H), 7.73-7.77 (m, 3H), 7.97-8.00 (m, 2H), 8.16 (d, J = 9.6 Hz, 1H), 10.26 (s, 1H), 13.02 (s, 1H) | INT-5-VII |
| D-7 | 4-[3-(2,6-dichlorobenzoyl)-6-(2-hydroxyethylcarbamoyl)indolizin-1-yl]benzoic acid | LCMS: m/z 497.1 (M + 1)$^+$. $^1$H NMR (DMSO-d$_6$, 400 MHz) δ 3.38 (m, 2H), 3.58 (d, J = 6.0 Hz, 2H), 4.81 (bs, 1H), 7.52 (s, 1H), 7.57-7.63 (m, 1H), 7.65-7.67 (m, 2H), 7.74-7.76 (m, 2H), 7.95-7.99 (m, 3H), 8.19 (d, J = 9.6 Hz, 1H), 8.94 (s, 1H), 10.42 (s, 1H), 13.01 (s, 1H) | INT-5-VII |
| D-8 | 4-[3-(2,6-dichlorobenzoyl)-6-(2-methoxyethylcarbamoyl)indolizin-1-yl]benzoic acid | LCMS: m/z 511.1 (M + 1)$^+$. $^1$H NMR (DMSO-d$_6$, 400 MHz) δ 3.30 (s, 3H), 3.49-3.52 (m, 4H), 7.54 (s, 1H), 7.57-7.60 (m, 1H), 7.64-7.66 (m, 2H), 7.76-7.78 (m, 2H), 7.94-8.00 (m, 3H), 8.02 (d, J = 9.6 Hz, 1H), 9.01 (s, 1H), 10.42 (s, 1H), 13.02 (s, 1H) | INT-5-VII |
| D-9 | 4-[3-(2,6-dichlorobenzoyl)-6-(methylcarbamoyl)indolizin-1-yl]benzoic acid | LCMS: m/z 511.1 (M + 1)$^+$. $^1$H NMR (DMSO-d$_6$, 400 MHz) δ 2.86 (d, J = 4.4 Hz, 3H), 7.54 (s, 1H), 7.58-7.63 (m, 1H), 7.65-7.66 (m, 2H), 7.77-7.79 (m, 2H), 7.91-7.97 (m, 1H), 7.98-8.00 (m, 2H), 8.21 (d, J = 9.6 Hz, 1H), 8.87-8.88 (m, 1H), 10.41 (s, 1H), 13.02 (s, 1H) | INT-5-VII |
| D-10 | 4-[3-(2,6-dichlorobenzoyl)-6-(4H-1,2,4-triazol-3-yl)indolizin-1- | LCMS: m/z 511.1 (M + 1)$^+$. $^1$H NMR (DMSO-d$_6$, 400 MHz) δ 7.48 (s, 1H), 7.56-7.61 (m, 1H), 7.64-7.66 (m, 2H), 7.78-7.80 (m, 2H), 7.99-8.02 (m, 2H), | INT-5-VII |

| No | IUPAC name | Characterization | INT used |
|---|---|---|---|
| | yl]benzoic acid | 8.12-8.15 (m, 2H), 8.26 (d, J = 9.6 Hz, 1H), 8.72 (s, 1H), 10.61 (s, 1H), 13.02 (s, 1H) | |
| D-11 | 4-[6-(azetidine-1-carbonyl)-3-[2-chloro-6-(trifluoromethyl)benzoyl]indolizin-1-yl]benzoic acid | LCMS: m/z 527.1 (M + 1)⁺. ¹H NMR (DMSO-d₆, 400 MHz) δ 2.32-2.36 (m, 2H), 4.33 (bs, 2H), 4.51 (bs, 2H), 7.54 (s, 1H), 7.23-7.82 (m, 4H), 7.92-7.99 (m, 4H), 8.16 (d, J = 9.2 Hz, 1H), 10.24 (s, 1H), 13.12 (s, 1H) | INT-5-VII |
| D-12 | 4-[3-[2-chloro-6-(trifluoromethyl)benzoyl]-6-(pyrrolidine-1-carbonyl)indolizin-1-yl]benzoic acid | LCMS: m/z 515.1 (M + 1)⁺. ¹H NMR (DMSO-d₆, 400 MHz) δ 1.87-1.90 (m, 4H), 3.52-3.578 (m, 6H), 7.51 (s, 1H), 7.74-7.77 (m, 4H), 7.92-8.00 (m, 4H), 8.20-8.30 (m, 1H), 10.13 (s, 1H), 12.96 (s, 1H) | INT-5-VII |
| D-13 | 4-[6-carbamoyl-3-(2,6-dichlorobenzoyl)indolizin-1-yl]benzoic acid | LCMS: m/z 454 (M + 1)⁺. ¹H NMR (DMSO-d₆, 400 MHz) δ 7.51 (s, 1H), 7.54-7.58 (m, 1H), 7.62-7.64 (m, 2H), 7.70 (bs, 1H), 7.54-7.78 (m, 2H), 7.93-7.98 (m, 3H), 8.17 (d, J = 9.6 Hz, 1H), 10.41 (s, 1H), 13.01 (bs, 1H) | INT-5-VII |
| D-14 | 4-[3-(2,6-dichlorobenzoyl)-6-(3-methoxyazetidine-1-carbonyl)indolizin-1-yl]benzoic acid | LCMS: m/z 523.1 (M + 1)⁺. ¹H NMR (DMSO-d₆, 400 MHz) δ 3.26 (s, 3H), 3.75 (bs, 1H), 4.33 (bs, 4H), 7.56-7.66 (m, 4H), 7.74-7.82 (m, 3H), 7.99 (d, J = 8.4 Hz, 2H), 8.16 (d, J = 9 Hz, 1H), 10.26 (s, 1H), 12.96 (bs, 1H) | INT-5-VII |

Synthesis E-2: 4-[3-(2,6-dichlorophenoxy)indolizin-1-yl]benzoic acid

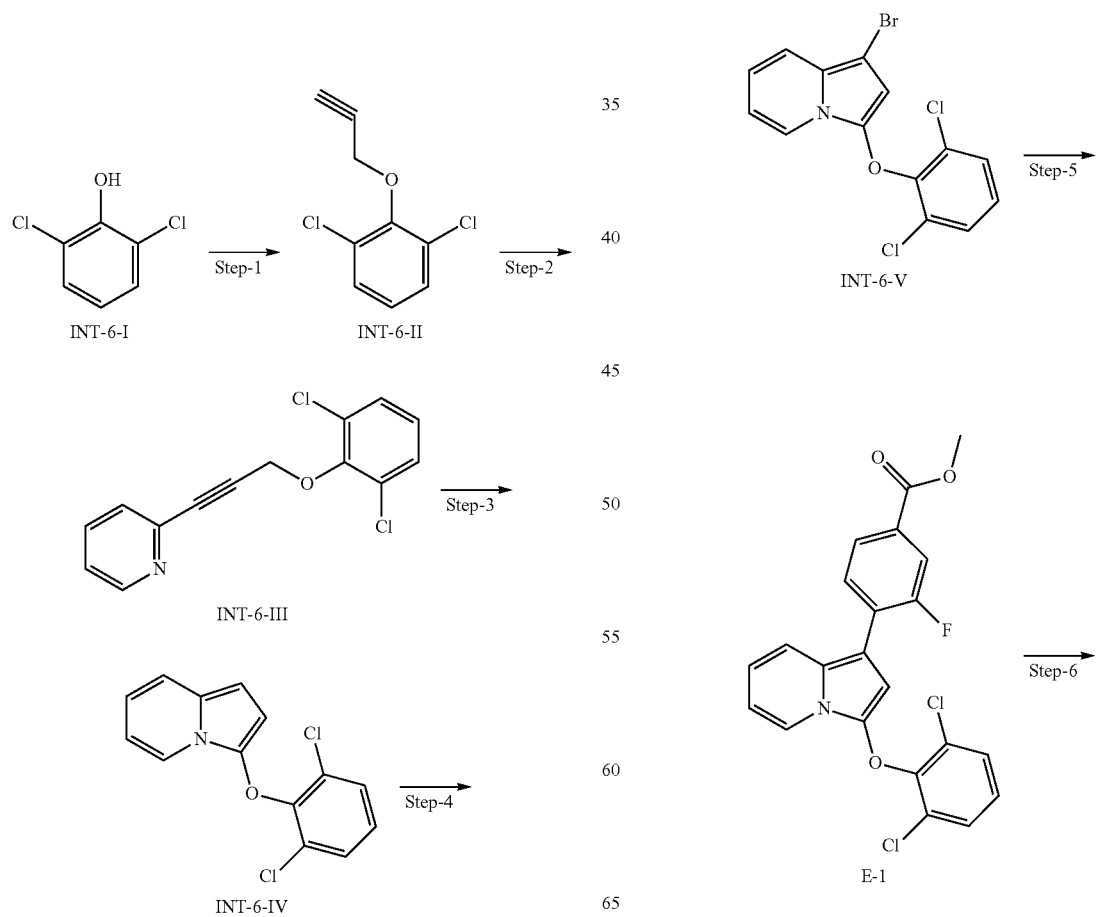

| No | IUPAC name | Characterization | INT used |
|---|---|---|---|
| E-3 | 4-[3-(2,6-dichloro-phenoxy)indolizin-1-yl]benzoic acid | LCMS: m/z 394.1 (M + 1)⁺. ¹H NMR (DMSO-d₆, 400 MHz) δ 6.29 (s, 1H), 6.79-6.82 (m, 1H), 6.87-6.90 (m, 1H), 7.43 (t, J = 6.8 Hz, 1H), 7.65-7.71 (m, 4H), 7.89-7.91 (m, 3H), 8.24 (d, J = 5.2 Hz, 1H), 12.90 (s, 1H) | INT-6-V |

Synthesis F-1: 4-[3-(2,6-dichloro-3-fluoro-benzoyl)imidazo[1,5-a]pyridin-1-yl]-N-methyl-benzamide

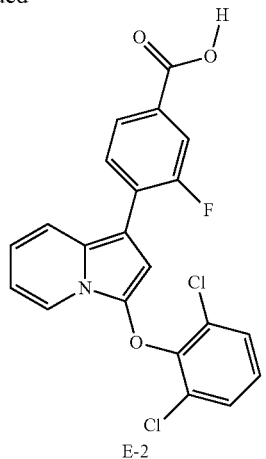

E-2

Step-1: INT-6-I:
1,3-dichloro-2-prop-2-ynoxy-benzene

Prepared as reported in patent WO2004054507

Step-2: INT-6-II: 2-[3-(2,6-dichlorophenoxy)prop-1-ynyl]pyridine

Prepared as reported in patent WO2004054507

Step-3: INT-6-III:
3-(2,6-dichlorophenoxy)indolizine

Prepared as reported in patent WO2004054507

Step-4: INT-6-IV:
1-bromo-3-(2,6-dichlorophenoxy)indolizine

Title compound was synthesized as described for the synthesis of INT-2-V LCMS: m/z 357.02 (M+1)⁻.

Step-5: E-1: methyl 4-[3-(2,6-dichlorophenoxy)indolizin-1-yl]-3-fluoro-benzoate

Title compound was synthesized as described for the synthesis of A-1
LCMS: m/z 429 (M+1)⁺. ¹H NMR (DMSO-d₆, 400 MHz) δ 3.95 (s, 3H), 6.12 (d, J=2.4 Hz, 1H), 6.63-6.69 (m, 1H), 6.75-6.80 (m, 1H), 7.18 (t, J=7.6 Hz, 1H), 7.42 (d, J=8 Hz, 2H), 7.54-7.58 (m, 2H), 7.75 (dd, J=1.2, 11.2 Hz, 1H) 7.81 (dd, J=2, 8.0 Hz, 1H) 8.12 (dd, J=1.6, 6.8 Hz, 1H).

Step-6: E-2: 4-[3-(2,6-dichlorophenoxy)indolizin-1-yl]-3-fluoro-benzoic acid

Title compound was synthesized as described for the synthesis of A-2
LCMS: m/z 416.1 (M+1)⁺. ¹H NMR (DMSO-d₆, 400 MHz) δ 6.14 (d, J=2 Hz, 1H), 6.82-6.91 (m, 2H), 7.42 (t, J=8.0 Hz, 1H), 7.61 (dd, J=1.2, 9.2 Hz, 1H), 7.60-7.70 (m, 4H), 7.76 (dd, J=1.6, 8.0 Hz, 1H), 8.27 (d, J=6.8 Hz, 1H) 13.05 (s, 1H).

Following compounds were prepared from its corresponding intermediate using the same sequence of procedures as used for preparation of Example E-2 from INT-6-V

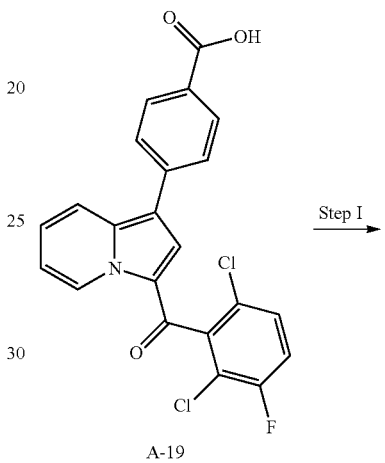

A-19

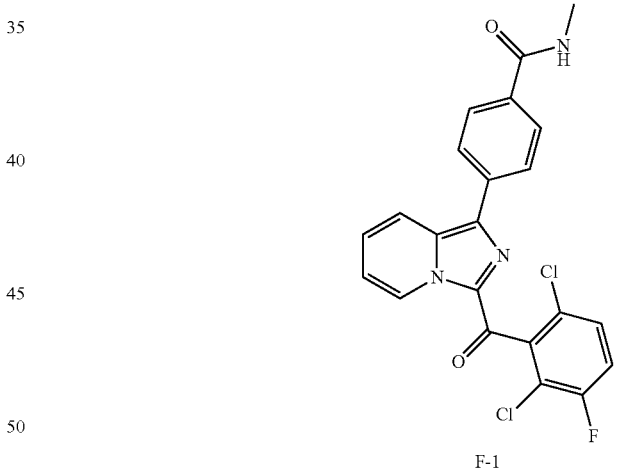

F-1

Step I: F-1: 4-[3-(2,6-dichloro-3-fluoro-benzoyl)imidazo[1,5-a]pyridine-1-yl]-N-methyl-benzamide To a stirred mixture of 4-[3-(2,6-dichloro-3-fluoro-benzoyl)indolizin-1-yl]benzoic acid (0.050 g, 0.116 mmol), methyl amine in 2M in THF (0.175 ml, 0.35 mmol) and triethylamine (0.045 mL, 0.350 mmol) in dry CH₂Cl₂ (5 mL) was stirred at room temperature for 15 min. To that Propylphosphonic anhydride (T3P) (0.073 mL, 0.23 mmol) was added. The reaction mixture was stirred overnight at room temperature. After completion of the reaction, it was quenched by the addition of water and aqueous phase was extracted with CH₂Cl₂ (3×10 mL). Combined organic layer was washed with saturated aqueous NaHCO$_3$ solution, brine, dried over Na$_2$SO$_4$, filtered and the solvent was removed to give a solid. The crude product was purified by silica gel column chromatography (5% MeOH in DCM) to provide title compound F-1 (0.048 g, 28%). LCMS: m/z 441.2 (M+1)$^+$. $^1$H NMR (DMSO-d$_6$, 400 MHz) δ 2.79 (d, J=4.4 Hz, 3H), 7.33-7.36 (m, 1H), 7.54 (s, 1H), 7.58-7.73 (m, 5H), 7.89-7.91 (m, 2H), 8.13-8.16 (m, 1H), 8.46-8.47 (m, 1H), 9.94 (d, J=7.2 Hz, 1H)

Following compounds were prepared from its corresponding intermediate using the same sequence of procedures as used for preparation of Example F-1 from A-19

| No | IUPAC name | Characterization | INT used |
|---|---|---|---|
| F-2 | 4-[3-(2,6-dichloro-3-fluoro-benzoyl)indolizin-1-yl]-N,N-dimethyl-benzamide | LCMS: m/z 441.2 (M + 1)$^+$. $^1$H NMR (DMSO-d$_6$, 400 MHz) δ 2.97 (s, 6H), 7.32-7.35 (m, 1H), 7.45-7.47 (m, 2H), 7.50 (s, 1H), 7.57-7.68 (m, 1H), 7.69-7.77 (m, 4H), 8.13 (d, J = 9.2 Hz, 1H), 9.93 (d, J = 6.8 Hz, 1H) | A-19 |
| F-3 | [4-[3-(2,6-dichloro-3-fluoro-benzoyl)indolizin-1-yl]phenyl]-morpholino-methanone | LCMS: m/z 497.1 (M + 1)$^+$. $^1$H NMR (DMSO-d$_6$, 400 MHz) δ 3.53-3.65 (m, 8H), 7.34 (t, J = 6.8 Hz, 1H) 7.46-7.50 (m, 3H), 7.57-7.61 (m, 1H), 7.64-7.72 (m, 4H), 8.13 (d, J = 8.8 Hz, 1H), 9.93 (d, J = 6.8 Hz, 1H) | A-19 |

Synthesis of G-1: 1-[4-[3-(2,6-dichlorobenzoyl) imidazo[1,5-a]pyridin-1-yl]-3,6-dihydro-2H-pyridin-1-yl]-3,3,3-trifluoro-propan-1-one

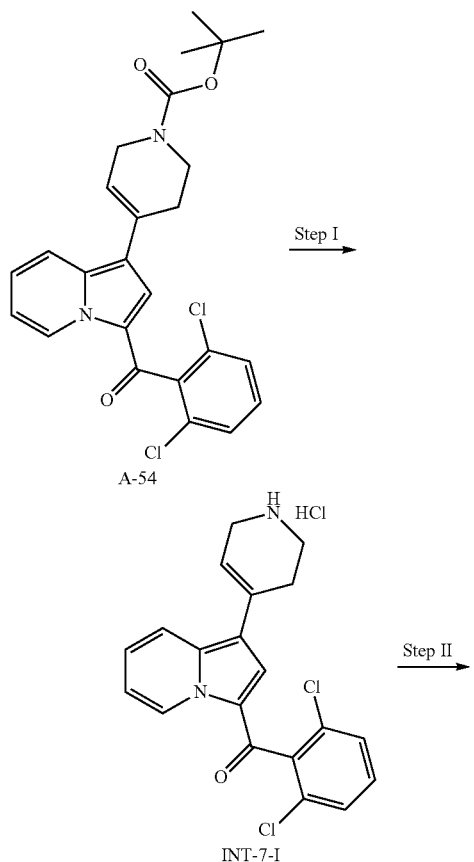

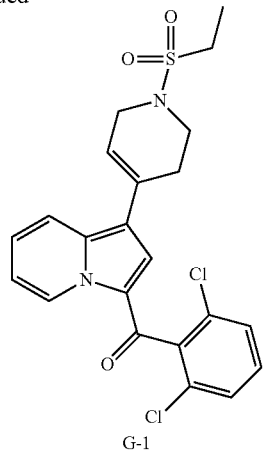

G-1

Step-I: INT-7-I: (2,6-dichlorophenyl)-[1-(1,2,3,6-tetrahydropyridin-4-yl)indolizin-3-yl]methanone hydrochloride To a stirred solution of compound A-54 (0.180 mg, 1.6 mmol) in DCM (4 mL) was added 4M dioxane HCl (1.5 mL) and the reaction mixture was stirred for 3 h. The reaction mixture was evaporated to dryness gave the solid crude mass. The solid mass was triturated with diethyl ether afforded the pure title compound as hydrochloride salt (120 mg, 98%). LCMS: m/z 372 (M+1)$^+$.

Step-II: G-1: (2,6-dichlorophenyl)-[1-(1-ethylsulfonyl-3,6-dihydro-2H-pyridin-4-yl)indolizin-3-yl]methanone To a stirred mixture of (2,6-dichlorophenyl)-[1-(1,2,3,6-tetrahydropyridin-4-yl)indolizin-3-yl]methanone hydrochloride salt (0.060 g, 0.16 mmol), triethylamine (0.062 mL, 0.48 mmol) and in dry CH$_2$Cl$_2$ (5 mL), Ethanesulfonyl chloride (0.02 ml, 0.24 mmol) was added at room temperature. The reaction mixture was stirred 2 h at room temperature. After completion of the reaction, it was quenched by the addition of water and aqueous phase was extracted with CH$_2$Cl$_2$ (3×10 mL). Combined organic layer was washed with saturated aqueous NaHCO$_3$ solution, brine, dried over Na$_2$SO$_4$, filtered and the solvent was removed to give a solid. The crude product was purified by silica gel column chromatography (30% EtOAc in hexane) to provide title compound G-2 (0.020 g, 28%). LCMS: m/z 463.1 (M+1)$^+$. $^1$H NMR (DMSO-d$_6$, 400 MHz) δ 1.39 (t, J=7.6 Hz, 3H), 2.57-2.58 (m, 2H), 3.02 (t, J=7.6 Hz, 2H), 3.55 (t, J=5.6 Hz, 2H), 4.02-4.04 (m 2H), 5.97-5.97 (m, 1H), 6.85 (s, 1H), 6.70-7.07 (m, 1H), 7.31-7.35 (m, 2H), 7.39-7.4 (m, 2H), 7.80-7.82 (m, 1H), 10.05 (d, J=7.6 Hz, 1H)

Following compounds were prepared from its corresponding intermediate using the same sequence of procedures as used for preparation of Example G-2 from A-54

| No | IUPAC name | Characterization | INT used |
|---|---|---|---|
| G-2 | (2,6-dichloro-3-fluoro-phenyl)-[1-(1-ethylsulfonyl- | LCMS: m/z 481.2 (M + 1)$^+$. $^1$H NMR (CDCl$_3$, 400 MHz) δ 1.38 (t, J = 7.2 Hz, 3H), 2.46-2.48 (m, 2H), 3.62 (q, J = 7.2 Hz, 2H), 3.48-3.52 (m, 2H), 4.04- | A-55 |

| No | IUPAC name | Characterization | INT used |
|---|---|---|---|
| | 3,6-dihydro-2H-pyridin-5-yl)indolizin-3-yl]methanone | 4.06 (m, 2H), 6.13-6.15 (m, 1H), 6.85 (s, 1H), 7.06-7.09 (m, 1H), 7.22-7.24 (m, 1H), 7.33-7.40 (m, 2H), 7.81-7.83 (m, 1H), 10.00 (d, J = 7.2 Hz, 1H) | |

Synthesis H-1: 4-[3-[2-chloro-6-(trifluoromethyl)benzoyl]-5,6,7,8-tetrahydroindolizin-1-yl]benzoic acid

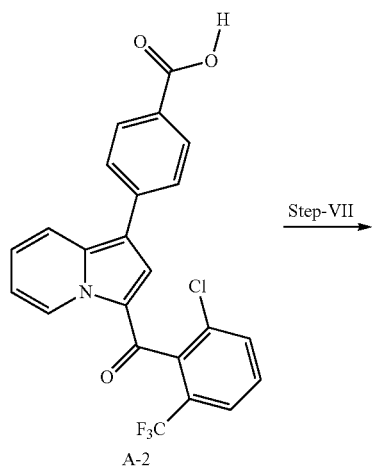

Step-I: H-1: 4-[3-[2-chloro-6-(trifluoromethyl)benzoyl]-5,6,7,8-tetrahydroindolizin-1-yl]benzoic acid A stirred solution of 4-[3-[2-chloro-6-(trifluoromethyl)benzoyl]indolizin-1-yl]benzoic acid A-2 (0.48 g, 0.24 mol) in acetic acid (3 mL), platinum oxide (10 mg) was added at room temperature. The reaction was mixture was stirred under hydrogen balloon pressure at room temperature for 3 h (monitored by LCMS). The mixture was filtered through Celite, washed with methanol and solvent was evaporated under vacuum to yield A-3 (20 g, 40%) as a yellowish solid. LCMS: m/z 448.1 (M+1)$^+$. $^1$H NMR (DMSO-d$_6$, 400 MHz) δ 1.82-1.85 (m, 2H), 2.00-2.02 (m, 2H), 3.03 (t, J=6.4 Hz, 2H), 4.43-4.49 (m, 2H), 6.67 (s, 1H), 7.47 (d, J=8.4 Hz, 2H), 7.73 (t, J=8.0 Hz, 1H), 7.85-7.92 (m, 4H), 12.95 (s, 1H).

Following compounds were prepared from its corresponding intermediate using the same sequence of procedures as used for preparation of Example H-1 from A-2

| No | IUPAC name | Characterization | INT used |
|---|---|---|---|
| H-2 | 4-[3-(2,6-dichlorobenzoyl)-2-methyl-5,6,7,8-tetrahydroindolizin-1-yl]-3-fluoro-benzoic acid | LCMS: m/z 446 (M + 1)+. 1H NMR (DMSO-d6, 400 MHz) δ 1.37 (s, 3H), 1.75-1.77 (m, 2H), 1.97-1.99 (m, 2H), 2.58-2.71 (m, 2H), 4.43-4.46 (m, 2H), 7.40-7.44 (m, 1H), 7.46-7.51 (m, 1H), 7.57-7.59 (m, 2H), 7.69-7.72 (m, 1H), 7.76-7.78 (m, 1H), 13.02 (s, 1H), | C-2 |
| H-3 | 4-[3-(2,6-dichloro-3-fluoro-benzoyl)-5,6,7,8 tetrahydroindolizin-1-yl]benzoic acid | LCMS: m/z 497.1 (M + 1)+. 1H NMR (DMSO-d6, 400 MHz) δ 1.83-1.86 (m, 2H), 1.98-2.03 (m, 2H), 3.03 (t, J = 5.6 Hz, 1H), 4.41 (t, J = 5.6 Hz, 1H), 6.90 (s, 1H), 7.50-7.53 (m, 2H), 7.56-7.65 (m, 2H), 7.88-7.90 (m, 2H), 12.96 (bs, 1H) | A-19 |
| H-4 | 4-[3-[2-chloro-6-(trifluoromethyl)benzoyl]-5,6,7,8-tetrahydroindolizin-1-yl]-3-fluoro-benzoic acid | LCMS: m/z 466 (M + 1)$^+$. $^1$H NMR (DMSO-d$_6$, 400 MHz) δ 1.81 (bs, 2H), 2.01-2.03 (m, 2H), 2.87 (bs, 2H), 4.41-4.53 (m, 2H), 6.52 (s, 1H), 7.48 (t, J = 8.0 Hz, 1H), 7.64 (d, J = 11.2 Hz, 1H), 7.47-7.70 (m, 2H), 7.85 (d, J = 8.4 Hz, 1H), 7.90 (d, J = 8.4 Hz, 1H), 13.03 (bs, 1H) | A-12 |
| H-5 | 4-[3-(2-chloro-6-methyl-benzoyl)-5,6,7,8-tetrahydroindolizin-1-yl]benzoic acid | LCMS: m/z 384.1 (M + 1)$^+$. $^1$H NMR (DMSO-d$_6$, 400 MHz) δ 1.83 (bs, 2H), 2.00-2.08 (m, 2H), 2.21 (s, 3H), 3.00 (bs, 2H), 4.49 (bs, 2H), 6.55 (s, 1H), 7.29-7.41 (m, 5H), 7.86 (d, J = 8.4 Hz, 2H), 13.01 (bs, 1H) | A-16 |

Synthesis of I-1: Sodium 4-[3-(2,6-dichloro-3-fluoro-benzoyl)imidazo[1,5-a]pyridin-1-yl]benzoate

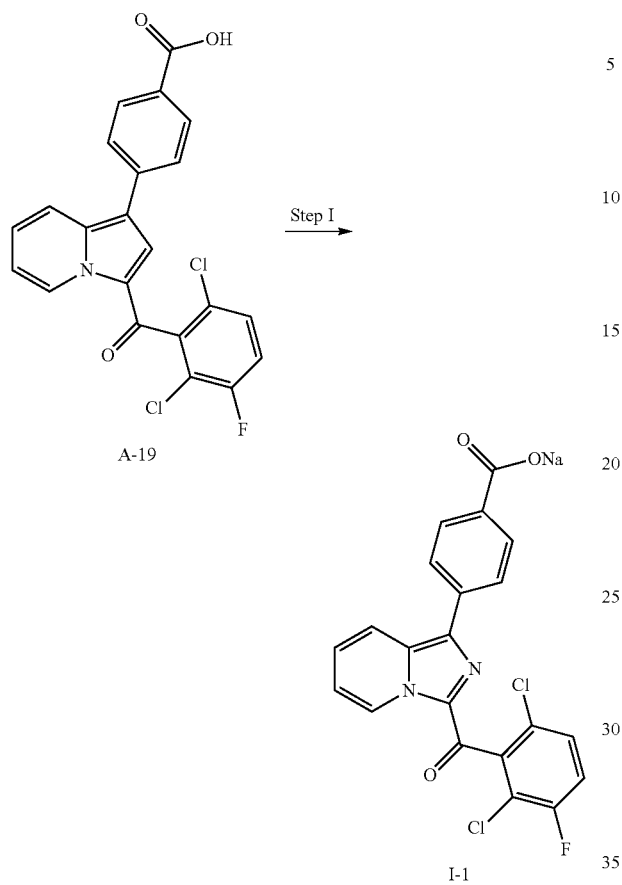

Step I: I-1: Sodium 4-[3-(2,6-dichloro-3-fluoro-benzoyl)imidazo[1,5-a]pyridine-1-yl]benzoate A solution of 4-[3-(2,6-dichloro-3-fluoro-benzoyl)indolizin-1-yl]benzoic acid (0.3 g, 0.70 mmol) in THF (4 ml), NaOH (0.028 g, 0.70 mmol) in 2 mL water was added at room temperature and the mixture was stirred for 0.5 h. After completion of salt formation, the solvents were removed under reduced pressure and then in lyophilizer to afford the title compound I-1 (0.300 g, 95%). LCMS: m/z 428.0 (M+1)$^+$. $^1$H NMR (DMSO-d$_6$, 400 MHz) δ 7.29-7.33 (m, 1H), 7.40 (s, 1H), 7.48 (d, J=8.0 Hz, 2H), 7.49-7.59 (m, 1H), 7.61-7.69 (m, 2H), 7.88 (dd, J=1.6, 8.0 Hz, 2H), 8.10 (d, J=4.8 Hz, 1H), 9.92 (d, J=6.8 Hz, 1H).

Synthesis J-1: 4-[3-[(2-chloro-6-fluoro-phenyl)methyl]indolizin-1-yl]benzoic acid

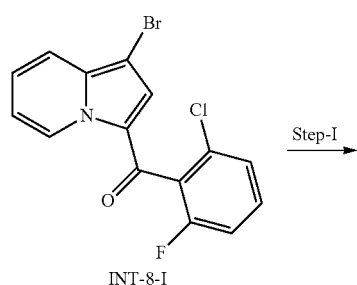

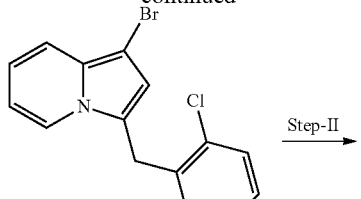

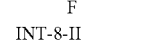

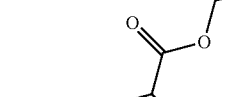

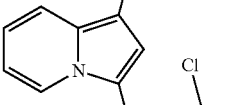

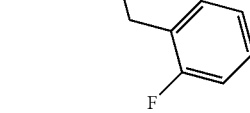

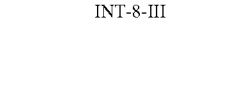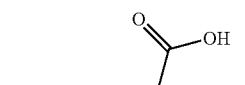

Step-I: INT-8-II: 1-bromo-3-[(2-chloro-6-fluoro-phenyl)methyl]indolizine

To compound (1-bromoindolizin-3-yl)-(2-chloro-6-fluoro-phenyl)methanone (100 mg, 0.29 mmol) and NaBH$_4$ (54 mg, 1.45 mmol) in 10 mL dry THF, was added AlCl$_3$ (116 mg, 0.87 mmol) in small portions (reaction mixture immediately turns an orange color). The reaction was refluxed for 1 hour (orange color gradually faded). After completion of reaction, it was cooled to room temperature and poured onto 20 mL EtOAc and 20 mL ice cold H$_2$O in a separatory funnel. The layers were separated, and the aqueous layer was extracted with 3×10 mL EtOAc. The organic layers were combined, dried over MgSO$_4$, filtered, and concentrated by rotary evaporation. The crude material was purified by column chromatography over silica gel (20% EtOAc: Hexane) to afford compound. Yield (62 mg, 62%), LCMS: m/z 351.01 (M+1)$^+$ Step-II: INT-8-III: ethyl 4-[3-[(2-chloro-6-fluoro-phenyl)methyl]indolizin-1-yl]benzoate Title compound was synthesized as described for the synthesis of A-1. LCMS: m/z 408.01 (M+1)$^+$ Step III: J-1: 4-[3-[(2-chloro-6-fluoro-phenyl)methyl]indolizin-1-yl]benzoic acid Title compound was synthesized as described for the synthesis of A-2. LCMS: m/z 380.1 $^1$H NMR (DMSO-d6, 400 MHz) δ 4.34 (s, 2H), 6.46 (s, 1H), 6.80-6.84 (m, 1H), 6.93-6.97 (m, 1H), 7.31-7.36 (m, 1H), 7.44-7.46 (m, 2H), 7.61 (d, J=8.0 Hz, 2H), 7.86-7.92 (m, 3H), 8.35 (d, J=7.2 Hz, 1H), 12.96 (s, 1H).

The list of examples below, but not limited to these, can also be synthesized following the synthetic routes described above:
- 4-[3-(2,6-dichlorobenzoyl)indolizin-1-yl]cyclohexanecarboxylic acid;
- 4-[3-[2-chloro-6-(trifluoromethyl)benzoyl]indolizin-1-yl]cyclohexanecarboxylic acid;
- 4-[3-[2-chloro-6-(trifluoromethyl)benzoyl]indolizin-1-yl]cyclohex-3-ene-1-carboxylic acid;
- 4-[3-(2,6-dichlorobenzoyl)indolizin-1-yl]cyclohexanecarboxylic acid;
- 1-[3-[2-chloro-6-(trifluoromethyl)benzoyl]indolizin-1-yl]piperidine-4-carboxylic acid;
- 4-[3-(2,6-dichlorobenzoyl)indolizin-1-yl]cyclohexanecarboxylic acid;
- 5-[3-(2,6-dichlorobenzoyl)indolizin-1-yl]norbornane-2-carboxylic acid;
- 4-[3-(2,6-dichlorobenzoyl)indolizin-1-yl]norbornane-1-carboxylic acid;
- 8-[3-[2-chloro-6-(trifluoromethyl)benzoyl]indolizin-1-yl]spiro[2.5]octane-5-carboxylic acid;
- 5-[3-[2-chloro-6-(trifluoromethyl)benzoyl]indolizin-1-yl]spiro[2.5]octane-8-carboxylic acid;
- 4-[3-(2,6-dichlorobenzoyl)indolizin-1-yl]-2-hydroxy-cyclohexanecarboxylic acid;
- 4-[3-[2-chloro-6-(trifluoromethyl)benzoyl]indolizin-1-yl]-3-hydroxy-cyclohexanecarboxylic acid;
- 4-[3-(2,6-dichlorobenzoyl)indolizin-1-yl]-5-fluoro-2-hydroxy-benzoic acid;
- 4-[3-(2,6-dichlorobenzoyl)-8-fluoro-indolizin-1-yl]-5-fluoro-2-hydroxy-benzoic acid;
- 4-[3-[2-chloro-6-(1-hydroxycyclobutyl)benzoyl]indolizin-1-yl]benzoic acid;
- 4-[3-[2-chloro-6-(trifluoromethyl)benzoyl]indolizin-1-yl]-2-fluoro-5-hydroxy-benzoic acid;
- 4-[3-(2,6-dichlorobenzoyl)-6-(1H-1,2,4-triazol-5-yl)indolizin-1-yl]cyclohexanecarboxylic acid;
- 4-[3-[(2-chloro-6-methyl-phenyl)methyl]indolizin-1-yl]benzoic acid;
- 4-[3-[(2,6-dichlorophenyl)methyl]-8-fluoro-indolizin-1-yl]-2-fluoro-benzoic acid;
- 4-[3-[(2,3,6-trichlorophenyl)methyl]indolizin-1-yl]benzoic acid;
- 4-[3-[[2-chloro-6-(trifluoromethyl)phenyl]methyl]indolizin-1-yl]cyclohex-3-ene-1-carboxylic acid;
- 1-[3-[[2-chloro-6-(trifluoromethyl)phenyl]methyl]indolizin-1-yl]piperidine-4-carboxylic acid;
- (1R)-4-[3-[[2-chloro-6-(trifluoromethyl)phenyl]methyl]indolizin-1-yl]cyclohex-3-ene-1-carboxylic acid;
- 4-[3-[(2,6-dichlorophenyl)-hydroxy-methyl]indolizin-1-yl]benzoic acid;
- 4-[3-[(2,6-dichlorophenyl)-difluoro-methyl]indolizin-1-yl]benzoic acid;
- 4-[3-[1-(2,6-dichlorophenyl)-1-methyl-ethyl]indolizin-1-yl]benzoic acid;
- 4-[3-[1-(2,6-dichlorophenyl)cyclopropyl]indolizin-1-yl]benzoic acid;
- 4-[3-[3-(2,6-dichlorophenyl)oxetan-3-yl]indolizin-1-yl]benzoic acid;
- 4-[3-(2,6-dichlorophenyl)sulfanylindolizin-1-yl]benzoic acid;
- 4-[3-(2,6-dichlorophenyl)sulfonylindolizin-1-yl]benzoic acid;
- 4-[3-(2,6-dichloroanilino)indolizin-1-yl]benzoic acid;
- 4-[3-(2,6-dichloro-N-methyl-anilino)indolizin-1-yl]benzoic acid;
- 4-[1-[(2,6-dichlorophenyl)methyl]indolizin-3-yl]benzoic acid;
- 4-[1-[(2,6-dichlorophenyl)-difluoro-methyl]indolizin-3-yl]benzoic acid;
- 4-[1-[1-(2,6-dichlorophenyl)cyclopropyl]indolizin-3-yl]benzoic acid;
- 4-[6-[(2,6-dichlorophenyl)methyl]pyrrolo[1,2-a]pyrimidin-8-yl]benzoic acid;
- 4-[6-[(2-chloro-6-methyl-phenyl)-difluoro-methyl]pyrrolo[1,2-a]pyrimidin-8-yl]benzoic acid;
- 6-[6-[1-(2,6-dichlorophenyl)-1-methyl-ethyl]pyrrolo[1,2-a]pyrimidin-8-yl]pyridine-3-carboxylic acid;
- 6-[6-[1-(2,6-dichlorophenyl)cyclopropyl]pyrrolo[1,2-a]pyrimidin-8-yl]pyridine-3-carboxylic acid;
- 4-[6-(2,6-dichlorobenzoyl)pyrrolo[1,2-a]pyrimidin-8-yl]benzoic acid;
- 4-[6-(2,6-dichlorobenzoyl)pyrrolo[1,2-a]pyrazin-8-yl]benzoic acid;
- 4-[7-(2,6-dichlorobenzoyl)pyrrolo[1,2-c]pyrimidin-5-yl]benzoic acid;
- 6-[6-(2,6-dichlorophenyl)sulfonylpyrrolo[1,2-a]pyrimidin-8-yl]pyridine-3-carboxylic acid;
- 4-[6-(2,6-dichlorophenoxy)pyrrolo[1,2-a]pyrimidin-8-yl]benzoic acid;
- 5-[6-(2,6-dichloroanilino)pyrrolo[1,2-a]pyrimidin-8-yl]pyridine-2-carboxylic acid;
- 8-(4-carboxyphenyl)-6-(2,6-dichlorobenzoyl)pyrrolo[1,2-a]pyrimidine-3-carboxylic acid;
- 4-[3-[2-chloro-6-(trifluoromethyl)benzoyl]-6-(morpholine-4-carbonyl)indolizin-1-yl]-2,5-difluoro-benzoic acid;
- 4-[3-(2,6-difluorobenzoyl)-5,6,7,8-tetrahydroimidazo[1,5-a]yridine-1-yl]cyclohexanecarboxylic acid;
- 4-[3-(2-chloro-6-methoxy-benzoyl)-5,6,7,8-tetrahydroindolizin-1-yl]cyclohex-3-ene-1-carboxylic acid;
- 4-[3-(2,6-dichlorobenzoyl)indolizin-1-yl]cyclohex-3-ene-1-carboxylic acid;
- 1-[3-(2,6-dichlorobenzoyl)indolizin-1-yl]piperidine-4-carboxylic acid;
- 4-[3-[2-chloro-6-(trifluoromethyl)benzoyl]indolizin-1-yl]benzoic acid;
- 4-[3-(2-bromo-6-chloro-benzoyl)indolizin-1-yl]benzoic acid;
- 4-[3-(2,6-dichlorobenzoyl)-5,6,7,8-tetrahydroindolizin-1-yl]-2-fluoro-benzoic acid;
- 4-[3-(2,6-dichlorobenzoyl)-5,6,7,8-tetrahydroindolizin-1-yl]benzoic acid;
- 4-[3-[2-chloro-6-(trifluoromethyl)benzoyl]-5,6,7,8-tetrahydroindolizin-1-yl]-2-fluoro-benzoic acid;
- 4-[3-[2-chloro-6-(trifluoromethyl)benzoyl]spiro[6,7-dihydro-5H-indolizine-8,1'-cyclopropane]-1-yl]-2-fluoro-benzoic acid;

4-[3-[2-chloro-6-(trifluoromethyl)benzoyl]spiro[7,8-dihydro-6H-indolizine-5,1'-cyclopropane]-1-yl]-2-fluorobenzoic acid;
4-[3-(2-Chloro-6-trifluoromethyl-benzoyl)-2-aza-tricyclo[6.1.1.0*2,6*]deca-3,5-dien-5-yl]-2-fluoro-benzoic acid;
4-[3-(3,5-dichloropyridine-4-carbonyl)indolizin-1-yl]benzoic acid;
4-[3-(2,6-dichlorobenzoyl)indolizin-1-yl]-1H-imidazole-2-carboxylic acid;
6-[3-(2-chloro-6-cyclopropyl-benzoyl)indolizin-1-yl]pyridine-3-carboxylic acid;
2-[3-(2,6-dichloro-4-fluoro-benzoyl)indolizin-1-yl]pyrimidine-5-carboxylic acid;
4-[3-(2-chloro-6-fluoro-benzoyl)-8-cyano-indolizin-1-yl]-3-fluoro-benzoic acid;
4-[3-(2-chloro-6-fluoro-benzoyl)-5-cyano-indolizin-1-yl]-2-fluoro-benzoic acid;
6-[3-[(2,4,6-trichlorophenyl)methyl]indolizin-1-yl]pyridine-3-carboxylic acid;
5-[3-[2-chloro-6-(trifluoromethyl)benzoyl]indolizin-1-yl]pyrazine-2-carboxylic acid;
4-[6-[2-chloro-6-(trifluoromethyl)benzoyl]pyrrolo[1,2-a]pyrimidin-8-yl]cyclohexanecarboxylic acid;
4-[3-[2-chloro-6-(trifluoromethyl)benzoyl]spiro[6,8-dihydro-5H-indolizine-7,1'-cyclopropane]-1-yl]benzoic acid;
4-[3-(2,6-dichloro-3-fluoro-benzoyl)indolizin-1-yl]benzenesulfonic acid;
4-[3-(2,6-dichloro-3-fluoro-benzoyl)indolizin-1-yl]-3-fluoro-benzenesulfonic acid;
4-[3-(2,6-dichloro-3-fluoro-benzoyl)-6-(dimethylcarbamoyl)indolizin-1-yl]benzenesulfonic acid;
4-[3-(2,6-dichloro-3-fluoro-benzoyl)-5,6,7,8-tetrahydroindolizin-1-yl]-3-fluoro-benzenesulfonic acid and
4-[3-(2,6-dichloro-3-fluoro-benzoyl)-6-(dimethylcarbamoyl)-5,6,7,8-tetrahydroindolizin-1-yl]benzenesulfonic acid.

Biological Activity

TR-FRET Binding Assay Protocol:

The binding affinity of the compounds to the ROR ligand binding domain (LBD) was evaluated using a LanthaScreen time-resolved FRET (TR-FRET) assay (LanthaScreen® TR-FRET RORγ Co activator Assay Kit, rabbit, Invitrogen, A15147). Briefly, varying concentrations of NCEs were incubated with fluorescein-D22 co activator peptide, LanthaScreen™ Tb anti-GST antibody and GST tagged RORγ LBD in a 384-well low-volume assay plate (Corning® 384 well plates, low volume, Sigma-Aldrich, CLS3677). Each reaction consisted of 150 nM fluorescein-D22 co activator peptide, 2 nM Tb anti-GST antibody, 2 nM RORγ LBD and compounds at desired concentrations diluted with Co regulator Buffer D (proprietary buffer, pH 7.5), where the final assay volume was 20 μL and concentration of DMSO was adjusted to 1%. Appropriate controls included in the assay, vehicle control was the positive control and negative control was evaluated by incubating the reaction in absence of RORγ LBD. The reaction was incubated at room temperature for 1 hour in dark. Upon incubation, the Tb-anti-GST antibody indirectly labels the nuclear receptor by binding to the GST tag. Binding of the antagonist to the RORγ LBD causes a conformational change that result in a decrease in the affinity of the RORγ for a co activator peptide. The separation of the fluorescently labeled co activator peptide from the RORγ with the terbium-labeled antibody causes a decrease in the TR-FRET signal. The plate was read in Flex station 3 in TR-FRET mode with an excitation wavelength of 332 nm and emission wavelengths of 490 nm and 520 nm.

Data was analyzed by calculating the TR-FRET ratio by dividing the emission at 520 nm by the emission at 495 nm and determining the $IC_{50}$ value by fitting the data using an equation for a sigmoidal dose response (varying slope), as provided by Graph Pad™ Prism. Vehicle control (DMSO) was normalized to 0% inhibition and DMSO control in the absence of RORγ LBD to 100% inhibition.

RORγt Transactivation Reporter Assay Protocol:

The inhibition of RORγt activity in cells was evaluated using a GAL4-UAS reporter system in HEK293T cells employing a luciferase read out. RORγt ligand binding domain (LBD) was cloned into the pFN26A (BIND) vector (Promega #E138A) containing yeast GAL4-DBD to form a RORγt LBD-GAL4 DBD fusion construct. This vector also contained a Renilla Luciferase reporter expressed under a SV40 promoter which was used as a control for transfection efficiency. A transcriptional reporter expression construct pGL4.35 (Promega #E137A) was used to monitor RORγt LBD-GAL4 activity. This construct contained nine repeats of GAL4 binding site/upstream activating sequence (UAS) controlling expression of a firefly luciferase reporter Luc2P. When transfected together in cells, the RORγ-LBD-DBD fusion protein drives expression of the luciferase reporter.

For the assay, HEK293T cells were plated in a flat bottom 96 well plate at a density of 25,000 cells/well/100 ul of DMEM high glucose medium (Sigma D5648) containing 10% FBS and antibiotic. Cells were incubated overnight at 37 C/5% CO2. The next day, medium from the wells was removed and replaced with 30 ul of OptiMEM® (Invitrogen #31985070). 100 ng each of pBIND RORγ LBD-DBD and pGL4.35 reporter plasmids was transfected in HEK293T cells using Lipofectamine 2000 (Invitrogen #11668-019) where 10 ul of transfection complex was added to the each well. Control transfections were performed with an empty pFN26A vector and pGL4.35 vector. The transfected cells were incubated for 5 hours at 37 C/5% CO2. After incubation, 40 ul of DMEM high glucose medium without FBS, with antibiotic was added to each well.

A 10 mM stock solution of test compound prepared in 100% DMSO was first diluted in DMSO and then in DMEM medium without FBS to give the required final compound concentration. Concentration of DMSO in the test compound solution was 0.4%. 20 ul of diluted compound solution was added to each well. Cells were incubated overnight (18-24 hours) at 37 C/5% CO2. The next day, luciferase assay was performed using the Dual Glo® Luciferase Assay System (Promega #E2940). Briefly, medium was removed from the wells and replaced with 40 ul 1× Passive Lysis Buffer (Promega #E1941). Plate was incubated at room temperature on a plate shaker at 1000 rpm for 40 min. After incubation, plate was centrifuged at 1000 rpm for 2 min. 20 ul of the lysate was transferred from each well to that of solid white half area 96 well plate (Costar #3693). Dual Glo® Reagent was thawed to room temperature and 20 ul was added to each well containing lysate. Plate was centrifuged at 1000 rpm/2 min and incubated at room temperature on a plate shaker at 600 rpm/25 min. Firefly luciferase signal was measured on a Tecan Safire2. After measurement, 20 ul of Dual Glo® Stop Glo® Reagent was added to each well. Plate was centrifuged at 1000 rpm/2 min and incubated at room temperature on a plate shaker at 600 rpm/25 min. Renilla luciferase signal was measured on Tecan Safire 2. $IC_{50}$ values for test compounds were calculated from the normalized luciferase signal data using GraphPad Prism software.

Data for representative compounds of the present disclosure are given below in Table 1:

TABLE 1

Transactivation assay with GAL4-DBD/RORγ-LBD: IC50 values:

| Example No | Transactivation assay with GAL4-DBD/RORγ-LBD IC50 (nM) |
|---|---|
| A-1 | <500 |
| A-2 | <500 |
| A-3 | <500 |
| A-4 | <500 |
| A-5 | <500 |
| A-6 | <500 |
| A-7 | <500 |
| A-8 | <500 |
| A-9 | <500 |
| A-10 | >5000 |
| A-11 | <500 |
| A-12 | <500 |
| A-13 | <500 |
| A-14 | <500 |
| A-15 | <500 |
| A-16 | <500 |
| A-17 | <500 |
| A-18 | <500 |
| A-19 | <500 |
| A-20 | >5000 |
| A-21 | <500 |
| A-22 | <500 |
| A-23 | <500 |
| A-24 | <500 |
| A-25 | <500 |
| A-26 | <500 |
| A-27 | <500 |
| A-28 | <500 |
| A-29 | <500 |
| A-30 | <500 |
| A-31 | <500 |
| A-32 | <500 |
| A-33 | <500 |
| A-34 | <500 |
| A-35 | <500 |
| A-36 | <500 |
| A-37 | <500 |
| A-38 | <500 |
| A-39 | <500 |
| A-40 | <500 |
| A-41 | <500 |
| A-42 | <500 |
| A-43 | <500 |
| A-44 | <500 |
| A-45 | <500 |
| A-46 | <500 |
| A-47 | <500 |
| A-48 | <500 |
| A-49 | <500 |
| A-50 | <5000 |
| A-51 | <500 |
| A-52 | <1000 |
| A-53 | <5000 |
| A-54 | >5000 |
| A-55 | >5000 |
| A-56 | <500 |
| A-57 | >5000 |
| A-58 | <500 |
| A-59 | <500 |
| A-60 | <500 |
| A-61 | <500 |
| A-62 | <500 |
| A-63 | <5000 |
| A-64 | <500 |
| A-65 | <500 |
| A-66 | <500 |
| B-1 | <500 |
| B-2 | <500 |
| B-3 | <500 |
| B-4 | <500 |
| B-5 | <500 |
| B-6 | <500 |
| C-1 | <500 |
| C-2 | <500 |
| C-3 | <500 |
| C-4 | <500 |
| C-5 | <500 |
| C-6 | <500 |
| C-7 | <500 |
| C-8 | <500 |
| C-9 | <500 |
| C-10 | <5000 |
| D-1 | <500 |
| D-2 | <500 |
| D-3 | <1000 |
| D-4 | <1000 |
| D-5 | <500 |
| D-6 | <500 |
| D-7 | >5000 |
| D-8 | >5000 |
| D-9 | <5000 |
| D-10 | <500 |
| D-11 | <500 |
| D-12 | <500 |
| D-13 | <5000 |
| D-14 | <500 |
| E-1 | <500 |
| E-2 | <5000 |
| E-3 | >5000 |
| F-1 | >5000 |
| F-2 | >5000 |
| F-3 | >5000 |
| G-1 | >5000 |
| G-2 | >5000 |
| H-1 | <500 |
| H-2 | <500 |
| H-3 | >5000 |
| H-4 | >5000 |
| H-5 | <500 |
| I-1 | <500 |
| J-1 | <500 |

We claim:

1. A compound represented by Formula I

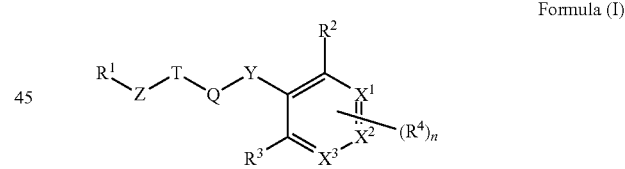

Formula (I)

their tautomers, polymorphs, stereoisomers, prodrugs, solvates, and pharmaceutically acceptable salts thereof, wherein, Q is

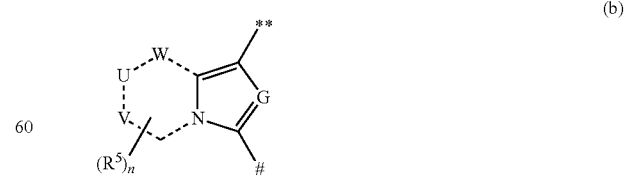

(b)

wherein ** represents point of attachment of T;
\# represents point of attachment of Y;
each "- - - - - -" is independently a single or double bond;

U, V and W are independently selected from the group consisting of CR' and CR'R'';

G is CR';

R' and R'' are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R'' taken together form a monocyclic or a bicyclic ring system which is saturated or partially unsaturated and optionally have additional heteroatoms selected from the group consisting of O, N and S, said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

T and Y are independently defined as follows:

a) T is a monocyclic or a bicyclic carbocyclic ring system which is saturated, unsaturated or partially unsaturated, and which is optionally substituted with 1 to 4 substituents independently selected from the group consisting of halo, alkyl, alkenyl, alkynyl, nitro, cyano, —(CR$^a$R$^b$)$_n$OR$^6$, —(CR$^a$R$^b$)$_n$SR$^6$, —(CR$^a$R$^b$)$_n$NR$^7$R$^8$, oxo, alkylsulfonyl, —(CR$^a$R$^b$)$_n$COOR$^6$, —(CR$^a$R$^b$)$_n$C(O)NR$^7$R$^8$, cycloalkyl, cycloalkylalkyl, aryl, arylalkyl, heterocyclyl, heterocyclylalkyl, heteroaryl, and heteroarylalkyl;

Y is a group selected from the group consisting of —O—, —S(O)$_p$—, —N(R$^7$)—, —C(O)—, —C(S)— and —(CR$^a$R$^b$)—; or b) T is a monocyclic or a bicyclic ring system which is saturated, unsaturated or partially unsaturated, and which optionally comprises one or more additional heteroatoms selected from the group consisting of O, N and S, and is optionally substituted with 1 to 4 substituents independently selected from the group consisting of halo, alkyl, alkenyl, alkynyl, nitro, cyano, —(CR$^a$R$^b$)$_n$OR$^6$, —(CR$^a$R$^b$)$_n$SR$^6$, —(CR$^a$R$^b$)$_n$NR$^7$R$^8$, oxo, alkylsulfonyl, —(CR$^a$R$^b$)$_n$COOR$^6$, —(CR$^a$R$^b$)$_n$C(O)NR$^7$R$^8$, cycloalkyl, cycloalkylalkyl, aryl, arylalkyl, heterocyclyl, heterocyclylalkyl, heteroaryl, and heteroarylalkyl;

Y is —C(O)— or —C(S)—;

R$^a$ and R$^b$ are independently selected from the group consisting of hydrogen, —OR$^7$, halogen, haloalkyl, perhaloalkyl and alkyl; or R$^a$ and R$^b$ taken together form a monocyclic or a bicyclic ring system which is saturated or partially unsaturated and optionally have one or more additional heteroatoms selected from the group consisting of O, N and S;

X$^1$, X$^2$ and X$^3$ are each independently selected from the group consisting of N and CR$^7$;

Z is —C(O)— or —S(O)$_p$—;

R$^1$, R$^4$ and R$^5$ are independently selected from the group consisting of hydrogen, halogen, alkyl, hydroxy, alkoxy, amino, alkenyl, alkynyl, cycloalkyl, cycloalkylalkyl, heterocyclyl, heterocloalkyl, aryl, arylalkyl, heteroaryl, heteroarylalkyl, tetrazolyl, tetrazolylalkyl, mono, di or tri substituted haloalkyl, nitrile, nitro, oxo, —NR$^7$R$^8$, —OR$^7$, —S(O)$_p$R$^7$, —S(O)$_p$NR$^7$R$^8$, —NR$^7$S(O)$_p$R$^8$, —NR$^7$C(O)R$^8$, —OS(O)$_p$R$^8$, —NR$^7$C(O)OR$^8$, —(CR$^7$R$^8$)$_n$C(O)OR$^7$, —(CR$^7$R$^8$)$_n$(CO)NR$^7$R$^8$, —(CR$^7$R$^8$)$_n$S(O)$_p$NR$^7$R$^8$, —(CR$^7$R$^8$)$_n$N(R$^7$)C(O)R$^7$, —(CR$^7$R$^8$)$_n$OR$^7$, —C(R$^7$R$^8$)$_n$NR$^7$R$^8$, —C(R$^7$R$^8$)$_n$CO(R$^7$) and —S(O)$_p$C(R$^7$R$^8$)$_n$C(O)OR$^7$; or when R$^4$ or R$^5$ are more than one, then 2 R$^4$ or 2 R$^5$ independently can form a monocyclic or a bicyclic ring system which is saturated or partially unsaturated, and which optionally comprise one or more additional heteroatoms selected from the group consisting of O, N and S;

wherein each substituent is unsubstituted or substituted with 1, 2, or 3 substituents independently selected from the group consisting of alkyl, halogen, haloalkyl, perhaloalkyl, haloalkoxy, perhaloalkoxy, cyano, alkoxy, —(CR$^a$R$^b$)$_n$COOR$^7$, —(CR$^a$R$^b$)$_n$NR$^7$R$^8$, —(CR$^a$R$^b$)$_n$C(O)NR$^7$R$^8$, —S(O)$_p$R$^7$ and —SO$_3$H;

R$^2$ and R$^3$ are independently selected from the group consisting of halo, hydroxyl, cyano, C$_{1-6}$alkyl, C$_{2-6}$alkenyl, C$_{2-6}$alkynyl, haloalkyl, perhaloalkyl, cycloalkyl, cycloalkenyl, cycloalkylalkyl, aryl, and arylalkyl;

R$^6$ is selected from the group consisting of hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl and heterocyclylalkyl;

R$^7$ and R$^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R$^7$ and R$^8$ taken together form a monocyclic or a bicyclic ring system which is saturated or partially unsaturated and optionally comprises one or more additional heteroatoms selected from O, N or S, wherein said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

p=0-2; and n=0-4, wherein the prodrug is an ester, carbonate, or amide prodrug.

2. A compound of formula (I) as claimed in claim 1 or its tautomers, polymorphs, stereoisomers, prodrugs, solvate or a pharmaceutically acceptable salts thereof, wherein U, V and W are independently selected from the group consisting of CR' and CR'R'';

G is CR';

R' and R'' are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R'' taken together form a monocyclic or a bicyclic ring system which is saturated or partially unsaturated and optionally comprise one or more additional heteroatoms selected from the group consisting of O, N and S, wherein said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

T and Y are independently defined as either:
a) T is a monocyclic or a bicyclic carbocyclic ring system which is saturated, unsaturated or partially unsaturated, and which is optionally substituted with 1 to 4 substituents independently selected from the group consisting of halo, alkyl, alkenyl, alkynyl, nitro, cyano, —$(CR^aR^b)_nOR^6$, —$(CR^aR^b)_nSR^6$, —$(CR^aR^b)_nNR^7R^8$, oxo, alkylsulfonyl, —$(CR^aR^b)_nCOOR^6$, —$(CR^aR^b)_nC(O)NR^7R^8$, cycloalkyl, cycloalkylalkyl, aryl, arylalkyl, heterocyclyl, heterocyclylalkyl, heteroaryl, and heteroarylalkyl;

Y is a group selected from the group consisting of —O—, —$S(O)_p$—, —$N(R^7)$—, —C(O)—, —C(S)— and —$(CR^aR^b)$—; or b) T is a monocyclic or a bicyclic ring system which is saturated, unsaturated or partially unsaturated, and which optionally comprises one or more additional heteroatoms selected from the group consisting of O, N and S, and is optionally substituted with 1 to 4 substituents independently selected from the group consisting of halo, alkyl, alkenyl, alkynyl, nitro, cyano, —$(CR^aR^b)_nOR^6$, —$(CR^aR^b)_nSR^6$, —$(CR^aR^b)_nNR^7R^8$, oxo, alkylsulfonyl, —$(CR^aR^b)_nCOOR^6$, —$(CR^aR^b)_nC(O)NR^7R^8$, cycloalkyl, cycloalkylalkyl, aryl, arylalkyl, heterocyclyl, heterocyclylalkyl, heteroaryl, and heteroarylalkyl;

Y is —C(O)— or —C(S)—;

$R^a$ and $R^b$ are independently selected from the group consisting of hydrogen, —$OR^7$, halogen, haloalkyl, perhaloalkyl and alkyl; or $R^a$ and $R^b$ taken together form a monocyclic or a bicyclic ring system which is saturated or partially unsaturated and optionally comprises one or more additional heteroatoms selected from the group consisting of O, N and S;

$X^1$, $X^2$ and $X^3$ are each independently selected from the group consisting of N and $CR^7$;

Z is —C(O)— or —$S(O)_p$—;

$R^1$, $R^4$ and $R^5$ are independently selected from the group consisting of hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —$NR^7R^8$, —$OR^7$, —$S(O)_pR^7$, —$S(O)NR^7R^8$, —$NR^7S(O)_pR^8$, —$NR^7C(O)R^8$, —$OS(O)_pR^8$, —NR C(O)$OR^8$, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(R^7R^8)_nNR^7R^8$, —$C(R^7R^8)_nCO(R^7)$ and —$S(O)_pC(R^7R^8)_nC(O)OR^7$; or when $R^4$ or $R^5$ are more than one, then any 2 $R^4$ or 2 $R^5$ independently, taken together can form a monocyclic or a bicyclic ring system which is saturated or partially unsaturated and which optionally comprises one or more additional heteroatoms selected from the group consisting of O, N and S;

wherein each substituent is unsubstituted or substituted with 1, 2, or 3 substituents independently selected from the group consisting of alkyl, halogen, haloalkyl, perhaloalkyl, haloalkoxy, perhaloalkoxy, cyano, alkoxy, —$(CR^aR^b)_nCOOR^7$, —$(CR^aR^b)_nNR^7R^8$, —$(CR^aR^b)_nC(O)NR^7R^8$, —$S(O)_pR^7$ and —$SO_3H$;

$R^2$ and $R^3$ are independently selected from the group consisting of halo, hydroxyl, cyano, $C_{1-6}$alkyl, haloalkyl, perhaloalkyl, cycloalkyl, cycloalkenyl, cycloalkylalkyl, aryl, and arylalkyl;

$R^6$ is selected from the group consisting of hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl and heterocyclylalkyl;

$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and which optionally comprises one or more additional heteroatoms selected from the group consisting of O, N and S, wherein said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

p=0-2; and
n=0-4.

3. A compound of formula (I) as claimed in claim 1 or its tautomers, polymorphs, stereoisomers, prodrugs, solvate or pharmaceutically acceptable salts thereof, wherein U, V and W are independently selected from the group consisting of CR' and CR'R";

G is CR';

R' and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally comprises one or more additional heteroatoms selected from the group consisting of O, N and S, wherein said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

T and Y are independently defined as either:
a) T is selected from the group consisting of cycloalkyl, cycloalkenyl and aryl;

wherein cycloalkyl, cycloalkenyl, cycloalkylalkyl, aryl and arylalkyl are unsubstituted or substituted independently with 1 to 4 substituents independently selected from the group consisting of halo, alkyl, alkenyl, alkynyl, nitro, cyano, —$(CR^aR^b)_nOR^6$, —$(CR^aR^b)_nSR^6$, —$(CR^aR^b)_nNR^7R^8$, oxo, alkylsulfonyl, —$(CR^aR^b)_nCOOR^6$, —$(CR^aR^b)_nC(O)NR^7R^8$, cycloalkyl, cycloalkylalkyl, aryl, heterocyclyl, and heterocyclylalkyl;

Y is selected from the group consisting of —O—, —$S(O)_p$—, —$N(R^7)$—, —C(O)—, —C(S)— and —$(CR^aR^b)$—; or b) T is cycloalkyl, cycloalkenyl, aryl, heterocyclyl or heteroaryl;

wherein cycloalkyl, aryl, heterocyclyl or heteroaryl; are unsubstituted or substituted independently with 1 to 4 substituents independently selected from the group consisting of halo, alkyl, alkenyl, alkynyl, nitro, cyano, —(CR$^a$R$^b$)$_n$OR$^6$, —(CR$^a$R$^b$)$_n$SR$^6$, —(CR$^a$R$^b$)$_n$NR$^7$R$^8$, oxo, alkylsulfonyl, —(CR$^a$R$^b$)$_n$COOR$^6$, —(CR$^a$R$^b$)$_n$C(O)NR$^7$R$^8$, cycloalkyl, cycloalkylalkyl, aryl, arylalkyl, heterocyclyl, heterocyclylalkyl, heteroaryl, and heteroarylalkyl;

Y is —C(O)— or —C(S)—;

R$^a$ and R$^b$ are independently selected from the group consisting of hydrogen, —OR$^7$, halogen, haloalkyl, perhaloalkyl and alkyl; or R$^a$ and R$^b$ taken together form a monocyclic or a bicyclic ring system which is saturated or partially unsaturated and which optionally comprises one or more additional heteroatoms selected from the group consisting of O, N and S;

X$^1$, X$^2$ and X$^3$ are each independently selected from the group consisting of N and CR$^7$;

Z is —C(O)— or —S(O)$_p$—;

R$^1$, R$^4$ and R$^5$ are independently selected from the group consisting of hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —NR$^7$R$^8$, —OR$^7$, —S(O)$_p$R$^7$, —S(O)$_p$NR$^7$R$^8$, —NR$^7$S(O)$_p$R$^8$, —NR$^7$C(O)R$^8$, —OS(O)$_p$R$^8$, —NRC(O)OR$^8$, —(CR$^7$R$^8$)$_n$C(O)OR$^7$, —(CR$^7$R$^8$)$_n$(CO)NR$^7$R$^8$, —(CR$^7$R$^8$)$_n$S(O)$_p$NR$^7$R$^8$, —(CR$^7$R$^8$)$_n$N(R$^7$)C(O)R$^7$, —(CR$^7$R$^8$)$_n$OR$^7$, —C(R$^7$R$^8$)$_n$NR$^7$R$^8$, —C(R$^7$R$^8$)$_n$CO(R$^7$) and —S(O)$_p$C(R$^7$R$^8$)$_n$C(O)OR$^7$; or when R$^4$ or R$^5$ are more than one, then any 2 R$^4$ or 2 R$^5$ independently, taken together form a monocyclic or a bicyclic ring system which is saturated or partially unsaturated and optionally comprise one or more additional heteroatoms selected from the group consisting of O, N and S;

wherein each substituent is unsubstituted or substituted with 1, 2, or 3 substituents independently selected from the group consisting of alkyl, halogen, haloalkyl, perhaloalkyl, haloalkoxy, perhaloalkoxy, cyano, alkoxy, —(CR$^a$R$^b$)$_n$COOR$^7$, —(CR$^a$R$^b$)$_n$NR$^7$R$^8$, —(CR$^a$R$^b$)$_n$C(O)NR$^7$R$^8$, —S(O)$_p$R$^7$ and —SO$_3$H;

R$^2$ and R$^3$ are independently selected from the group consisting of halo, hydroxyl, cyano, C$_{1-6}$alkyl, C$_{2-6}$alkenyl, C$_{2-6}$alkynyl, haloalkyl, perhaloalkyl, cycloalkyl, cycloalkenyl, cycloalkylalkyl, aryl, and arylalkyl;

R$^6$ is selected from the group consisting of hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl and heterocyclylalkyl;

R$^7$ and R$^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R$^7$ and R$^8$ taken together form a monocyclic or a bicyclic ring system which is saturated or partially unsaturated and which optionally comprises one or more additional heteroatoms selected from O, N or S, said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

p=0-2; and
n=0-4.

4. A compound of formula (I) as claimed in claim 1 or its tautomers, polymorphs, stereoisomers, prodrugs, solvate or a pharmaceutically acceptable salts thereof, wherein U, V and W are independently selected from the group consisting of CR' and CR'R";

G is CR';

R and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R' and R" taken together form a monocyclic or a bicyclic ring system which is saturated or partially unsaturated and optionally comprises one or more additional heteroatoms selected from the group consisting of O, N and S, said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

T and Y are independently defined as either a) T is cyclopropyl, cyclopentyl, cyclohexyl, cyclopentenyl, cyclohexenyl, or phenyl, wherein T is unsubstituted or substituted with 1 to 4 substituents independently selected from the group consisting of halo, alkyl, alkenyl, alkynyl, nitro, cyano, —(CR$^a$R$^b$)$_n$OR$^6$, —(CR$^a$R$^b$)$_n$SR$^6$, —(CR$^a$R$^b$)$_n$NR$^7$R$^8$, oxo, alkylsulfonyl, —(CR$^a$R$^b$)$_n$COOR$^6$, —(CR$^a$R$^b$)$_n$C(O)NR$^7$R$^8$, cycloalkyl, cycloalkylalkyl, aryl, arylalkyl, heterocyclyl, heterocyclylalkyl, heteroaryl, and heteroarylalkyl;

Y is a group selected from the group consisting of —O—, —S(O)$_p$—, —N(R$^7$)—, —C(O)—, —C(S)— and —(CR$^a$R$^b$)—; or b) T is selected from the group consisting of cyclopropyl, cyclopentyl, cyclohexyl, cyclopentenyl, cyclohexenyl, phenyl, tetrahydrofuranyl, pyrrolidinyl, pyridinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl and benzooxazolyl wherein T is unsubstituted or substituted with 1 to 4 substituents independently selected from the group consisting of halo, alkyl, alkenyl, alkynyl, nitro, cyano, —(CR$^a$R$^b$)$_n$OR$^6$, —(CR$^a$R$^b$)$_n$SR$^6$, —(CR$^a$R$^b$)$_n$NR$^7$R$^8$, oxo, alkylsulfonyl, —(CR$^a$R$^b$)$_n$COOR$^6$, —(CR$^a$R$^b$)$_n$C(O)NR$^7$R$^8$, cycloalkyl, cycloalkylalkyl, aryl, arylalkyl, heterocyclyl, heterocyclylalkyl, heteroaryl, and heteroarylalkyl;

Y is a group selected from the group consisting of —C(O)— and —C(S)—;

R$^a$ and R$^b$ are independently selected from the group consisting of hydrogen, —OR$^7$, halogen, haloalkyl, perhaloalkyl and alkyl; or R$^a$ and R$^b$ taken together form a monocyclic or a bicyclic ring system which is saturated or partially unsaturated and optionally comprises one or more additional heteroatoms selected from the group consisting of O, N and S;

X$^1$, X$^2$ and X$^3$ are each independently selected from the group consisting of N and CR$^7$;

Z is —C(O)— or —S(O)$_p$—;

$R^1$, $R^4$ and $R^5$ are independently selected from the group consisting of hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —$NR^7R^8$, —$OR^7$, —$S(O)_pR^7$, —$S(O)_pNR^7R^8$, —$NR^7S(O)_pR^8$, —$NR^7C(O)R^8$, —$OS(O)_pR^8$, —$NR^7C(O)OR^8$, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(CR^7R^8)_nNR^7R^8$, —$C(R^7R^8)_nCO(R^7)$ and —$S(O)_pC(R^7R^8)_nC(O)OR^7$; or when $R^4$ or $R^5$ are more than one, then any 2 $R^4$ or 2 $R^5$ independently, taken together form a monocyclic or a bicyclic ring system which is saturated or partially unsaturated and optionally comprise one or more additional heteroatoms selected from the group consisting of O, N and S;

wherein each substituent is unsubstituted or substituted with 1, 2, or 3 substituents independently selected from the group consisting of alkyl, halogen, haloalkyl, perhaloalkyl, haloalkoxy, perhaloalkoxy, cyano, alkoxy, —$(CR^aR^b)_nCOOR^7$, —$(CR^aR^b)_nNR^7R^8$, —$(CR^aR^b)_nC(O)NR^7R^8$, —$S(O)_pR^7$ and —$SO_3H$;

$R^2$ and $R^3$ are independently selected from the group consisting of halo, hydroxyl, cyano, $C_{1-6}$alkyl, $C_{2-6}$alkenyl, $C_{2-6}$alkynyl, haloalkyl, perhaloalkyl, cycloalkyl, cycloalkenyl, cycloalkylalkyl, aryl, and arylalkyl;

$R^6$ is hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

$R^7$ and $R^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or $R^7$ and $R^8$ taken together form a monocyclic or a bicyclic ring system which is saturated or partially unsaturated and optionally comprises one or more additional heteroatoms selected from the group consisting of O, N and S, wherein said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

p=0-2; and n=0-4.

5. A compound of formula (I) as claimed in claim 1 or its tautomers, polymorphs, stereoisomers, prodrugs, solvate or a pharmaceutically acceptable salts thereof, wherein U, V and W are independently selected from the group consisting of CR' and CR'R";

G is CR';

R and R" are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl; or R' and R" taken together form a monocyclic or a bicyclic ring system which is saturated or partially unsaturated and optionally comprises one or more additional heteroatoms selected from the group consisting of O, N and S, said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

T is cyclopropyl, cyclopentyl, cyclohexyl, cyclopentenyl, cyclohexenyl, phenyl, tetrahydrofuranyl, pyrrolidinyl, pyridinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl or benzooxazolyl, wherein T is unsubstituted or substituted with 1 to 4 substituents independently selected from the group consisting of halo, alkyl, alkenyl, alkynyl, nitro, cyano, —$(CR^aR^b)_nOR^6$, —$(CR^aR^b)_nSR^6$, —$(CR^aR^b)_nNR^7R^8$, oxo, alkylsulfonyl, —$(CR^aR^b)_nCOOR^6$, —$(CR^aR^b)_nC(O)NR^7R^8$, cycloalkyl, cycloalkylalkyl, aryl, arylalkyl, heterocyclyl, heterocyclylalkyl, heteroaryl, and heteroarylalkyl;

wherein when T is cyclopropyl, cyclopentyl, cyclohexyl, cyclopentenyl, cyclohexenyl, or phenyl, Y is selected from the group consisting of —O—, —$S(O)_p$—, —$N(R^7)$—, —$C(O)$—, —$C(S)$— and —$(CR^aR^b)$—; and wherein when T is tetrahydrofuranyl, pyrrolidinyl, pyridinyl, tetrahydropyridinyl, tetrahydropyranyl, piperazinyl, benzodiaxolyl, tetrahydroquinolinyl, morpholinyl, tetrahydronaphthyridinyl, tetrahydrothienopyridinyl, furanyl, pyridinyl, pyrimidinyl, oxazolyl, thiazolyl, oxadiazolyl, thiadiazolyl, indolyl, quinolinyl, isoquinolinyl or benzooxazolyl, Y is —$C(O)$—; or —$C(S)$—;

$R^a$ and $R^b$ are independently selected from the group consisting of hydrogen, —$OR^7$, halogen, haloalkyl, perhaloalkyl and alkyl; or $R^a$ and $R^b$ taken together form a monocyclic or a bicyclic ring system which is saturated or partially unsaturated and optionally comprises one or more additional heteroatoms selected from the group consisting of O, N and S;

$X^1$, $X^2$ and $X^3$ are each independently selected from N and $CR^7$;

Z is —$C(O)$— or —$S(O)_p$—;

$R^1$, $R^4$ and $R^5$ are independently selected from the group consisting of hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —$NR^7R^8$, —$OR^7$, —$S(O)_pR^7$, —$S(O)NR^7R^8$, —$NR^7S(O)_pR^8$, —$NR^7C(O)R^8$, —$OS(O)_pR^8$, —$NR^7C(O)OR^8$, —$(CR^7R^8)_nC(O)OR^7$, —$(CR^7R^8)_n(CO)NR^7R^8$, —$(CR^7R^8)_nS(O)_pNR^7R^8$, —$(CR^7R^8)_nN(R^7)C(O)R^7$, —$(CR^7R^8)_nOR^7$, —$C(CR^7R^8)_nNR^7R^8$, —$C(R^7R^8)_nCO(R^7)$ and —$S(O)_pC(R^7R^8)_nC(O)OR^7$; or when $R^4$ or $R^5$ are more than one, then any 2 $R^4$ or 2 $R^5$ independently is optionally, taken together form a monocyclic or a bicyclic ring system which is saturated or partially unsaturated and optionally comprises one or more additional heteroatoms selected from the group consisting of O, N and S;

wherein each substituent is unsubstituted or substituted with 1, 2, or 3 substituents independently selected from the group consisting of alkyl, halogen, haloalkyl, perhaloalkyl, haloalkoxy, perhaloalkoxy, cyano, alkoxy, —(CR$^a$R$^b$)$_n$COOR$^7$, —(CR$^a$R$^b$)$_n$NR$^7$R$^8$, —(CR$^a$R$^b$)$_n$C(O)NR$^7$R$^8$, —S(O)$_p$R$^7$ and —SO$_3$H;

R$^2$ and R$^3$ are independently selected from the group consisting of halo, hydroxyl, cyano, C$_{1-6}$alkyl, C$_{2-6}$alkenyl, C$_{2-6}$ alkynyl, haloalkyl, perhaloalkyl, cycloalkyl, cycloalkenyl, cycloalkylalkyl, aryl, and arylalkyl;

R$^6$ is selected from the group consisting of hydrogen, alkyl, haloalkyl, alkoxy, carboxy, aminocarbonyl, cycloalkyl, cycloalkylalkyl, aryl, arylalkyl, heteroaryl, heteroarylalkyl, heterocyclyl or heterocyclylalkyl;

R$^7$ and R$^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, or R$^7$ and R$^8$ taken together form a monocyclic or a bicyclic ring system which is saturated or partially unsaturated and optionally comprise one or more additional heteroatoms selected from O, N or S, said ring system is further optionally substituted with 1 to 4 substituents independently selected from the group consisting of halo, alkyl, haloalkyl, alkenyl, alkynyl, nitro, cyano, alkoxy, amino, oxo, alkylsulfonyl, carboxy, cycloalkyl, cycloalkylalkyl, aryl, arylalkyl, heterocyclyl, heterocyclylalkyl, heteroaryl, and heteroarylalkyl;

p=0-2; and
n=0-4.

6. A compound of formula (I) as claimed in claim 1 or its tautomers,
polymorphs, stereoisomers, prodrugs, solvate or a pharmaceutically acceptable salts thereof, wherein U, V and W are independently selected from the group consisting of CR' and CR'R";

G is CR';

R and R" are independently selected from the group consisting of hydrogen, alkyl, haloalkyl, alkoxy, carboxy, hydroxyl and cyano, T is cyclohexenyl, phenyl, pyridyl, or tetrahydropyridinyl;

Y is —C(O)—
X$^1$, X$^2$ and X$^3$ are CR$^7$;

Z is —C(O)—;

R$^1$, R$^4$ and R$^5$ are independently selected from the group consisting of hydrogen, halogen, alkyl, hydroxy, alkoxy, amino, alkenyl, alkynyl, cycloalkyl, cycloalkylalkyl, heterocyclyl, heterocycloalkyl, aryl, arylalkyl, heteroaryl, heteroarylalkyl, tetrazolyl, tetrazolylalkyl, mono, di or tri substituted haloalkyl, nitrile, nitro, oxo, —(CR$^7$R$^8$)$_n$C(O)OR$^7$, —(CR$^7$R$^8$)$_n$(CO)NR$^7$R$^8$, —(CR$^7$R$^8$)$_n$S(O)$_p$NR$^7$R$^8$, —(CR$^7$R$^8$)$_n$N(R$^7$)C(O)R$^7$, —(CR$^7$R$^8$)$_n$OR$^7$, —C(R$^7$R$^8$)$_n$NR$^7$R$^8$, —C(R$^7$R$^8$)$_n$CO(R$^7$) and —S(O)$_p$C(R$^7$R$^8$)$_n$C(O)OR$^7$;

wherein each substituent is unsubstituted or substituted with 1, 2, or 3 substituents independently selected from the group consisting of alkyl, halogen, haloalkyl, perhaloalkyl, haloalkoxy, perhaloalkoxy, cyano, alkoxy, —(CR$^a$R$^b$)$_n$COOR$^7$, —(CR$^a$R$^b$)$_n$NR$^7$R$^8$, —(CR$^a$R$^b$)$_n$C(O)NR$^7$R$^8$, —S(O)$_p$R$^7$ and —SO$_3$H;

R$^2$ and R$^3$ are independently selected from the group consisting of halo, hydroxyl, cyano, and perhaloalkyl, R$^7$ and R$^8$ are independently selected from the group consisting of hydrogen, alkyl, haloalkyl, alkoxy, carboxy, hydroxyl, cyano, aryl, arylalkyl, heteroaryl, heteroarylalkyl, cycloalkyl, cycloalkylalkyl, heterocyclyl and heterocyclylalkyl, p=0-2; and
n=0-4.

7. A compound of formula (I) as claimed in claim 1 or its tautomers, polymorphs, stereoisomers, prodrugs, solvate or a pharmaceutically acceptable salts thereof, which is Ethyl 4-[3-[2-chloro-6-(trifluoromethyl)benzoyl]indolizin-1-yl]benzoate;

4-[3-[2-chloro-6-(trifluoromethyl)benzoyl]indolizin-1-yl] benzoic acid;

4-[3-(2,6-dichlorobenzoyl)indolizin-1-yl]-3-fluoro-benzoic acid;

methyl 4-[3-(2,6-dichlorobenzoyl)indolizin-1-yl]-3-fluoro-benzoate;

methyl 4-[3-(2,6-difluorobenzoyl)indolizin-1-yl]-3-fluoro-benzoate;

ethyl 4-[3-(2,6-dichlorobenzoyl)indolizin-1-yl]benzoate;

methyl 4-[3-(2,6-dichlorobenzoyl)indolizin-1-yl]-3,5-difluoro-benzoate;

4-[3-(2,6-dichlorobenzoyl)indolizin-1-yl]benzoic acid;

4-[3-(2,6-dichlorobenzoyl)indolizin-1-yl]-3,5-difluoro-benzoic acid;

5-[3-(2,6-dichlorobenzoyl)indolizin-1-yl]pyridine-2-carboxylic acid;

methyl 4-[3-[2-chloro-6-(trifluoromethyl)benzoyl]indolizin-1-yl]-3-fluoro-benzoate;

4-[3-[2-chloro-6-(trifluoromethyl)benzoyl]indolizin-1-yl]-3-fluoro-benzoic acid;

methyl 4-[3-(2-chloro-6-methyl-benzoyl)indolizin-1-yl]-3-fluoro-benzoate;

ethyl 4-[3-(2-chloro-6-methyl-benzoyl)indolizin-1-yl] benzoate;

4-[3-(2-chloro-6-methyl-benzoyl)indolizin-1-yl]-3-fluoro-benzoic acid;

4-[3-(2-chloro-6-methyl-benzoyl)indolizin-1-yl]benzoic acid;

methyl 4-[3-(2,6-dichloro-3-fluoro-benzoyl)indolizin-1-yl]-3-fluoro-benzoate;

4-[3-(2,6-dichloro-3-fluoro-benzoyl)indolizin-1-yl]-3-fluoro-benzoic acid;

4-[3-(2,6-dichloro-3-fluoro-benzoyl)indolizin-1-yl]benzoic acid;

(2,6-dichlorophenyl)-[1-(4-methylsulfonylphenyl)indolizin-3-yl]methanone;

ethyl 4-[3-(2,6-dichlorobenzoyl)-8-fluoro-indolizin-1-yl] benzoate;

methyl 4-[3-(2,6-dichlorobenzoyl)-8-fluoro-indolizin-1-yl]-3-fluoro-benzoate;

4-[3-(2,6-dichlorobenzoyl)-8-fluoro-indolizin-1-yl]benzoic acid;

ethyl 4-[3-(2-chloro-6-fluoro-benzoyl)indolizin-1-yl]benzoate;

ethyl 4-[3-(2-chloro-6-fluoro-benzoyl)indolizin-1-yl]-3-fluoro-benzoate;

4-[3-(2,6-dichlorobenzoyl)-6-fluoro-indolizin-1-yl]benzoic acid;

4-[3-(2-chloro-6-fluoro-benzoyl)indolizin-1-yl]-3-fluoro-benzoic acid;

4-[3-(2-chloro-6-fluoro-benzoyl)indolizin-1-yl]benzoic acid;

4-[3-(2-chloro-6-cyclopropyl-benzoyl)indolizin-1-yl]-3-fluoro-benzoic acid;

ethyl 4-[3-(2-chloro-6-cyclopropyl-benzoyl)indolizin-1-yl]-3-fluoro-benzoate;

ethyl 4-[3-(2-chloro-6-cyclopropyl-benzoyl)indolizin-1-yl]benzoate;

ethyl 4-[3-(2-chloro-6-fluoro-benzoyl)-8-fluoro-indolizin-1-yl]benzoate;

ethyl 4-[3-(2-chloro-6-fluoro-benzoyl)-8-fluoro-indolizin-1-yl]-3-fluoro-benzoate;

4-[3-(2-chloro-6-fluoro-benzoyl)-8-fluoro-indolizin-1-yl] benzoic acid;
4-[3-(2-chloro-6-fluoro-benzoyl)-8-fluoro-indolizin-1-yl]-3-fluoro-benzoic acid;
ethyl 4-[3-(2,6-difluorobenzoyl)indolizin-1-yl]benzoate;
4-[3-(2,6-difluorobenzoyl)indolizin-1-yl]benzoic acid;
ethyl 4-[3-(2,6-difluorobenzoyl)indolizin-1-yl]-3-fluorobenzoate;
4-[3-(2,6-difluorobenzoyl)indolizin-1-yl]-3-fluoro-benzoic acid;
[1-(p-tolyl)indolizin-3-yl]-(2,3,6-trifluorophenyl)methanone;
ethyl 3-fluoro-4-[3-(2,3,6-trifluorobenzoyl)indolizin-1-yl]benzoate;
4-[3-(2,3,6-trifluorobenzoyl)indolizin-1-yl]benzoic acid;
4-[3-(2,6-dichloro-3-fluoro-benzoyl)-8-fluoro-indolizin-1-yl]benzoic acid;
3-fluoro-4-[3-(2,3,6-trifluorobenzoyl)indolizin-1-yl]benzoic acid;
ethyl 4-[3-(2,6-difluorobenzoyl)-8-fluoro-indolizin-1-yl]benzoate;
ethyl 4-[3-(2,6-difluorobenzoyl)-8-fluoro-indolizin-1-yl]-3-fluoro-benzoate;
4-[3-(2,6-difluorobenzoyl)-8-fluoro-indolizin-1-yl]benzoic acid;
4-[3-(2,6-difluorobenzoyl)-8-fluoro-indolizin-1-yl]-3-fluoro-benzoic acid;
4-[3-(2,6-dichloro-3-fluoro-benzoyl)-8-fluoro-indolizin-1-yl]-3-fluoro-benzoic acid;
4-[3-(2-bromo-6-chloro-benzoyl)indolizin-1-yl]benzoic acid;
4-[3-(2-chloro-6-fluoro-benzoyl)indolizin-1-yl]benzoic acid;
4-[3-(2-bromo-6-chloro-benzoyl)indolizin-1-yl]-3-fluoro-benzoic acid;
4-[3-(2,6-dibromobenzoyl)indolizin-1-yl]benzoic acid;
tert-butyl 4-[3-(2,6-dichlorobenzoyl)indolizin-1-yl]-3,6-dihydro-2H-pyridine-1-carboxylate;
tert-butyl 5-[3-(2,6-dichloro-3-fluoro-benzoyl)indolizin-1-yl]-3,6-dihydro-2H-pyridine-1-carboxylate;
ethyl 4-[3-(2,6-dichloro-3-fluoro-benzoyl)indolizin-1-yl]benzoate;
3-[3-[2-chloro-6-(trifluoromethyl)benzoyl]indolizin-1-yl]benzoic acid;
4-[8-chloro-3-[2-chloro-6-(trifluoromethyl)benzoyl]indolizin-1-yl]benzoic acid;
4-[8-chloro-3-[2-chloro-6-(trifluoromethyl)benzoyl]indolizin-1-yl]-3-fluoro-benzoic acid;
4-[3-[2-chloro-6-(trifluoromethyl)benzoyl]indolizin-1-yl]-2-fluoro-benzoic acid;
4-[3-(2,6-dichlorobenzoyl)-8-(trifluoromethyl)indolizin-1-yl]benzoic acid;
ethyl 4-[3-(2,6-dichlorobenzoyl)-8-(trifluoromethyl)indolizin-1-yl]benzoate;
4-[3-(2,6-dichlorobenzoyl)-6-(trifluoromethyl)indolizin-1-yl]benzoic acid;
ethyl 4-[3-(2,6-dichlorobenzoyl)-6-(trifluoromethyl)indolizin-1-yl]benzoate;
4-[3-[2-chloro-6-(trifluoromethyl)benzoyl]indolizin-1-yl]cyclohex-3-ene-1-carboxylic acid;
ethyl 4-[3-(2-bromo-6-methyl-benzoyl)indolizin-1-yl]benzoate;
Ethyl 4-[3-(2,6-dichlorobenzoyl)-2-fluoro-indolizin-1-yl]benzoate;
4-[3-(2,6-dichlorobenzoyl)-2-fluoro-indolizin-1-yl]benzoic acid;
methyl 4-[3-(2,6-dichlorobenzoyl)-2-fluoro-indolizin-1-yl]-3-fluoro-benzoate;
4-[3-(2,6-dichlorobenzoyl)-2-fluoro-indolizin-1-yl]-3-fluoro-benzoic acid;
ethyl 4-[3-(2,6-dichloro-3-fluoro-benzoyl)-2-fluoro-indolizin-1-yl]benzoate;
4-[3-(2,6-dichloro-3-fluoro-benzoyl)-2-fluoro-indolizin-1-yl]benzoic acid;
ethyl 4-[3-(2,6-dichlorobenzoyl)-2-methyl-indolizin-1-yl]-3-fluoro-benzoate;
4-[3-(2,6-dichlorobenzoyl)-2-methyl-indolizin-1-yl]-3-fluoro-benzoic;
ethyl 4-[3-(2,6-dichlorobenzoyl)-2-methyl-indolizin-1-yl]benzoate;
4-[3-(2,6-dichlorobenzoyl)-2-methyl-indolizin-1-yl]benzoic acid;
4-[3-(2,4-dichloropyridine-3-carbonyl)-2-methyl-indolizin-1-yl]benzoic acid;
4-[3-[2-chloro-6-(trifluoromethyl)benzoyl]-2-methyl-indolizin-1-yl]-3-fluoro-benzoic acid;
4-[3-[2-chloro-6-(trifluoromethyl)benzoyl]-2-methyl-indolizin-1-yl]benzoic acid;
methyl 4-[3-[2-chloro-6-(trifluoromethyl)benzoyl]-2-methyl-indolizin-1-yl]-3-fluoro-benzoate;
ethyl 4-[3-[2-chloro-6-(trifluoromethyl)benzoyl]-2-methyl-indolizin-1-yl]benzoate;
ethyl 4-[3-(2,4-dichloropyridine-3-carbonyl)-2-methyl-indolizin-1-yl]benzoate;
4-[3-[2-chloro-6-(trifluoromethyl)benzoyl]-6-(dimethylcarbamoyl) indolizin-1-yl]benzoic acid;
4-[3-(2,6-dichlorobenzoyl)-6-(dimethylcarbamoyl)indolizin-1-yl]benzoic acid;
4-[3-(2,6-dichlorobenzoyl)-6-(morpholine-4-carbonyl)indolizin-1-yl]benzoic acid;
4-[3-(2,6-dichlorobenzoyl)-6-(piperidine-1-carbonyl)indolizin-1-yl]benzoic acid;
4-[3-(2,6-dichlorobenzoyl)-6-(pyrrolidine-1-carbonyl)indolizin-1-yl]benzoic acid;
4-[6-(azetidine-1-carbonyl)-3-(2,6-dichlorobenzoyl)indolizin-1-yl]benzoic acid;
4-[3-(2,6-dichlorobenzoyl)-6-(2-hydroxyethylcarbamoyl)indolizin-1-yl]benzoic acid;
4-[3-(2,6-dichlorobenzoyl)-6-(2-methoxyethylcarbamoyl)indolizin-1-yl]benzoic acid;
4-[3-(2,6-dichlorobenzoyl)-6-(methylcarbamoyl)indolizin-1-yl]benzoic acid;
4-[3-(2,6-dichlorobenzoyl)-6-(4H-1,2,4-triazol-3-yl)indolizin-1-yl]benzoic acid;
4-[6-(azetidine-1-carbonyl)-3-[2-chloro-6-(trifluoromethyl)benzoyl]indolizin-1-yl]benzoic acid;
4-[3-[2-chloro-6-(trifluoromethyl)benzoyl]-6-(pyrrolidine-1-carbonyl)indolizin-1-yl]benzoic acid;
4-[6-carbamoyl-3-(2,6-dichlorobenzoyl)indolizin-1-yl]benzoic acid;
4-[3-(2,6-dichlorobenzoyl)-6-(3-methoxyazetidine-1-carbonyl)indolizin-1-yl]benzoic acid;
methyl 4-[3-(2,6-dichlorophenoxy)indolizin-1-yl]-3-fluoro-benzoate;
4-[3-(2,6-dichlorophenoxy)indolizin-1-yl]benzoic acid;
4-[3-(2,6-dichlorophenoxy)indolizin-1-yl]benzoic acid;
4-[3-(2,6-dichloro-3-fluoro-benzoyl)imidazo[1,5-a]pyridin-1-yl]-N-methyl-benzamide;
4-[3-(2,6-dichloro-3-fluoro-benzoyl)indolizin-1-yl]-N,N-dimethyl-benzamide; [4-[3-(2,6-dichloro-3-fluoro-benzol)indolizin-1-yl]phenyl]- morpholino-methanone;
(2,6-dichloro-3-fluoro-phenyl)-[1-(1-ethylsulfonyl-3,6-dihydro-2H-pyridin-5-yl)indolizin-3-yl]methanone;

4-[3-[2-chloro-6-(trifluoromethyl)benzoyl]-5,6,7,8-tetrahydroindolizin-1-yl]benzoic acid;
4-[3-(2,6-dichlorobenzoyl)-2-methyl-5,6,7,8-tetrahydroindolizin-1-yl]-3-fluoro-benzoic acid;
4-[3-(2,6-dichloro-3-fluoro-benzoyl)-5,6,7,8 tetrahydroindolizin-1-yl]benzoic acid;
4-[3-[2-chloro-6-(trifluoromethyl)benzoyl]-5,6,7,8-tetrahydroindolizin-1-yl]-3-fluoro-benzoic acid;
4-[3-(2-chloro-6-methyl-benzoyl)-5,6,7,8-tetrahydroindolizin-1-yl]benzoic acid;
4-[3-[(2-chloro-6-fluoro-phenyl)methyl]indolizin-1-yl]benzoic acid;
4-[3-(2,6-dichlorobenzoyl)indolizin-1-yl]cyclohexanecarboxylic acid;
4-[3-[2-chloro-6-(trifluoromethyl)benzoyl]indolizin-1-yl]cyclohexanecarboxylic acid;
4-[3-[2-chloro-6-(trifluoromethyl)benzoyl]indolizin-1-yl]cyclohex-3-ene-1-carboxylic acid;
4-[3-(2,6-dichlorobenzoyl)indolizin-1-yl]cyclohexanecarboxylic acid;
1-[3-[2-chloro-6-(trifluoromethyl)benzoyl]indolizin-1-yl]piperidine-4-carboxylic acid;
4-[3-(2,6-dichlorobenzoyl)indolizin-1-yl]cyclohexanecarboxylic acid;
5-[3-(2,6-dichlorobenzoyl)indolizin-1-yl]norbornane-2-carboxylic acid;
4-[3-(2,6-dichlorobenzoyl)indolizin-1-yl]norbornane-1-carboxylic acid;
8-[3-[2-chloro-6-(trifluoromethyl)benzoyl]indolizin-1-yl]spiro[2.5]octane-5-carboxylic acid;
5-[3-[2-chloro-6-(trifluoromethyl)benzoyl]indolizin-1-yl]spiro[2.5]octane-8-carboxylic acid;
4-[3-(2,6-dichlorobenzoyl)indolizin-1-yl]-2-hydroxy-cyclohexanecarboxylic acid;
4-[3-[2-chloro-6-(trifluoromethyl)benzoyl]indolizin-l-yl]-3-hydroxy-cyclohexanecarboxylic acid;
4-[3-(2,6-dichlorobenzoyl)indolizin-1-yl]-5-fluoro-2-hydroxy-benzoic acid;
4-[3-(2,6-dichlorobenzoyl)-8-fluoro-indolizin-1-yl]-5-fluoro-2-hydroxy-benzoic acid;
4-[3-[2-chloro-6-(1-hydroxycyclobutyl)benzoyl]indolizin-1-yl]benzoic acid;
4-[3-[2-chloro-6-(trifluoromethyl)benzoyl]indolizin-1-yl]-2-fluoro-5-hydroxy-benzoic acid;
4-[3-(2,6-dichlorobenzoyl)-6-(1H-1,2,4-triazol-5-yl)indolizin-1-yl]cyclohexanecarboxylic acid;
4-[3-[(2-chloro-6-methyl-phenyl)methyl]indolizin-1-yl]benzoic acid;
4-[3-[(2,6-dichlorophenyl)methyl]-8-fluoro-indolizin-1-yl]-2-fluoro-benzoic acid;
4-[3-[(2,3,6-trichlorophenyl)methyl]indolizin-1-yl]benzoic acid;
4-[3-methyl]indolizin-1-yl]cyclohex-3-ene-1-carboxylic acid;
1-[3-[[2-chloro-6-(trifluoromethyl)phenyl]methyl]indolizin-1-yl]piperidine-4-carboxylic acid;
(1R)-4-[3-[[2-chloro-6-(trifluoromethyl)phenyl]methyl]indolizin-1-yl]cyclohex-3-ene-1-carboxylic acid;
4-[3-[(2,6-dichlorophenyl)-hydroxy-methyl]indolizin-1-yl]benzoic acid;
4-[3-[(2,6-dichlorophenyl)-difluoro-methyl]indolizin-1-yl]benzoic acid;
4-[3-[1-(2,6-dichlorophenyl)-1-methyl-ethyl]indolizin-1-yl]benzoic acid;
4-[3-[1-(2,6-dichlorophenyl)cyclopropyl]indolizin-1-yl]benzoic acid;
4-[3-[3-(2,6-dichlorophenyl)oxetan-3-yl]indolizin-1-yl]benzoic acid;
4-[3-(2,6-dichlorophenyl)sulfanylindolizin-1-yl]benzoic acid;
4-[3-(2,6-dichlorophenyl)sulfonylindolizin-1-yl]benzoic acid;
4-[3-(2,6-dichloroanilino)indolizin-1-yl]benzoic acid;
4-[3-(2,6-dichloro-N-methyl-anilino)indolizin-1-yl]benzoic acid;
4-[1-[(2,6-dichlorophenyl)methyl]indolizin-3-yl]benzoic acid;
4-[1-[(2,6-dichlorophenyl)-difluoro-methyl]indolizin-3-yl]benzoic acid;
4-[1-[1-(2,6-dichlorophenyl)cyclopropyl]indolizin-3-yl]benzoic acid;
4-[3-[2-chloro-6-(trifluoromethyl)benzoyl]-6-(morpholine-4-carbonyl)indolizin-1-yl]-2,5-difluoro-benzoic acid;
4-[3-(2-chloro-6-methoxy-benzoyl)-5,6,7,8-tetrahydroindolizin-1-yl]cyclohex-3-ene-1-carboxylic acid;
4-[3-(2,6-dichlorobenzoyl)indolizin-1-yl]cyclohex-3-ene-1-carboxylic acid;
1-[3-(2,6-dichlorobenzoyl)indolizin-1-yl]piperidine-4-carboxylic acid;
4-[3-[2-chloro-6-(trifluoromethyl)benzoyl]indolizin-1-yl]benzoic acid;
4-[3-(2-bromo-6-chloro-benzoyl)indolizin-1-yl]benzoic acid;
4-[3-(2,6-dichlorobenzoyl)-5,6,7,8-tetrahydroindolizin-1-yl]-2-fluoro-benzoic acid;
4-[3-(2,6-dichlorobenzoyl)-5,6,7,8-tetrahydroindolizin-1-yl]benzoic acid;
4-[3-[2-chloro-6-(trifluoromethyl)benzoyl]-5,6,7,8-tetrahydroindolizin-1-yl]-2-fluoro-benzoic acid;
4-[3-[2-chloro-6-(trifluoromethyl)benzoyl]spiro[6,7-dihydro-5H-indolizine-8,1'-cyclopropane]-1-yl]-2-fluoro-benzoic acid;
4-[3-[2-chloro-6-(trifluoromethyl)benzoyl]spiro[7,8-dihydro-6H-indolizine-5,1'-cyclopropane]-1-yl]-2-fluoro-benzoic acid;
4-[3-(3,5-dichloropyridine-4-carbonyl)indolizin-1-yl]benzoic acid;
4-[3-(2,6-dichlorobenzoyl)indolizin-l-yl]-1H-imidazole-2-carboxylic acid;
6-[3-(2-chloro-6-cyclopropyl-benzoyl)indolizin-1-yl]pyridine-3-carboxylic acid;
2-[3-(2,6-dichloro-4-fluoro-benzoyl)indolizin-l-yl]pyrimidine-5-carboxylic acid;
4-[3-(2-chloro-6-fluoro-benzoyl)-8-cyano-indolizin-1-yl]-3-fluoro-benzoic acid;
4-[3-(2-chloro-6-fluoro-benzoyl)-5-cyano-indolizin-1-yl]-2-fluoro-benzoic acid;
6-[3-[(2,4,6-trichlorophenyl)methyl]indolizin-1-yl]pyridine-3-carboxylic acid;
5-[3-[2-chloro-6-(trifluoromethyl)benzoyl]indolizin-1-yl]pyrazine-2-carboxylic acid;
4-[3-[2-chloro-6-(trifluoromethyl)benzoyl]spiro[6,8-dihydro-5H-indolizine-7,1'-cyclopropane]-1-yl]benzoic acid;
4-[3-(2,6-dichloro-3-fluoro-benzoyl)indolizin-1-yl]benzenesulfonic acid;
4-[3-(2,6-dichloro-3-fluoro-benzoyl)indolizin-1-yl]-3-fluoro-benzenesulfonic acid;
4-[3-(2,6-dichloro-3-fluoro-benzoyl)-6-(dimethylcarbamoyl)indolizin-1-yl]benzenesulfonic acid;
4-[3-(2,6-dichloro-3-fluoro-benzoyl)-5,6,7,8-tetrahydroindolizin-1-yl]-3-fluoro-benzenesulfonic acid or 4-[3-(2,6-dichloro-3-fluoro-benzoyl)-6-(dimethylcarbamoyl)-5,6,7,8-tetrahydroindolizin-1-yl]benzenesulfonic acid.

8. A compound of formula (I) as claimed in claim 1 or its tautomers, polymorphs, stereoisomers, prodrugs, solvate or a pharmaceutically acceptable salts thereof, which is 4-[3-[2-chloro-6-(trifluoromethyl)benzoyl]indolizin-1-yl]benzoic acid;

4-[3-(2,6-dichlorobenzoyl)indolizin-1-yl]benzoic acid;

4-[3-[2-chloro-6-(trifluoromethyl)benzoyl]indolizin-1-yl]-3-fluoro-benzoic acid;

4-[3-(2,6-dichloro-3-fluoro-benzoyl)indolizin-1-yl]benzoic acid;

4-[3-(2,6-dichlorobenzoyl)-8-fluoro-indolizin-1-yl]benzoic acid;

4-[3-[2-bromo-6-(trifluoromethoxy)benzoyl]indolizin-1-yl]benzoic acid;

4-[3-[2-chloro-6-(trifluoromethyl)benzoyl]-6-(dimethylcarbamoyl)indolizin-1-yl]benzoic acid;

4-[3-(2,6-dichlorobenzoyl)-6-(dimethylcarbamoyl)indolizin-1-yl]benzoic acid;

4-[3-[2-chloro-6-(trifluoromethyl)benzoyl]-6-(pyrrolidine-1-carbonyl)indolizin-1-yl]benzoic acid; or 4-[3-[2-chloro-6-(trifluoromethyl)benzoyl]-5,6,7,8-tetrahydroindolizin-1-yl]benzoic acid.

9. A pharmaceutical composition comprising at least one compound of formula (I), as claimed in claim 1, or its tautomers, polymorphs, stereoisomers, prodrugs, solvate or a pharmaceutically acceptable salts thereof, together with one or more pharmaceutically acceptable carriers or excipients.

10. The pharmaceutical composition of claim 9, further comprising at least one additional therapeutically active agent.

* * * * *